US009822370B2

(12) United States Patent
Musunuru et al.

(10) Patent No.: US 9,822,370 B2
(45) Date of Patent: Nov. 21, 2017

(54) METHOD OF MAKING A DELETION IN A TARGET SEQUENCE IN ISOLATED PRIMARY CELLS USING CAS9 AND TWO GUIDE RNAS

(71) Applicants: President and Fellows of Harvard College, Cambridge, MA (US); The Children's Medical Center Corporation, Boston, MA (US)

(72) Inventors: Kiran Musunuru, Cambridge, MA (US); Chad A. Cowan, Boston, MA (US); Derrick J. Rossi, Roslindale, MA (US)

(73) Assignees: President and Fellows of Harvard College, Cambridge, MA (US); The Children's Medical Center Corporation, Boston, MA (US)

(*) Notice: Subject to any disclaimer, the term of this patent is extended or adjusted under 35 U.S.C. 154(b) by 0 days.

(21) Appl. No.: 14/485,288

(22) Filed: Sep. 12, 2014

(65) Prior Publication Data

US 2015/0071889 A1 Mar. 12, 2015

Related U.S. Application Data

(63) Continuation of application No. PCT/US2014/033082, filed on Apr. 4, 2014.

(60) Provisional application No. 61/808,594, filed on Apr. 4, 2013.

(51) Int. Cl.
| | | |
|---|---|---|
| *C12N 15/00* | (2006.01) | |
| *C12N 15/63* | (2006.01) | |
| *C12N 15/90* | (2006.01) | |
| *A61K 48/00* | (2006.01) | |

(52) U.S. Cl.
CPC .......... *C12N 15/63* (2013.01); *C12N 15/907* (2013.01); *A61K 48/00* (2013.01)

(58) Field of Classification Search
USPC .................................................. 435/455, 325
See application file for complete search history.

(56) References Cited

U.S. PATENT DOCUMENTS

| | | |
|---|---|---|
| 8,013,143 B2 | 9/2011 | Mcswiggen et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 2002/0106742 A1 | 8/2002 | Samson et al. |
| 2006/0024819 A1 | 2/2006 | Finney |
| 2008/0188000 A1* | 8/2008 | Reik et al. .................... 435/463 |
| 2010/0062003 A1 | 3/2010 | Murphy et al. |
| 2010/0076057 A1 | 3/2010 | Sontheimer et al. |
| 2010/0093617 A1 | 4/2010 | Barrangou et al. |
| 2010/0227805 A1 | 9/2010 | Karin et al. |
| 2011/0262406 A1 | 10/2011 | Del Campo et al. |
| 2011/0300538 A1 | 12/2011 | Barrangou et al. |
| 2012/0088676 A1 | 4/2012 | Weill et al. |
| 2012/0142062 A1 | 6/2012 | Doyon et al. |
| 2012/0192298 A1 | 7/2012 | Weinstein et al. |
| 2012/0225927 A1 | 9/2012 | Sah et al. |
| 2012/0251618 A1 | 10/2012 | Schrum et al. |
| 2013/0122591 A1 | 5/2013 | Cost et al. |
| 2013/0156849 A1 | 6/2013 | De Fougerolles |
| 2013/0288251 A1 | 10/2013 | Horvath et al. |
| 2013/0330778 A1 | 12/2013 | Zainer et al. |
| 2014/0080216 A1 | 3/2014 | Cost et al. |
| 2014/0093913 A1 | 4/2014 | Cost et al. |
| 2014/0134143 A1 | 5/2014 | Baylink et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang et al. |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273230 A1 | 9/2014 | Chen et al. |
| 2014/0273231 A1 | 9/2014 | Zhang |

(Continued)

FOREIGN PATENT DOCUMENTS

| | | |
|---|---|---|
| WO | WO 2013/016446 | 1/2013 |
| WO | WO 2013/126794 A1 | 8/2013 |

(Continued)

OTHER PUBLICATIONS

Porteus (Nature Biotech., 2005, vol. 23, No. 8, p. 967-973).*
Ramirez (Unexpected failure rates for modular assembly of engineered zinc fingers. Nature Methods, 2008, 5(5): 374-375).*
Geurts (Science, Jul. 24, 2009, vol. 325, p. 433).*
Christian (Genetics, available online Jul. 26, 2008, vol. 186, p. 757-761).*
Li (Nature, Jul. 14, 2011, vol. 475, No. 7355, p. 217-221, plus Supplemental Material).*
High (Nature, 2005, vol. 435, p. 577 and 579).*
Jinek (eLife, Jan. 2013, p. 1-9).*
Holt (Nature Biotechnology, 2010, vol. 28, No. 8, 839-847).*
Supplemental Material for Mali (Science, Feb. 15, 2013, vol. 339, No. 6121, p. 823-826).*

(Continued)

*Primary Examiner* — Michael Wilson
(74) *Attorney, Agent, or Firm* — Lisa M. Warren, Esq.; Morse, Barnes-Brown & Pendleton, P.C.

(57) ABSTRACT

Disclosed herein are methods, compositions, and kits for high efficiency, site-specific genomic editing of cells.

12 Claims, 34 Drawing Sheets

(56) References Cited

U.S. PATENT DOCUMENTS

| | | |
|---|---|---|
| 2014/0273232 A1 | 9/2014 | Zhang et al. |
| 2014/0273233 A1 | 9/2014 | Chen et al. |
| 2014/0273234 A1 | 9/2014 | Zhang et al. |
| 2014/0287938 A1 | 9/2014 | Zhang et al. |
| 2014/0295556 A1 | 10/2014 | Joung et al. |
| 2014/0295557 A1 | 10/2014 | Joung et al. |
| 2014/0301990 A1 | 10/2014 | Gregory et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0335620 A1 | 11/2014 | Zhang et al. |
| 2014/0336133 A1 | 11/2014 | Miller et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0349405 A1 | 11/2014 | Sontheimer et al. |
| 2014/0356956 A1 | 12/2014 | Church et al. |
| 2014/0356958 A1 | 12/2014 | Mali et al. |
| 2014/0356959 A1 | 12/2014 | Church et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0031132 A1 | 1/2015 | Church et al. |
| 2015/0031133 A1 | 1/2015 | Church et al. |
| 2015/0031134 A1 | 1/2015 | Zhang et al. |
| 2015/0044191 A1 | 2/2015 | Liu et al. |
| 2015/0044192 A1 | 2/2015 | Liu et al. |
| 2015/0056705 A1 | 2/2015 | Conway et al. |
| 2015/0152436 A1 | 6/2015 | Musunuru et al. |
| 2015/0166969 A1 | 6/2015 | Takeuchi et al. |
| 2015/0176013 A1 | 6/2015 | Musunuru et al. |
| 2015/0344912 A1 | 12/2015 | Kim et al. |
| 2016/0024524 A1 | 1/2016 | Joung et al. |

FOREIGN PATENT DOCUMENTS

| | | |
|---|---|---|
| WO | 2014065596 A1 | 5/2014 |
| WO | WO 2014/093622 | 6/2014 |
| WO | WO 2014/150624 | 9/2014 |
| WO | WO 2014/151994 | 9/2014 |
| WO | WO 2014/153115 A2 | 9/2014 |
| WO | WO 2014/165825 | 10/2014 |
| WO | WO 2014/204726 A1 | 12/2014 |
| WO | WO 2015/006498 | 1/2015 |
| WO | WO 2016/057821 | 4/2016 |
| WO | WO 2016/057835 | 4/2016 |

OTHER PUBLICATIONS

Supplemental Material for Ding (Cell Stem Cell, Apr. 3, 2013, vol. 12, p. 393-394).*

Tebas (New England J. Med., Mar. 2014).*

Mandal (Cell Stem Cell, 2014, vol. 15, p. 643-652).*

Cho (Nature Biotech, 2013, Supplementary information).*

Cho, et al., "Targeted genome engineering in human celss with the Cas9 RNA-guided endonuclease," Nature Biotechnology 31(3): 230-232 (2013).

Cong, et al., "Multiplex Genome Engineering Using CRISPR/Cas Systems," Science 339: 819-823 (2013).

Jinek, et al., "RNA-programmed genome editing in human cells," eLife Research Article pp. 1-9 (2013).

Jinek, et al., "A programmable Dual-RNA-Guided DNA Endonuclease in Adaptive Bacterial Immunity," Science 337: 816-821 (2012).

Mali, et al., "RNA-Guided Human Genome Engineering via Cas9," Science 339: 823-826 (2013).

Ran, et al., "Double Nicking by RNA-Guided CRISPR Cas9 for Enhanced Genome Editing Specificity," Cell 154: 1380-1389 (2013).

Holt, et al., "Human hematopietic stem/progenitor cells modified by zinc-finger nucleases targeted to CCRG control HIV-1 in vivo," Nature biotechbology 28.8, 839-847 (2010).

Randau, "RNA processing in the minimal organism Nanoarchaeum equitans," Genome Biol 13.7 : 6 (2012).

Cho, et al., "Analysis of off-target effects of CRISPR/Cas-derived RNA-guided endonucleases and nickases," Genome Research (24): 132-141 (2014).

Cradick, et al., "CRISPR/Cas9 systems targeting B-globin and CCR5 genes have substantial off-target activity," Nucleic Acids Research, 1-9 (2013).

Hruscha, et al., "Efficient CRISPR/Cas9 genome editing with low off-target effects in zebrafish," Development (140):4982-4987 (2013).

Lin, et al., "CRISPR/Cas9 systems have off-target activity with insertions or deletions between target DNA and guide RNA sequences," Nucleic Acids Research 1-13 (2014).

Talkowski, et al., "Next-Generation Sequencing Strategies Enable Routine Detection of Balanced Chromosome Rearrangements for Clinical Diagnostics and Genetic Research," The American Journal of Human Genetics (88): 469-481 (2011).

International Search Report for International Application PCT/US2014/033082, dated Nov. 4, 2014.

Ding et al., "Enhanced Efficiency of Human Pluripotent Stem Cell Genome Editing through Replacing TALENs with CRISPRs," Cell Stem Cell, vol. 12, pp. 393-394 plus supplemental materials, 2013 (published online on Apr. 4, 2013).

Cong et al., "Multiplex Genome Engineering Using CRISPR/Cas Systems," Science, vol. 339, pp. 819-823 plus Supplementary Material, 2013 (published online on Jan. 3, 2013).

Mali et al., "RNA-Guided Human Genome Engineering via Cas9," Science, vol. 339, pp. 823-826 plus Supplementary Materials, 2013 (published online on Jan. 3, 2013).

Cho et al., "Targeted genome engineering in human cells with the Cas9 RNA-guided endonuclease," Nature Biotechnology, vol. 31(3), pp. 230-232, 2013 (published online on Jan. 29, 2013).

Cong,et al., "Multiplex genome engineering using CRISPR/Cas Systems," Science 21 339(6121): 819-823 (2013).

Gaj, et al., "ZFN, TALEN, and CRISPR/Cas-based methods for genome engineering," Trends in Biotechnology 31(7): 397-405 (2013).

GenBank~M13792.1 Human adenosine deaminase (ADA) gene, complete cds [online] Oct. 4, 1995 [retrieved Oct. 25, 2014]. Available on the internet: <URL: http://www.ncbi.nlm.nih.gov/nuccore/M13792>. Especially p. 17 n\35125-35147 and nt 35090-35112.

International Search Report for International Application PCT/US2014/46034, dated Jan. 23, 2015.

Chiba et al., "Genome Editing in Human Pluripotent Stem Cells Using Site-Specific Nucleases," *Methods in Molecular Biology*, 1239:267-280, (2015).

Cowan, "Human Cell-Based Models of Primary Adipocyte Disorders," *National Institutes of Health Grant No. 1R01DK095384-01* (Funding Start Date Apr. 1, 2012), Abstract.

Cowan, "Integrating Lipid Genotypes and Phenotypes in IPS Derived Hepatocytes/Adipocytes," *National Institutes of Health Grant No. 1U01HL107440-01* (Funding Start Date Jul. 5, 2011), Abstract.

Doudna et al., "The new frontier of genome engineering with CRISPR-Cas9," *Science*, 346(6213):1077, 1258096-1 through 1258096-9, (2014).

Gonzalez et al., "An iCRISPR Platform for Rapid, Multiplexable, and Inducible Genome Editing in Human Pluripotent Stem Cells," *Cell Stem Cell*, 15:215-226, (2014).

Hsu et al., "Development and Applications of CRISPR-Cas9 for Genome Engineering," *Cell*, 157:1262-1278, (2014).

Jun et al., "CRISPR/Cas: a novel way of RNA-guided genome editing," *Hereditas*, 35(11):1265-1273, (2013), English Abstract.

Kariko et al., "Incorporation of Pseudouridine Into mRNA Yields Superior Nonimmunogenic Vector With Increased Translational Capacity and Biological Stability," *Molecular Therapy*, 16(11):1833-1840, (2008).

Khalili et al., "Genome editing strategies: potential tools for eradicating HIV-1/AIDS," *J. Neurovirol*, 21(3):310-321, (2015).

(56) References Cited

OTHER PUBLICATIONS

Late Breaking Abstracts: Presented at the American Society of Gene & Cell Therapy's 16th Annual Meeting, May 15-18, 2013, Salt Lake City, Utah (56 pages).
Li et al., "MAGeCK enables robust identification of essential genes from genome-scale CRISPR/Cas9 knockout screens," *Genome Biology*, 15:1-12, (2014).
Lin et al., "Enhanced homology-directed human genome engineering by controlled timing of CRISPR/Cas9 delivery," *Elife, DOI*: 10.7554:1-13, (2014).
Lloyd et al., "Beyond the antigen receptor: editing the genome of T-Cells for cancer adoptive cellular therapies," *Frontiers in Immunology*, 4(22):1-7, (2013).
Merkle et al., "Modeling Human Disease with Pluripotent Stem Cells: from Genome Association to Function," *Cell Stem Cell*, 12:656-668, (2013).
Musunuru, "Genetic and Functional Analysis of a Novel Locus Associated with LDL-C and MI," *National Institutes of Health Grant No. 1K99HL098364-01*, (Funding Start Date May 3, 2010), Abstract.
Musunuru, "Stem Cell Models of Familial Combined Hypolipidemia," *National Institutes of Health Grant No. 1R01HL118744-01* (Funding Start Date Feb. 1, 2013), Abstract.
Pelletier et al., "Mouse Genome Engineering via CRISPR-Cas9 for Study of Immune Function," *Cell Press*, 42:18-27, (2015).
Shalem et al., "Genome-Scale CRISPR-Cas9 Knockout Screening in Human Cells," *Science*, 343:84-87, (2014).
Wang et al., "Genetic Screens in Human Cells Using the CRISPR-Cas9 System," *Science*, 343:80-84, (2014).
Wang etal., "One-Step Generation of Mice Carrying Mutations in Multiple Genes by CRISPR/Cas-Mediated Genome Engineering," *Cell*, 153:910-918, (2013).
Wu et al., "Target specificity of the CRISPR-Cas9 system," *Quantitative Biology*, 2(2):59-70, (2014).
Xie et al., "Seamless gene correction of β-thalassemia mutations in patient-specific iPSCs using CRISPR/Cas9 and piggyBac," *Genome Research*, 24:1526-1533, (2014).
Zhang et al., "CRISPR/Cas9 for genome editing: progress, implications and challenges," *HMG Advance Acess*, Published Mar. 20, 2014 pp. 1-21.
Non final Office Action U.S. Appl. No. 14/509,924, dated Jul. 29, 2016.
GenBank: AY136510.1, Kutlar, et al., "A new hemoglobin, beta chain variant 'Hb S-Wake' confirmed to be on the same chromosome with hemoglobin S mutation, detected in an African-American family," Retrieved from the internet on Dec. 23, 2015 < http://www.ncbi.nlm.nih.govlnucleotide/23268448?report=genbank&log$=nuclalign&blast_rank=2&RID=7NNHZVRH014>.
Ding, et al., "A TALEN genome editing system to generate human stem cell-based disease models," Cell Stem Cell 12(2): 238-251 (2013).
Schwank, et al., "Functional Repair of CFTR by CRISPR/Cas9 in Intestinal Stem Cell Organoids of Cystic Fibrosis Patients," Cell Stem Cell 13: 653-658 (2013).
Wiginton, et al., "Complete Sequence and Structure of the Gene for Human Adenosine Deaminase," Biochemistry 25(25): 8234-8244. Abstract (1986).
Rieder, et al., *Homo sapiens* Interleukin 2 Receptor, Gamma (Severe Combined Immunodeficiency) (IL2RG) Gene, Complete cds: GENBANK: AY692262.1. Jul. 21, 2004 [Retrieved on Mar. 3, 2016]. Retrieved from the Internet: <URL: http://www.ncbi.nlm.nih.gov/nucleotide/50897_469>; pp. 1-4.
Tasher, et al., "The Genetic Basis of Severe Combined Immunodeficiency and its Variants," The Application of Clinical Genetics 5: 67-80 (2012).
Woodbine, et al., "PRKDC Mutations in a SCID Patient with Profound Neurological Abnormalities." The Journal of Clinical Investigation 123(7): 2969-2980. (2013).
Kutlar, et al., A New Hemoglobin, Beta Chain Variant 'Hb S-Wake' Confirmed to be on the Same Chromosome with Hemoglobin S Mutation, Detected in an African-American Family: GENBANK: AY13651 0.1. Jul. 26, 2002 [Retrieved on Dec. 23, 2015]. Retrieved from the Internet: URL:http://www.ncbi.nlm.nih.qov/nucleotide/23268448.
Hendel, et al., "Quantifying Genome-Editing Outcomes at Endogenous Loci with SMRT Sequencing," Cell Reports 7: 293-305 (2014).
Lagresle-Peyrou, et al., "Human adenylate kinase 2 deficiency causes a profound haematopoietic defect associated with sensorineural deafness," Nat Genet 41(1): 106-111 (2009).
Third Party Observation for PCT Application PCT/US2014/033082, made/submitted Aug. 3, 2015.
International Search Report for International Application PCT/US2015/054762, dated Mar. 11, 2016.
International Search Report for International Application PCT/US2015/054747, dated Apr. 29, 2016.
Non-Final Office Action for U.S. Appl. No. 14/509,787, dated Apr. 11, 2016.
Edelstein, et al., "Gene therapy clinical trials worldwide," *J Gene Med 6*: 597-602, (2004).
GenBank EF150856.1, Kutlar, et al., "*Homo sapiens* beta-globin (HBB) gene, HBB-hb sickle-Monroe allele, exons 1, 2 and partial cds," (Nov. 28, 2006).
Johnson-Saliba, et al., "Gene Therapy: Optimising DNA Delivery to the Nucleus," *Current Drug Targets*, 2: 371-399, (2001).
Luo, et al., "Synthetic DNA delivery systems," *Nature Biotech.*, 18: 33-37, (2000).
Palu, et al., "In pursuit of new developments for gene therapy of human diseases," *J. Biotec.*, 68: 1-13, (1999).
Pfeifer, et al., "Gene Therapy: Promises and Problems," *Annu. Rev. Genomics Hum. Genet.*, 2: 177-211, (2001).
Shoji, et al., "Current Status of Delivery Systems to Improve Target Efficacy of Oligonucleotides," *Current Pharm. Design*, 10: 785-796, (2004).
Hwang, et al., "Efficient Genome Editing in Zebrafish Using a CRISPR-Cas System," *Nature Biotechnology*, 31(3):227-229, (Mar. 2013).
Jiang, et al., "RNA-Guided Editing of Bacterial Genomes Using CRISPR-Cas Systems," *Nature Biotechnology*, 31(3):233-239, (Mar. 2013).
Mandal, et al., "Reprogramming Human Fibroblasts to Pluripotency Using Modified mRNA," *Nature Protocols*, 8(3):568-582, (2013).
Ramalingam, et al., "A CRISPR Way to Engineer the Human Genome," *Genome Biology*, 14(107):1-4, (2013).
Shen, et al., "Generation of Gene-Modified Mice via Cas9/RNA-Mediated Gene Targeting," *Cell Research*, 23:720-723, (2013).
Wilen, et al., "Engineering HIV-Resistant Human CD4+ T Cells With CXCR4-Specific Zinc-Finger Nucleases," *PLoS Pathogens*, 7(4):1-15, (Apr. 2011).
Extended European Search Report from European Application 14779492.9, dated Dec. 20, 2016.
Extended European Search Report from European Application 14822545.1, dated Nov. 22, 2016.
Smithies, et al., "Insertion of DNA Sequences Into the Human Chromosomal β-Globin Locus by Homologous Recombination," Nature, 317(19):230-234, (Sep. 1985).
Final Office Action for U.S. Appl. No. 14/509,787, dated Dec. 2, 2016.
Final Office Action for U.S. Appl. No. 14/509,924, dated Feb. 14, 2017.

\* cited by examiner

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46414444 | 46414445 |  | 1 | 50 (SEQ ID NO: 1) TGACATCAATTATTATACATGG |  | 1 | 4 | 26 |
| (N20)NGG | 46414510 | 46414511 |  | 1 | 116 (SEQ ID NO: 2) CCTGCCTCCGCTCTACTCACTGG |  | 2 | 2 | 25 |
| (N20)NGG | 46414523 | 46414524 |  | 1 | 129 (SEQ ID NO: 3) TACTCACTGGTGTTCATCTTGG |  | 2 | 3 | 29 |
| (N20)NGG | 46414531 | 46414532 |  | 1 | 137 (SEQ ID NO: 4) GGTGTTCATCTTTGGTTTTGTGG |  | 2 | 2 | 34 |
| (N20)NGG | 46414532 | 46414533 |  | 1 | 138 (SEQ ID NO: 5) GTGTTCATCTTTGGTTTTGTGG |  | 2 | 2 | 64 |
| (N20)NGG | 46414543 | 46414544 |  | 1 | 149 (SEQ ID NO: 6) TGGTTTTGTGGCAACATGCTGG |  | 2 | 4 | 32 |
| (N20)NGG | 46414572 | 46414573 |  | 1 | 178 (SEQ ID NO: 7) TCATCCGATAAACTGCAAAAGG |  | 1 | 1 | 35 |
| (N20)NGG | 46414609 | 46414610 |  | 1 | 215 (SEQ ID NO: 8) TGACATCTACTTGTCGCAACTGG |  | 2 | 2 | 37 |
| (N20)NGG | 46414650 | 46414651 |  | 1 | 256 (SEQ ID NO: 9) CCTTCTTTACTGTGCCCTTCTGG |  | 1 | 1 | 35 |
| (N20)NGG | 46414651 | 46414652 |  | 1 | 257 (SEQ ID NO: 10) CTCACTATGCTGCCGCCCAGTGG |  | 2 | 3 | 44 |
| (N20)NGG | 46414674 | 46414675 |  | 1 | 280 (SEQ ID NO: 11) TCACTATGCTGCCGCCGCAGTGG |  | 1 | 2 | 16 |
| (N20)NGG | 46414675 | 46414676 |  | 1 | 281 (SEQ ID NO: 12) GCTGCCGCCCAGTGGGACTTGG |  | 1 | 1 | 7 |
| (N20)NGG | 46414682 | 46414683 |  | 1 | 288 (SEQ ID NO: 13) ACAATGTCAACTCTTGACAGG |  | 1 | 2 | 10 |
| (N20)NGG | 46414709 | 46414710 |  | 1 | 315 (SEQ ID NO: 14) CAATGTCAACTCTTGACAGG |  | 1 | 1 | 6 |
| (N20)NGG | 46414710 | 46414711 |  | 1 | 316 (SEQ ID NO: 15) |  | 1 | 2 | 11 |

FIG. 1

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46414724 | 46414725 | | 1 | 336: TTGACAGGGCTCTATTTATAGG (SEQ ID NO: 16) | | 1 | 12 |
| (N20)NGG | 46414736 | 46414737 | | 1 | 342: TATTTATAGGCTTCTCTCTGG (SEQ ID NO: 17) | 1 | | 31 |
| (N20)NGG | 46414770 | 46414771 | | 1 | 376: TCATCCTCCTGACAATCGATAGG (SEQ ID NO: 18) | | 2 | 7 |
| (N20)NGG | 46414777 | 46414778 | | 1 | 383: CCTGACAATCGATAGGTACCTGG (SEQ ID NO: 19) | 2 | | 4 |
| (N20)NGG | 46414812 | 46414813 | | 1 | 418: CTGTGTTTGCTTTAAAAGCCAGG (SEQ ID NO: 20) | 2 | 2 | 36 |
| (N20)NGG | 46414816 | 46414817 | | 1 | 422: GTTTGCTTTAAAAGCCAGGACGG (SEQ ID NO: 21) | 2 | 2 | 30 |
| (N20)NGG | 46414826 | 46414827 | | 1 | 432: AAAGCCAGGACGGTCACTTTGG (SEQ ID NO: 22) | 2 | 3 | 16 |
| (N20)NGG | 46414827 | 46414828 | | 1 | 433: AAGCCAGGACGGTCACTTTGGG (SEQ ID NO: 23) | 2 | 2 | 10 |
| (N20)NGG | 46414828 | 46414829 | | 1 | 434: AGCCAGGACGGTCACTTTGGGG (SEQ ID NO: 24) | 2 | 4 | 10 |
| (N20)NGG | 46414831 | 46414832 | | 1 | 437: CAGGACGGTCACTTTGGGGTGG (SEQ ID NO: 25) | 2 | 2 | 10 |
| (N20)NGG | 46414851 | 46414852 | | 1 | 457: TGGTGACAAGTGTGATCACTTGG (SEQ ID NO: 26) | 2 | 2 | 33 |
| (N20)NGG | 46414852 | 46414853 | | 1 | 458: GGTGACAAGTGTGATCACTTGGG (SEQ ID NO: 27) | 1 | 2 | 30 |
| (N20)NGG | 46414855 | 46414856 | | 1 | 461: GACAAGTGTGATCACTTGGGTGG (SEQ ID NO: 28) | 1 | 1 | 11 |
| (N20)NGG | 46414858 | 46414859 | | 1 | 464: AAGTGTGATCACTTGGGTGGTGG (SEQ ID NO: 29) | 1 | | 30 |
| (N20)NGG | 46414880 | 46414881 | | 1 | 486: GCTGTGTTTGCGTCTCTCCCAGG (SEQ ID NO: 30) | 1 | 4 | 22 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46414910 | 46414911 | 1 | 1 | TTTACAGATCTCAAAAAGAAGG 516 (SEQ ID NO: 31) | | 1 | 3 | 27 |
| (N20)NGG | 46414962 | 46414983 | 1 | 1 | CATACAGTCAGTATCAATTCTGG 569 (SEQ ID NO: 32) | | | 3 | 16 |
| (N20)NGG | 46414996 | 46414997 | 1 | 1 | GACATTAAAGATAGTCATCTTGGG 602 (SEQ ID NO: 33) | | 1 | 3 | 31 |
| (N20)NGG | 46414997 | 46414998 | 1 | 1 | ACATTAAAGATAGTCATCTTGGGG 603 (SEQ ID NO: 34) | | | 2 | 25 |
| (N20)NGG | 46414998 | 46414999 | 1 | 1 | CATTAAAGATAGTCATCTTGGGG 604 (SEQ ID NO: 35) | | 1 | 1 | 26 |
| (N20)NGG | 46415002 | 46415003 | 1 | 1 | AAAGATAGTCATCTTGGGGCTGG 608 (SEQ ID NO: 36) | | 1 | 1 | 30 |
| (N20)NGG | 46415023 | 46415024 | 1 | 1 | GGTCCTGCGCGCTGCTTGTCATGG 629 (SEQ ID NO: 37) | | 1 | 4 | 21 |
| (N20)NGG | 46415038 | 46415039 | 1 | 1 | TGTCATGGTCATCTGCTACTGGG 644 (SEQ ID NO: 38) | | 1 | 2 | 18 |
| (N20)NGG | 46415039 | 46415040 | 1 | 1 | GTCATGGTCATTGCTACTGGGG 645 (SEQ ID NO: 39) | | 2 | 4 | 17 |
| (N20)NGG | 46415061 | 46415062 | 1 | 1 | CAATCCTAAAAACTTCGTTCGG 667 (SEQ ID NO: 40) | | 1 | 4 | 26 |
| (N20)NGG | 46415082 | 46415083 | 1 | 1 | GGTGTCGAAATGAAGAAGAAGAG 688 (SEQ ID NO: 41) | | 2 | 3 | 22 |
| (N20)NGG | 46415088 | 46415089 | 1 | 1 | GAAATGAAGAAGAAGGCACAG 694 (SEQ ID NO: 42) | | 1 | 7 | 81 |
| (N20)NGG | 46415089 | 46415090 | 1 | 1 | AAATGAAGAAGAAGGCACAGG 695 (SEQ ID NO: 43) | | | 8 | 109 |
| (N20)NGG | 46415097 | 46415098 | 1 | 1 | AGAAGAAGCACAGGCTGTGAG 703 (SEQ ID NO: 44) | | 1 | 3 | 70 |
| (N20)NGG | 46415136 | 46415137 | 1 | 1 | TGATTGTTTATTTTCTCTCTGG 742 (SEQ ID NO: 45) | | 2 | 10 | 122 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46415137 | 46415138 | | | 743 (SEQ ID NO: 46) GATTGTTTATTTTCTTTCTTGAGG | | 7 | 142 |
| (N20)NGG | 46415176 | 46415177 | | 1 | 782 (SEQ ID NO: 47) CCTTCTCCTGAACACCTTCCAGG | 2 | 3 | 32 |
| (N20)NGG | 46415186 | 46415187 | | 1 | 792 (SEQ ID NO: 48) AACACCTTCCAGGAATTCTTTGG | 2 | 2 | 32 |
| (N20)NGG | 46415214 | 46415215 | | 1 | 820 (SEQ ID NO: 49) ATAATTGCAGTAGCTCTAACAGG | 1 | 1 | 15 |
| (N20)NGG | 46415218 | 46415219 | | 1 | 824 (SEQ ID NO: 50) TTCCAGTAGCTCTAACAAGGTTGG | 1 | 2 | 12 |
| (N20)NGG | 46415233 | 46415234 | | 1 | 839 (SEQ ID NO: 51) CAGGTTGGACCAAGCTATGCAGG | 1 | 1 | 14 |
| (N20)NGG | 46415249 | 46415250 | | 1 | 855 (SEQ ID NO: 52) ATGCAGGTGACAGAGACTCTTGG | 2 | 2 | 24 |
| (N20)NGG | 46415250 | 46415251 | | 1 | 856 (SEQ ID NO: 53) TGCAAGGTGACAGAGACTCTTGGG | 2 | 5 | 30 |
| (N20)NGG | 46415294 | 46415295 | | 1 | 900 (SEQ ID NO: 54) CCGATCATCTATGCCTTTGTCGG | 2 | 3 | 19 |
| (N20)NGG | 46415295 | 46415296 | | 1 | 901 (SEQ ID NO: 55) CGATCATCTATGCCTTTGTCGGG | 1 | 4 | 16 |
| (N20)NGG | 46415296 | 46415297 | | 1 | 902 (SEQ ID NO: 56) CTGTTCTATTTTCCAGACAAGAGG | | 3 | 9 |
| (N20)NGG | 46415383 | 46415384 | | 1 | 989 (SEQ ID NO: 57) TCAGTTTACACCCGATCCACTGG | 1 | 1 | 24 |
| (N20)NGG | 46415423 | 46415424 | | 1 | 1029 (SEQ ID NO: 58) CAGTTTACACCCGATCCACTGGG | | 2 | 2 |
| (N20)NGG | 46415424 | 46415425 | | 1 | 1030 (SEQ ID NO: 59) AGTTTACACCCGATCCACTGGGG | 1 | 1 | 3 |
| (N20)NGG | 46415425 | 46415426 | | 1 | 1031 (SEQ ID NO: 60) | | 1 | 3 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46415431 | 46415453 | | 1 | 1037:G (SEQ ID NO: 61) CACCCGATCCACTGGGGAGCAG | | 1 | 19 |
| (N20)NGG | 46415443 | 46415444 | | 1 | 1049 (SEQ ID NO: 62) TGGGGAGCAGGAAATATCTGTGG | | 1 | 34 |
| (N20)NGG | 46415244 | 46415445 | | 1 | 1050:G (SEQ ID NO: 63) GGGGAGCAGGAAATATCTGTGG | | 1 | 31 |
| (N20)NGG | 46414414 | 46414415 | | -1 | 20 (SEQ ID NO: 64) TAATAATTGATGTCATACATTGG | | 1 | 38 |
| (N20)NGG | 46414447 | 46414448 | | -1 | 53 (SEQ ID NO: 65) TTCACATTGATTTTTGGCAGGG | | 1 | 5 | 40 |
| (N20)NGG | 46414448 | 46414449 | | -1 | 54 (SEQ ID NO: 66) CTTCACATTGATTTTTGGCAGG | | 1 | 1 | 28 |
| (N20)NGG | 46414452 | 46414453 | | -1 | 58 (SEQ ID NO: 67) TTTTGCTTCACATTGATTTTTGG | | 2 | 3 | 79 |
| (N20)NGG | 46414481 | 46414482 | | -1 | 87:G (SEQ ID NO: 68) GTAGAGCCGGAGGCAGGAGCCGG | | 1 | 7 | 89 |
| (N20)NGG | 46414482 | 46414483 | | -1 | 88:G (SEQ ID NO: 69) AGTAGAGCCGAGGCAGGAGCCG | | 3 | 6 | 72 |
| (N20)NGG | 46414485 | 46414486 | | -1 | 91:G (SEQ ID NO: 70) GTGAAGTAGAAGCCGAAGGCAGGAG | | 1 | 2 | 44 |
| (N20)NGG | 46414488 | 46414489 | | -1 | 94:G (SEQ ID NO: 71) CCCAGTGAGTAGAGCCGGAGGCAG | | 2 | 3 | 19 |
| (N20)NGG | 46414492 | 46414493 | | -1 | 98:G (SEQ ID NO: 72) AACACCAGTGAGTAGAGCCGGAG | | 2 | 4 | 14 |
| (N20)NGG | 46414495 | 46414496 | | -1 | 101 (SEQ ID NO: 73) ATGAACACCAGTGAGTAGAGCCGG | | 2 | 3 | 21 |
| (N20)NGG | 46414548 | 46414549 | | -1 | 154 (SEQ ID NO: 74) TTTTGCAGTTTATCAGGATGATGG | | 1 | 4 | 33 |
| (N20)NGG | 46414554 | 46414555 | | -1 | 160 (SEQ ID NO: 75) TCACCGTTTTGCAGTTTATCAGG | | 1 | 1 | 26 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46414596 | 46414597 | -1 | 202 | GCAAGAATGGCLAGGTTGAGCAG (SEQ ID NO: 76) | | 2 | 67 |
| (N20)NGG | 46414605 | 46414606 | -1 | 211 | AAACAAGTCAGAGAATGGCCAG (SEQ ID NO: 77) | | 1 | 88 |
| (N20)NGG | 46414610 | 46414611 | -1 | 216 | AATCAAAAACAAGTCAGAGATGG (SEQ ID NO: 78) | | 1 | 123 |
| (N20)NGG | 46414620 | 46414621 | -1 | 226 | GGACAGTAAGAAGAAAAAACAG (SEQ ID NO: 79) | | 1 | 97 |
| (N20)NGG | 46414629 | 46414630 | -1 | 235 | CCCAGAAGGGGACAGTAAGAAG (SEQ ID NO: 80) | | 2 | 38 |
| (N20)NGG | 46414641 | 46414642 | -1 | 247 | CAGCATAGTTGAGCCCAGAAGG (SEQ ID NO: 81) | | 1 | 41 |
| (N20)NGG | 46414642 | 46414643 | -1 | 248 | GGCAGCATAGTTGAGCCCAGAAG (SEQ ID NO: 82) | | 1 | 30 |
| (N20)NGG | 46414643 | 46414644 | -1 | 249 | ATTTCAAAAGTCCCACTGGCGG (SEQ ID NO: 83) | | 1 | 31 |
| (N20)NGG | 46414664 | 46414665 | -1 | 270 | TGTATTCCAAAGTCCCACTGGG (SEQ ID NO: 84) | | 1 | 23 |
| (N20)NGG | 46414667 | 46414668 | -1 | 273 | TTGTATTTCCAAAGTCCCACTGG (SEQ ID NO: 85) | | 1 | 22 |
| (N20)NGG | 46414668 | 46414669 | -1 | 274 | GGTACCTATCGATTGTCAGGAGG (SEQ ID NO: 86) | | 1 | 23 |
| (N20)NGG | 46414752 | 46414753 | -1 | 358 | CTAGGTACCTATCGATTGTCAGG (SEQ ID NO: 87) | | 2 | 5 |
| (N20)NGG | 46414755 | 46414756 | -1 | 361 | ACACAGGCATGGCACGACAGCCAG (SEQ ID NO: 88) | | 2 | 5 |
| (N20)NGG | 46414773 | 46414774 | -1 | 379 | CTTTAAGCAAACACAGCATGG (SEQ ID NO: 89) | | 1 | 30 |
| (N20)NGG | 46414785 | 46414786 | -1 | 391 | (SEQ ID NO: 90) | | 3 | 62 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46414818 | 46414838 | | -1 | 414 CACCCAAAGGTGACCGTCCTGG (SEQ ID NO: 91) | | | 9 |
| (N20)NGG | 46414820 | 46414821 | | -1 | 428 CACACTGTCACCACCCCAAAGG (SEQ ID NO: 92) | | 2 | 19 |
| (N20)NGG | 46414875 | 46414876 | | -1 | 481 ATCTGGTAAAGATGATTCCTGGG (SEQ ID NO: 93) | | 2 | 29 |
| (N20)NGG | 46414876 | 46414877 | | -1 | 482 GATCTGGTAAAGATGATTCCTGG (SEQ ID NO: 94) | | 1 | 22 |
| (N20)NGG | 46414892 | 46414893 | | -1 | 498 AAGACCTTCTTTTCGAGAATCGG (SEQ ID NO: 95) | | 1 | 35 |
| (N20)NGG | 46414922 | 46414923 | | -1 | 528 GTATGGAAAATGAGAAGCTGCAGG (SEQ ID NO: 96) | | 1 | 4 | 23 |
| (N20)NGG | 46414939 | 46414940 | | -1 | 545 CAGAATTGATACTGACTGTATGG (SEQ ID NO: 97) | | 1 | 2 | 11 |
| (N20)NGG | 46414971 | 46414972 | | -1 | 577 AGATGACTATCTTTAATGTCTGG (SEQ ID NO: 98) | | 1 | 5 | 25 |
| (N20)NGG | 46415004 | 46415005 | | -1 | 610 TGGACCATGACAAGCAGGGGCAG (SEQ ID NO: 99) | | 1 | 2 | 9 |
| (N20)NGG | 46415008 | 46415009 | | -1 | 614 CAGGATGACCATGACAAGCAGGCGG (SEQ ID NO: 100) | | 1 | 3 | 22 |
| (N20)NGG | 46415043 | 46415044 | | -1 | 649 GACACCGAAGGAGAGTTTTAGG (SEQ ID NO: 101) | | 1 | 2 | 14 |
| (N20)NGG | 46415108 | 46415109 | | -1 | 714 GAGAAAATAAACAATCATGATGG (SEQ ID NO: 102) | | 2 | 9 | 66 |
| (N20)NGG | 46415140 | 46415141 | | -1 | 746 AGGAGGAAGGACAATGTTTTAGGG (SEQ ID NO: 103) | | 1 | 1 | 31 |
| (N20)NGG | 46415142 | 46415142 | | -1 | 747 CAGGAGAAGGACAATGTTGTAGG (SEQ ID NO: 104) | | 1 | 2 | 34 |
| (N20)NGG | 46415154 | 46415155 | | -1 | 760 CTTCGAAGTGTTCAGGAGAAG (SEQ ID NO: 105) | | 2 | 6 | 38 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46415160 | 46415163 | | -1 | AGAATTCCTGGAAGGTGTTCAGG (SEQ ID NO: 106) | | 2 | 19 |
| (N20)NGG | 46415168 | 46415169 | | -1 | CAGGCCAAAGAATTCCTGGAAGG (SEQ ID NO: 107) | | 2 | 32 |
| (N20)NGG | 46415172 | 46415173 | | -1 | TATTCAGGCCAAAGAATTCCTGG (SEQ ID NO: 108) | | 1 | 15 |
| (N20)NGG | 46415187 | 46415188 | | -1 | TAGAGCTACTGCAATTATTCAGG (SEQ ID NO: 109) | | 1 | 28 |
| (N20)NGG | 46415220 | 46415221 | | -1 | TCTCTGTCACCTGCATAGCTTGG (SEQ ID NO: 110) | | 1 | 124 |
| (N20)NGG | 46415271 | 46415272 | | -1 | CGACAAAGGCATAGATGATGAGG (SEQ ID NO: 111) | | 1 | 13 |
| (N20)NGG | 46415272 | 46415273 | | -1 | CCGACAAAGGCATAGATGATGG (SEQ ID NO: 112) | | 1 | 7 |
| (N20)NGG | 46415273 | 46415274 | | -1 | CCCGACAAAGGCATAGATGATGG (SEQ ID NO: 113) | | 1 | 7 |
| (N20)NGG | 46415265 | 46415266 | | -1 | TCTGAATTCTCCCCGACAAAGG (SEQ ID NO: 114) | | 1 | 8 |
| (N20)NGG | 46415313 | 46415314 | | -1 | GCTTTTGGAAGAAGACTAAGAGG (SEQ ID NO: 115) | | 1 | 60 |
| (N20)NGG | 46415328 | 46415329 | | -1 | AGKGTTTGGCAATGTGCTTTGG (SEQ ID NO: 116) | | 2 | 11 |
| (N20)NGG | 46415342 | 46415343 | | -1 | ACAGCATTTGCAGAAGCGTTTGG (SEQ ID NO: 117) | | 1 | 18 |
| (N20)NGG | 46415373 | 46415374 | | -1 | CTCGCTCGGGAGCCTCTTTGCTGG (SEQ ID NO: 118) | | 1 | 6 |
| (N20)NGG | 46415386 | 46415387 | | -1 | TAAACTGAGCTTGCTCGCTCGGG (SEQ ID NO: 119) | | 1 | 6 |
| (N20)NGG | 46415387 | 46415388 | | -1 | GTAAACTGAGCTTGCTCGCTCGG (SEQ ID NO: 120) | 1 | 2 | 5 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 46415411 | 46415412 | | -2 | 1017 TTCCTGCTCCCAGTGGATCGGG (SEQ ID NO: 121) | | 3 | 39 |
| (N20)NGG | 46415412 | 46415413 | | -1 | 1018 TTTCCTGCTCCCAGTGGATCGG (SEQ ID NO: 122) | 1 | 5 | 30 |
| (N20)NGG (N21)NNAG | 46415417 | 46415418 | | -1 | 1023 AGATATTTCCTGCTCCCAGTGG (SEQ ID NO: 123) | 1 | 1 | 39 |
| AAW (N21)NNAG | 46414903 | 46414910 | | 1 | 513 ATCATCTTTACCAGATCTCAAAAA GMAG (SEQ ID NO: 124) | 1 | 1 | 2 |
| AAW (N21)NNAG | 46415076 | 46415077 | | 1 | 684 AACCTTGCTTCGGTGTCGAAATG AGAAG (SEQ ID NO: 125) | 2 | 2 | 2 |
| AAW (N21)NNAG | 46415079 | 46415080 | | 1 | 685 TCTGCTTCTGGTGTCGAAATGAGA AGAAG (SEQ ID NO: 126) | 1 | 2 | 2 |
| AAW (N21)NNAG | 46415301 | 46415302 | | 1 | 907 CATCATCTATGCCCTTTGTCGGGG AGAAG (SEQ ID NO: 127) | 1 | 1 | 2 |
| AAW (N21)NNAG | 46415309 | 46415310 | | 1 | 915 ATGCCTTTGTCGGGAGGAAGTTC AGAAA (SEQ ID NO: 128) | 1 | 1 | 3 |
| AAW BTTCTNR(N 2) | 46414630 | 46414631 | | 1 | 236 AGTGAGTCCAAGAAGGAGACAGT CTGGGCTGCAGTATAGTGAGCC (SEQ ID NO: 129) | 1 | 1 | 2 |
| BTTCTNR(N 2) | 46414644 | 46414645 | | 1 | 250 CAGAAG (SEQ ID NO: 130) GATGATGAAGAAGAATTCCAGAGA | 1 | 1 | 1 |
| BTTCTNR(N 2) | 46414725 | 46414726 | | -1 | 331 AGAAG (SEQ ID NO: 131) GAGCATGATGAAGAAGAATTCCAG | 1 | 1 | 3 |
| BTTCTNR(N 2) | 46414728 | 46414729 | | -1 | 334 AGAAG (SEQ ID NO: 132) ATCGATTGTCAGGAAGATGATGA | 1 | 1 | 5 |
| BTTCTNR(N 2) | 46414740 | 46414741 | | -1 | 346 AGAAG (SEQ ID NO: 133) CAATGTTGTAGGGAGCCCAGAAG | | 2 | 2 |
| BTTCTNR(N 2) | 46415125 | 46415126 | | -1 | 731 AGAAA (SEQ ID NO: 134) AAGGACAATGTTGTAGGGAGCCC | 1 | | 4 |
| BTTCTNR(N 2) | 46415130 | 46415131 | | -1 | 736 AGAAG (SEQ ID NO: 135) | | 1 | 2 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| BTTCTNN(N 21) | 46415155 | 46415198 | -1 | 761 | AGAATTCCTGGAAGGTGTTCAGG AGAAG (SEQ ID NO: 136) | | 2 | 2 |
| BTTCTNN(N 21) | 46415322 | 46415323 | -1 | 928 | GCGTTTGGCAATGTGCTTTTGGA AGAAG (SEQ ID NO: 137) | | 1 | 1 |
| BTTCTNN(N 21) | 46415349 | 46415350 | -1 | 955 | CTGGAAAATAGAACASCATTGC AGAAG (SEQ ID NO: 138) | 1 | 1 | 5 |
| BTTCTNN(N 21) | 46415363 | 46415364 | -1 | 969 | TCTGGAGCCTCTTGCTGGAAAAT AGAAC (SEQ ID NO: 139) | 1 | 1 | 1 |

FIG. 1 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 136872475 | 136872476 | | 1 | ACTTGAAGACTCAGAACTCAGTGG (SEQ ID NO: 140) | | 1 | 24 |
| (N20)NGG | 136872508 | 136872509 | | 1 | ATGTCCACCTCGCTTTCCTTTGG (SEQ ID NO: 141) | | 1 | 12 |
| (N20)NGG | 136872513 | 136872514 | | 1 | CACCTGCTTTCCTTTGGAGAAGG (SEQ ID NO: 142) | | | 12 |
| (N20)NGG | 136872522 | 136872523 | | 1 | TTCCTTTGGAGAAGGATCTTGAGG (SEQ ID NO: 143) | | 1 | 33 |
| (N20)NGG | 136872526 | 136872527 | | 1 | TTTGGAGAAGGATCTTGAGGCTGG (SEQ ID NO: 144) | | 1 | 16 |
| (N20)NGG | 136872544 | 136872545 | | 1 | GCTGGACCCTCGCTCAGAGAGG (SEQ ID NO: 145) | | 1 | 38 |
| (N20)NGG | 136872558 | 136872559 | | 1 | TCAGAGAAGGTGAGTGGCGTGCTGG (SEQ ID NO: 146) | | 1 | 38 |
| (N20)NGG | 136872559 | 136872560 | | 1 | CACAGAGGTGAGTGCGTGCTGGG (SEQ ID NO: 147) | | 1 | 26 |
| (N20)NGG | 136872565 | 136872566 | | 1 | GGTGAGTGCGTGCTGGCAGAAGG (SEQ ID NO: 148) | | 1 | 50 |
| (N20)NGG | 136872577 | 136872578 | | 1 | TTGGCAGAAGGTTTTAAATTTGG (SEQ ID NO: 149) | | 1 | 47 |
| (N20)NGG | 136872585 | 136872586 | | 3 | AGGTTTTAAATTTGGCTCCAAGG (SEQ ID NO: 150) | | 1 | 33 |
| (N20)NGG | 136872587 | 136872588 | | 3 | TGGCTCCAAGGAAAGCATAGAAGG (SEQ ID NO: 151) | | 1 | 38 |
| (N20)NGG | 136872601 | 136872602 | | 1 | TCAAGGAAAGCATAGAGGATGG (SEQ ID NO: 152) | | 1 | 45 |
| (N20)NGG | 136872602 | 136872603 | | 1 | CCAAGGAAAGCATAGAGGATGGG (SEQ ID NO: 153) | | 1 | 31 |

FIG. 2

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| [N20]NGG | 136872603 | 136872603 | 1 | | CAAGAAAGCATAGAAGGATGAGGG (SEQ ID NO: 154) | 1 | 3 | 59 |
| [N20]NGG | 136872618 | 136872619 | 1 | | GGATGGGGTTCAGGACAACAGTGG (SEQ ID NO: 155) | 1 | 2 | 16 |
| [N20]NGG | 136872630 | 136872631 | 1 | | GACAACAGTGGAAGAAAGCTAGG (SEQ ID NO: 156) | 2 | 6 | 101 |
| [N20]NGG | 136872631 | 136872632 | 1 | | ACAACAGTGGAAGAAAGCTAGGG (SEQ ID NO: 157) | 2 | 1 | 24 |
| [N20]NGG | 136872637 | 136872638 | 1 | | GTGGAAGAAAGCTAGGGCCTCGG (SEQ ID NO: 158) | 1 | 3 | 37 |
| [N20]NGG | 136872643 | 136872644 | 1 | | GAAAGCTAGGGCCTCGGTGATGG (SEQ ID NO: 159) | 1 | 1 | 9 |
| [N20]NGG | 136872699 | 136872700 | 1 | | ACCCTTGCTTGATGATTCCAGG (SEQ ID NO: 160) | 1 | 2 | 10 |
| [N20]NGG | 136872702 | 136872703 | 1 | | CTTGCTTGATGATTCCAGGAGG (SEQ ID NO: 161) | 2 | 3 | 26 |
| [N20]NGG | 136872709 | 136872710 | 1 | | GATGATTCCAGGAGGATGAAGG (SEQ ID NO: 162) | 1 | 29 | 73 |
| [N20]NGG | 136872737 | 136872738 | 1 | | ATGCTGATCCAATGTAGTAAGG (SEQ ID NO: 163) | 1 | 2 | 7 |
| [N20]NGG | 136872748 | 136872749 | 1 | | AATGTAGTAAGGCAGGCAACAGG (SEQ ID NO: 164) | 1 | 1 | 39 |
| [N20]NGG | 136872762 | 136872763 | 1 | | GCCACAGGCGAAGAAAGCTAAGG (SEQ ID NO: 165) | 1 | 1 | 5 |
| [N20]NGG | 136872768 | 136872769 | 1 | | AGCCGAAGAAAGCCAGGATGAAGG (SEQ ID NO: 166) | 2 | 4 | 58 |
| [N20]NGG | 136872778 | 136872779 | 1 | | AGCCAGGATGAGGATGACTGTGG (SEQ ID NO: 167) | 1 | 4 | 38 |

FIG. 2 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| {N20}NGG | 136872786 | 136872787 | 1 | 723 | TGAGGATGAACTGTCTTGGTCTTGAGG (SEQ ID NO: 168) | | 1 | 34 |
| {N20}AGG | 136872767 | 136872788 | 1 | 722 | GAGGATGACTGTGGTCTTGAGGAG (SEQ ID NO: 169) | | 1 | 30 |
| {N20}NGG | 136872801 | 136872802 | 1 | 708 | TCTTGAAGGCCTTGCGCTTCTGG (SEQ ID NO: 170) | 1 | | 3 |
| {N20}NGG | 136872804 | 136872805 | 1 | 705 | TGAGGGCCTTGCGCTTCTGGTGG (SEQ ID NO: 171) | | 2 | 12 |
| {N20}NGG | 136872811 | 136872812 | 1 | 698 | CTTGCGCTTCTGGTGGCCTTGG (SEQ ID NO: 172) | | 1 | 23 |
| {N20}NGG | 136872826 | 136872827 | 1 | 683 | GCCCTTGGAGTGTGACAAGCTGG (SEQ ID NO: 173) | 1 | 1 | 17 |
| {N20}NGG | 136872827 | 136872848 | 1 | 682 | GGAGATGATAATCAAGGACAGG (SEQ ID NO: 174) | 1 | 4 | 36 |
| {N20}NGG | 136872852 | 136872853 | 1 | 657 | TGATAATGLAATGGCAGGAGAGG (SEQ ID NO: 175) | 1 | 1 | 26 |
| {N20}NGG | 136872866 | 136872867 | 1 | 643 | CAGGACAAGGATGACAATACCAGG (SEQ ID NO: 176) | 1 | 1 | 15 |
| {N20}NGG | 136872870 | 136872871 | 1 | 639 | ACAGGATGACAATACCAGGCAGG (SEQ ID NO: 177) | 1 | 1 | 16 |
| {N20}NGG | 136872876 | 136872877 | 1 | 633 | TGACAATACCAGGCAGGATAAGG (SEQ ID NO: 178) | 1 | 3 | 17 |
| {N20}AGG | 136872900 | 136872901 | 1 | 609 | CAAGCATGATGTGCTGAAACTGG (SEQ ID NO: 179) | | 2 | 13 |
| {N20}NGG | 136872925 | 136872926 | 1 | 584 | CACAACCACCAAGTCATTGG (SEQ ID NO: 180) | 1 | 2 | 23 |
| {N20}NGG | 136872926 | 136872927 | 1 | 583 | ACAACCACCACAAGTCATTGGG (SEQ ID NO: 181) | | 2 | 14 |

FIG. 2 cont.

| site_type | site_start | site_end | sgR_strand | relative_start | site_sequence | genome wide hits with 1 mismatches | genome wide hits with 2 mismatches | genome wide hits with 3 mismatches |
|---|---|---|---|---|---|---|---|---|
| [N20]NGG | 136872907 | 136872926 | | | CAACCACCACAAGTCATTGGGG (SEQ ID NO: 182) | | | 6 |
| [N20]NGG | 136872908 | 136872927 | | 2 | ACAAGTCATTGGGGTAGAAGCGG (SEQ ID NO: 183) | 1 | | 69 |
| [N20]NGG | 136872973 | 136872994 | | | GTCATTGGCTCATTGAGCGTTGG (SEQ ID NO: 184) | 1 | 2 | 24 |
| [N20]NGG | 136872988 | 136872989 | | 1 | GAGGTTGGCAAAGATGAAGTCGG (SEQ ID NO: 185) | | | 128 |
| [N20]NGG | 136872989 | 136872968 | | 1 | AGGTTGGCAAAGATGAAGTCGGG (SEQ ID NO: 186) | 1 | | 13 |
| [N20]NGG | 136873002 | 136873003 | | 1 | TGAAGTCGGGGAATAGTCAGCAGG (SEQ ID NO: 187) | | 3 | 9 |
| [N20]NGG | 136873005 | 136873006 | | 1 | AGTCGGGAATAGTCAGCAGGCAGG (SEQ ID NO: 188) | 2 | 2 | 3.2 |
| [N20]NGG | 136873006 | 136873007 | | 1 | GTCGGGAATAGTCAGCAGGAGGGG (SEQ ID NO: 189) | 1 | | 11 |
| [N20]NGG | 136873010 | 136873011 | | 1 | GGAATAGTCAGCAGGAGGGCAGG (SEQ ID NO: 190) | 2 | | 23 |
| [N20]NGG | 136873011 | 136873012 | | 1 | GAATAGTCAGCAGGAGGGCAGGG (SEQ ID NO: 191) | 1 | 2 | 26 |
| [N20]NGG | 136873058 | 136873059 | | 1 | TTTCAGCCAACAGTTCCTTGG (SEQ ID NO: 192) | 1 | 2 | 34 |
| [N20]NGG | 136873072 | 136873073 | | 1 | CTTCCTTGGCCTCTGACTGTTGG (SEQ ID NO: 193) | | 1 | 63 |
| [N20]NGG | 136873075 | 136873076 | | 1 | CCTTGGCCTCTGACTGTTGGTGG (SEQ ID NO: 194) | 3 | 1 | 28 |
| [N20]NGG | 136873080 | 136873081 | | 1 | GCCTCTGACTGTTGGTGGCGTGG (SEQ ID NO: 195) | 3 | 3 | 50 |

FIG. 2 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| {N20}NGG | 136873087 | 136873088 | 1 | 422 | ACTGTTGGTGGCGTGGACGATGG (SEQ ID NO: 196) | | 1 | 12 |
| {N20}NGG | 136873093 | 136873093 | 1 | 427 | TGGTGGCGTGGACGATGGCCAGG (SEQ ID NO: 197) | | 1 | 14 |
| {N20}NGG | 136873098 | 136873099 | 1 | 411 | CGTGGACGATGGCCAGGTAGGCG (SEQ ID NO: 198) | | 2 | 19 |
| {N20}NGG | 136873114 | 136873115 | 1 | 365 | GTAGCGGTCCAGACTGATGAAAGG (SEQ ID NO: 199) | 1 | 2 | 10 |
| {N20}NGG | 136873119 | 136873120 | 1 | 380 | GGTCCAGACTGATGAAAGGCCAGG (SEQ ID NO: 200) | 2 | 2 | 12 |
| {N20}NGG | 136873125 | 136873126 | 1 | 384 | GACTGATGAAAGGCCAGGATGAGG (SEQ ID NO: 201) | 2 | 1 | 39 |
| {N20}NGG | 136873140 | 136873141 | 1 | 369 | GGATGAGGACACTGCTGTAGGAGG (SEQ ID NO: 202) | 1 | 4 | 35 |
| {N20}NGG | 136873161 | 136873162 | 1 | 348 | CGTTGACTGTGTAGATGACATGG (SEQ ID NO: 203) | 2 | 2 | 17 |
| {N20}NGG | 136873176 | 136873177 | 1 | 333 | TGACATGGACTGCCTTGCATAGG (SEQ ID NO: 204) | 1 | 2 | 24 |
| {N20}NGG | 136873203 | 136873205 | 1 | 306 | CCCAAAGTACCAGTTTGCCAAGG (SEQ ID NO: 205) | 1 | 1 | 17 |
| {N20}NGG | 136873222 | 136873223 | 1 | 287 | CATGGCATCAACTGCCCAGGAAGG (SEQ ID NO: 206) | 1 | 1 | 24 |
| {N20}NGG | 136873223 | 136873224 | 1 | 286 | ACGGCATCAACTGCCCAGGAAGGA (SEQ ID NO: 207) | | 1 | 10 |
| {N20}NGG | 136873242 | 136873243 | 1 | 367 | AGGGAAGGTGATGACAAAGAGG (SEQ ID NO: 208) | 1 | 2 | 23 |
| {N20}NGG | 136873245 | 136873246 | 1 | 264 | GAAGGTGATGACAAAGAGGAAGG (SEQ ID NO: 209) | 1 | 1 | 13 |

FIG. 2 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 136873239 | 136873259 | 1 | 260 | CGTGATGACAAAGAAGGATGGTCGG (SEQ ID NO: 210) | | | 23 |
| (N20)NGG | 136873260 | 136873261 | 1 | 249 | AGAGGAGGGTCGGCCACGACACAGG (SEQ ID NO: 211) | | 1 | 17 |
| (N20)NGG | 136873282 | 136873303 | 1 | 207 | TCATGCTCTCAGTTTCTTCTTCTGG (SEQ ID NO: 212) | | 1 | 72 |
| (N20)NGG | 136873317 | 136873318 | 1 | 192 | TCTTCTGGTACCCATGACCAGG (SEQ ID NO: 213) | | 1 | 39 |
| (N20)NGG | 136873350 | 136873361 | 1 | 149 | AATGCCAGTTAAGAAGATGATGG (SEQ ID NO: 214) | | 1 | 34 |
| (N20)NGG | 136873369 | 136873370 | 1 | 130 | TAAGAAGATGATGGAGTAGATGG (SEQ ID NO: 215) | | 1 | 6.2 |
| (N20)NGG | 136873372 | 136873373 | 1 | 137 | GAAGATGATGGAGTAGATGGTGG (SEQ ID NO: 216) | | 1 | 83 |
| (N20)NGG | 136873373 | 136873378 | 1 | 136 | AAGATGATGGAGTAGATGGTGGG (SEQ ID NO: 217) | | 1 | 34 |
| (N20)NGG | 136873377 | 136873378 | 1 | 132 | TGATGGAGTAGATGGTGGGCAGG (SEQ ID NO: 218) | | 2 | 34 |
| (N20)NGG | 136873410 | 136873411 | 1 | 99 | TGAAATTAGGCATTTCTTCACGG (SEQ ID NO: 219) | | 2 | 109 |
| (N20)NGG | 136873417 | 136873418 | 1 | 92 | AGCATTTCTTCACGGAAACAGG (SEQ ID NO: 220) | | 1 | 16 |
| (N20)NGG | 136873428 | 136873429 | 1 | 91 | GCATTTCTTCACGGAAATAGG (SEQ ID NO: 221) | | 1 | 29 |
| (N20)NGG | 136873429 | 136873430 | 1 | 80 | ACGGAAACAGGGTTCCTTCATGG (SEQ ID NO: 222) | | 1 | 14 |
| (N20)NGG | 136873459 | 136873460 | 1 | 50 | GTCCCTGAGCCCATTTCCTCGG (SEQ ID NO: 223) | | 1 | 28 |

FIG. 2 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| [N20]NGG | 136873493 | 136873484 | 1 | | GAAGTGTATATCTGCAAAAGAGG (SEQ ID NO: 224) | | | 24 |
| [N20]NGG | 136873499 | 136873509 | 1 | | TATATCTGCAAAAGAGGCAAAGG (SEQ ID NO: 225) | 1 | 2 | 36 |
| [N20]NGG | 136873504 | 136873505 | 1 | | CTGCAAAAGAGGCAAAGGAATGG (SEQ ID NO: 226) | | 6 | 30 |
| [N20]NGG | 136872490 | 136872491 | -1 | | CTCTCCAAAAGGAAAGGSAGGTGG (SEQ ID NO: 227) | 1 | 7 | 20 |
| [N20]NGG | 136872493 | 136872494 | -1 | | ATCCTTCCAAAAGGAAAAGCGAGG (SEQ ID NO: 228) | 1 | 1 | 13 |
| [N20]NGG | 136872502 | 136872503 | -1 | | AGCTCAAGATCTCTCTCCAAAGG (SEQ ID NO: 229) | 2 | 3 | 15 |
| [N20]NGG | 136872528 | 136872529 | -1 | | CACTCACCTCTGTGAGCAGAGG (SEQ ID NO: 230) | 1 | 2 | 91 |
| [N20]NGG | 136872529 | 136872530 | -1 | | GCACTCACCTCTGTGAGCAGAGG (SEQ ID NO: 231) | 1 | 13 | 69 |
| [N20]NGG | 136872580 | 136872581 | -1 | | CCCATCCCTATGCTTCCTTGG (SEQ ID NO: 232) | 1 | 7 | 36 |
| [N20]NGG | 136872653 | 136872653 | -1 | | CAAGTGGATTTCCATCACCGAGG (SEQ ID NO: 233) | 1 | 8 | 9 |
| [N20]NGG | 136872648 | 136872649 | -1 | | TTGAGACATCTGCACAAGTGG (SEQ ID NO: 234) | 1 | 3 | 15 |
| [N20]NGG | 136872678 | 136872679 | -1 | | TCCTGGAAATCATCAAGCAAGGG (SEQ ID NO: 235) | 1 | 2 | 24 |
| [N20]NGG | 136872679 | 136872680 | -1 | | CTCCTGGAAATCATCAAGCAAGG (SEQ ID NO: 236) | 1 | | 30 |
| [N20]NGG | 136872695 | 136872696 | -1 | | CATCGACTTCCTTTATCTTGCTGG (SEQ ID NO: 237) | 1 | 2 | 12 |

FIG. 2 cont.

| site type | site_start | site_end | site_strand | relative_start | site sequence | genome wide hits with 1 mismatches | genome wide hits with 2 mismatches | genome wide hits with 3 mismatches |
|---|---|---|---|---|---|---|---|---|
| [N20]NGG | 136872723 | 136872725 | -1 | 786 | GTTGGCTGCCTTACTACGATTGGG (SEQ ID NO: 238) | | 3 | 10 |
| [N20]NGG | 136872724 | 136872726 | -1 | 785 | TGTGGCTGGCTTATATACGATTGG (SEQ ID NO: 239) | | 3 | 12 |
| [N20]NGG | 136872741 | 136872743 | -1 | 768 | TCCTGGCTTCTTCGCCTGTTGG (SEQ ID NO: 240) | 1 | 2 | 15 |
| [N20]NGG | 136872758 | 136872760 | -1 | 751 | GACCACAGTCATCCTCATCCTGG (SEQ ID NO: 241) | 1 | 2 | 24 |
| [N20]NGG | 136872788 | 136872790 | -1 | 721 | CAAGGGACACTAGGAAAGGCAAGG (SEQ ID NO: 242) | 1 | 1 | 16 |
| [N20]NGG | 136872805 | 136872807 | -2 | 704 | TCCAAGCTGTCACACTCCAAGGG (SEQ ID NO: 243) | 1 | 2 | 15 |
| [N20]NGG | 136872806 | 136872808 | -1 | 703 | CTCCAAGCTGTCACACTCCAAGG (SEQ ID NO: 244) | 1 | 2 | 15 |
| [N20]NGG | 136872862 | 136872864 | -1 | 647 | ATGGTTGGCCTTATCCTGGATGG (SEQ ID NO: 245) | 1 | 1 | 13 |
| [N20]NGG | 136872877 | 136872879 | -1 | 632 | CAGTTCAGCACATCATGGTTGG (SEQ ID NO: 246) | 1 | 3 | 9 |
| [N20]NGG | 136872881 | 136872883 | -1 | 628 | GTTCCAGTTCAGCACATCATGG (SEQ ID NO: 247) | 1 | 4 | 46 |
| [N20]NGG | 136872908 | 136872910 | -1 | 601 | CTAGCCCAATGACTTGTGGGTGG (SEQ ID NO: 248) | 1 | 1 | 7 |
| [N20]NGG | 136872911 | 136872913 | -1 | 598 | CTTCTACCCAATGACTTGTGGG (SEQ ID NO: 249) | 1 | 1 | 15 |
| [N20]NGG | 136872917 | 136872919 | -1 | 592 | GCTTCTACCCAATGACTTGTGG (SEQ ID NO: 250) | 1 | 1 | 8 |
| [N20]NGG | 136872959 | 136872960 | -1 | 550 | CATCTTGCCAACGTCAGTGACG (SEQ ID NO: 251) | 1 | 2 | 12 |

FIG. 2 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| [N20]NGG | 136873014 | 136873016 | | -1 | AGGTGTCTATGTTGGAGTATGG (SEQ ID NO: 252) | | | 3 |
| [N20]NGG | 136873023 | 136873032 | | -1 | GCTGAAAAGGTGGTCTATGTGG (SEQ ID NO: 253) | | | 16 |
| [N20]NGG | 136873033 | 136873032 | | -1 | GAAGCTGTTGGCTGAAAAGGTGG (SEQ ID NO: 254) | | 1 | 55 |
| [N20]NGG | 136873034 | 136873035 | | -1 | AAGGAAGCTGTTGGTGAAAAGG (SEQ ID NO: 255) | | 1 | 42 |
| [N20]NGG | 136873043 | 136873044 | | -1 | TCAGAGGCCAAGGAAGCTGTTGG (SEQ ID NO: 256) | | 2 | 55 |
| [N20]NGG | 136873053 | 136873054 | | -1 | CCACCAACAGTCAGAGGCCAAGG (SEQ ID NO: 257) | | 1 | 34 |
| [N20]NGG | 136873059 | 136873060 | | -1 | TCCACGCCACAACAGTCAGAGG (SEQ ID NO: 258) | | 1 | 15 |
| [N20]NGG | 136873098 | 136873099 | | -1 | CATCCTGGCCTTGATCAGTCTGG (SEQ ID NO: 259) | | 1 | 26 |
| [N20]NGG | 136873100 | 136873101 | | -1 | CATCCTGGCCTTGATCAGTCTGG (SEQ ID NO: 260) | | 3 | 19 |
| [N20]NGG | 136873115 | 136873116 | | -1 | CTACAGCAGTGTCCTCATCCTGG (SEQ ID NO: 261) | | 1 | 30 |
| [N20]NGG | 136873166 | 136873167 | | -1 | CTTTGGGAACTTCTTATGCAAGG (SEQ ID NO: 262) | | 2 | 22 |
| [N20]NGG | 136873182 | 136873183 | | -1 | CCGTAGCAAACTGGTACTTTGG (SEQ ID NO: 263) | | 2 | 6 |
| [N20]NGG | 136873183 | 136873184 | | -1 | GCCGTGGCAAACTGGTACTTTGG (SEQ ID NO: 264) | | 1 | 6 |
| [N20]NGG | 136873191 | 136873192 | | -1 | CAGTTGATCCCCTTGCCAAACTGG (SEQ ID NO: 265) | | 1 | |

FIG. 2 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| [N20]NGG | 136873299 | 136873280 | | -1 | CTTCTGGCAGTTGATGGGTGG (SEQ ID NO: 266) | | 1 | 8 |
| [N20]NGG | 136873214 | 136873225 | | -1 | TGTCATCACGCTTCCTTCTGGG (SEQ ID NO: 267) | 1 | 1 | 11 |
| [N20]NGG | 136873215 | 136873216 | | -1 | TTGTCATCACGCTTCCTTCTGG (SEQ ID NO: 268) | | 1 | 7 |
| [N20]NGG | 136873260 | 136873251 | | -1 | GTACAGGCTGCACCTGTCAGTGG (SEQ ID NO: 269) | | 2 | 12 |
| [N20]NGG | 136873265 | 136873267 | | -1 | GAACGATGAGGACAAGTACAGG (SEQ ID NO: 270) | 1 | 1 | 6 |
| [N20]NGG | 136873277 | 136873278 | | 1 | GAAGAAACTGAGAAAGCATGAGGG (SEQ ID NO: 271) | 5 | 1 | 50 |
| [N20]NGG | 136873306 | 136873307 | | 1 | GGATTGGTCATCCTGGTCATGG (SEQ ID NO: 272) | | 1 | 20 |
| [N20]NGG | 136873307 | 136873308 | | -1 | TGGATTGGTCATCCTGGTCATGG (SEQ ID NO: 273) | 1 | 1 | 13 |
| [N20]NGG | 136873313 | 136873314 | | -1 | GGGCAATGGATGGTCATCCTGG (SEQ ID NO: 274) | | 1 | 8 |
| [N20]NGG | 136873222 | 136873223 | | 1 | TGGCATTGTGGGCLAATGGATTGG (SEQ ID NO: 275) | | 1 | 23 |
| [N20]NGG | 136873327 | 136873328 | | 1 | TTAACTGGCATTGTGGGCAATGG (SEQ ID NO: 276) | 1 | 2 | 14 |
| [N20]NGG | 136873333 | 136873334 | | 1 | ATCTTCTTAACTGGCATTGTGGG (SEQ ID NO: 277) | | 1 | 18 |
| [N20]NGG | 136873334 | 136873335 | | 1 | CATCTTCTTAACTGGCATTGTGG (SEQ ID NO: 278) | 3 | 1 | 15 |
| [N20]NGG | 136873342 | 136873343 | | -1 | TACCCATCATCTTCTTAACTGG (SEQ ID NO: 279) | | 2 | 22 |

FIG. 2 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| (N20)NGG | 136873421 | 136873442 | -1 | | AGGGGACTAYGACTCCATGGAAGG (SEQ ID NO: 280) | | 2 | 20 |
| (N19)NGG | 136873439 | 136873440 | -1 | | CACCGAGGGAAATGGCTCAGGGG (SEQ ID NO: 281) | 1 | 2 | 29 |
| (N20)NGG | 136873440 | 136873441 | -1 | | ACACCGAGGGAAATGGGCTCAGGG (SEQ ID NO: 282) | 2 | 1 | 16 |
| (N20)NGG | 136873441 | 136873442 | -1 | | TACACCGAGGGAAATGGGCTCAGG (SEQ ID NO: 283) | | 1 | 11 |
| (N20)NGG | 136873447 | 136873448 | -1 | | GATAACTACACCGAGGGAAATGGG (SEQ ID NO: 284) | 1 | 2 | 6 |
| (N20)NGG | 136873448 | 136873449 | -1 | | AGATAACTACACCGAGGGAAATGG (SEQ ID NO: 285) | | 1 | 11 |
| (N20)NGG | 136873454 | 136873455 | -1 | | GACTTCAGATAACTACACCGACGG (SEQ ID NO: 286) | 1 | 2 | 6 |
| (N21)RNNAGAAW | 136872624 | 136872625 | 1 | 885 | A (SEQ ID NO: 287) GATGGGGTTCAGACAACAAGTGGAAGAA | 1 | 2 | 2 |
| (R21)RNNAGAAW | 136872756 | 136872757 | 1 | 753 | A (SEQ ID NO: 288) GTAGTAAGGCAGCCAACAGGCGAAGAA | | 1 | 1 |
| (N21)NRAGAAW | 136872693 | 136872694 | 1 | 576 | (SEQ ID NO: 289) AACCACCCACAGTCATTGGGGTAGAAG | | 1 | 1 |
| (N21)NNAGAAW | 136873221 | 136873222 | 1 | 388 | (SEQ ID NO: 290) GTTGCCACGGCATCAACTGCCCAGAAG | 1 | 2 | 2 |
| (N23)NNAGAAW | 136873353 | 136873354 | 1 | 136 | (SEQ ID NO: 291) TGCATGGCCACAATGCCAGTTAAGAAG | | 1 | 1 |
| BTTCTRR(N23) | 136872663 | 136872664 | -1 | | CATCAAGCAAGGGTGTGACTTTGAGGAAC (SEQ ID NO: 292) | 1 | 1 | 2 |
| BTTCTRR(N21) | 136872265 | 136872266 | -1 | | GCTGTCACACTCCAAGGGCACCAGAAG (SEQ ID NO: 293) | 1 | 1 | 2 |

FIG. 2 cont.

| site_type | site_start | site_end | site_strand | relative_start | site_sequence | genome wide hits with 1 mismatches | genome wide hits with 2 mismatches | genome wide hits with 3 mismatches |
|---|---|---|---|---|---|---|---|---|
| BT*CTNN(N21) | 136873226 | 136873286 | -1 | 224 | GTCATGGGTTACCAGAAGAAACTGAGAA (SEQ ID NO: 294) | | 1 | 2 |
| BT*CTNN(N21) | 136873233 | 136873294 | -1 | 216 | CATCCTGGTCATGGGTTACCAGAAGAAA (SEQ ID NO: 295) | 1 | 1 | 1 |
| BT*CTNN(N21) | 136873236 | 136873297 | 1 | 213 | GGTCATCCTGGTCATGGGTTACCAGAAG (SEQ ID NO: 296) | 1 | 2 | 1 |
| BT*CTNN(N21) | 136873400 | 136873401 | 1 | 109 | ATGAAGGAACCTGTTTCCGTGAAGAAAA (SEQ ID NO: 297) | 1 | 1 | 1 |

FIG. 2 cont.

```
  1 MDKKYSIGLD IGTNSVGWAV ITDEYKVPSK KFKVLGNTDR HSIKKNLIGA LLFDSGETAE
 61 ATRLKRTARR RYTRRKNRIC YLQEIFSNEM AKVDDSFFHR LEESFLVEED KKHERHPIFG
121 NIVDEVAYHE KYPTIYHLRK KLVDSTDKAD LRLIYLALAH MIKFRGHFLI EGDLNPDNSD
181 VDKLFIQLVQ TYNQLFEENP INASGVDAKA ILSARLSKSR RLENLIAQLP GEKKNGLFGN
241 LIALSLGLTP NFKSNFDLAE DAKLQLSKDT YDDDLDNLLA QIGDQYADLF LAAKNLSDAI
301 LLSDILRVNT EITKAPLSAS MIKRYDEHHQ DLTLLKALVR QQLPEKYKEI FFDQSKNGYA
361 GYIDGGASQE EFYKFIKPIL EKMDGTEELL VKLNREDLLR KQRTFDNGSI PHQIHLGELH
421 AILRRQEDFY PFLKDNREKI EKILTFRIPY YVGPLARGNS RFAWMTRKSE ETITPWNFEE
481 VVDKGASAQS FIERMTNFDK NLPNEKVLPK HSLLYEYFTV YNELTKVKYV TEGMRKPAFL
541 SGEQKKAIVD LLFKTNRKVT VKQLKEDYFK KIECFDSVEI SGVEDRFNAS LGTYHDLLKI
601 IKDKDFLDNE ENEDILEDIV LTLTLFEDRE MIEERLKTYA HLFDDKVMKQ LKRRRYTGWG
661 RLSRKLINGI RDKQSGKTIL DFLKSDGFAN RNFMQLIHDD SLTFKEDIQK AQVSGQGDSL
721 HEHIANLAGS PAIKKGILQT VKVVDELVKV MGRHKPENIV IEMARENQTT QKGQKNSRER
781 MKRIEEGIKE LGSQILKEHP VENTQLQNEK LYLYYLQNGR DMYVDQELDI NRLSDYDVDH
841 IVPQSFLKDD SIDNKVLTRS DKNRGKSDNV PSEEVVKKMK NYWRQLLNAK LITQRKFDNL
901 TKAERGGLSE LDKAGFIKRQ LVETRQITKH VAQILDSRMN TKYDENDKLI REVKVITLKS
961 KLVSDFRKDF QFYKVREINN YHHAHDAYLN AVVGTALIKK YPKLESEFVY GDYKVYDVRK
1021 MIAKSEQEIG KATAKYFFYS NIMNFFKTEI TLANGEIRKR PLIETNGETG EIVWDKGRDF
1081 ATVRKVLSMP QVNIVKKTEV QTGGFSKESI LPKRNSDKLI ARKKDWDPKK YGGFDSPTVA
1141 YSVLVVAKVE KGKSKKLKSV KELLGITIME RSSFEKNPID FLEAKGYKEV KKDLIIKLPK
1201 YSLFELENGR KRMLASAGEL QKGNELALPS KYVNFLYLAS HYEKLKGSPE DNEQKQLFVE
1261 QHKHYLDEII EQISEFSKRV ILADANLDKV LSAYNKHRDK PIREQAENII HLFTLTNLGA
1321 PAAFKYFDTT IDRKRYTSTK EVLDATLIHQ SITGLYETRI DLSQLGGD (SEQ ID NO: 298)
```

| Guide ID | Target Site Sequence With NGG | Score |
|---|---|---|
| crCCR5_F | GTAGAGCGGAGGCAGGAGGCGGG (SEQ ID NO: 304) | 16 |
| crCCR5_G | GTGAGTAGAGCGGAGGCAGGAGG (SEQ ID NO: 305) | 32 |
| crCCR5_H | GGTGTTCATCTTTGGTTTTGTGG (SEQ ID NO: 306) | 26 |
| crCCR5_I | GTGTTCATCTTTGGTTTTGTGGG (SEQ ID NO: 307) | 26 |
| crCCR5_J | GGACAGTAAGAAGGAAAAACAGG (SEQ ID NO: 308) | 16 |
| crCCR5_A | GCTGCCGCCCAGTGGGACTTTGG (SEQ ID NO: 309) | 64 |
| crCCR5_K | GCAGCATAGTGAGCCCAGAAGGG (SEQ ID NO: 310) | 41 |
| crCCR5_L | GGCAGCATAGTGAGCCCAGAAGG (SEQ ID NO: 311) | 38 |
| crCCR5_M | GGTACCTATCGATTGTCAGGAGG (SEQ ID NO: 312) | 45 |
| crCCR5_N | GTTTGCTTTAAAAGCCAGGACGG (SEQ ID NO: 313) | 21 |
| crCCR5_O | GGTGACAAGTGTGATCACTTGGG (SEQ ID NO: 314) | 56 |
| crCCR5_P | GACAAGTGTGATCACTTGGGTGG (SEQ ID NO: 315) | 61 |
| crCCR5_Q | GCTGTGTTTGCGTCTCTCCCAGG (SEQ ID NO: 316) | 53 |
| crCCR5_B | GATCTGGTAAAGATGATTCCTGG (SEQ ID NO: 317) | 55 |
| crCCR5_R | GTATGGAAAATGAGAGCTGCAGG (SEQ ID NO: 318) | 43 |
| crCCR5_S | GACATTAAAGATAGTCATCTTGG (SEQ ID NO: 319) | 50 |
| crCCR5_T | GGTCCTGCCGCTGCTTGTCATGG (SEQ ID NO: 320) | 55 |
| crCCR5_U | GTCATGGTCATCTGCTACTCGGG (SEQ ID NO: 321) | 38 |
| crCCR5_V | GAATCCTAAAAACTCTGCTTCGG (SEQ ID NO: 322) | 43 |
| crCCR5_W | GGTGTCGAAATGAGAAGAAGAGG (SEQ ID NO: 323) | 32 |
| crCCR5_X | GACACCGAAGCAGAGTTTTTAGG (SEQ ID NO: 324) | 59 |
| crCCR5_Y | GAAATGAGAAGAAGAGGCACAGG (SEQ ID NO: 325) | 23 |
| crCCR5_1 | GATTGTTTATTTTCTCTTCTGGG (SEQ ID NO: 326) | 14 |
| crCCR5_Z | GAGAAAATAAACAATCATGATGG (SEQ ID NO: 327) | 14 |
| crCCR5_2 | GCTTTTGGAAGAAGACTAAGAGG (SEQ ID NO: 328) | 34 |
| crCCR5_3 | GTAAACTGAGCTTGCTCGCTCGG (SEQ ID NO: 329) | 80 |
| crCCR5_4 | GGGGAGCAGGAAATATCTGTGGG (SEQ ID NO: 330) | 45 |
| crCCR5_C | ACAATGTGTCAACTCTTGACAGG (SEQ ID NO: 331) | 67 |
| crCCR5_D | TCACTATGCTGCCGCCCAGTGGG (SEQ ID NO: 332) | 81 |
| crCCR5_E | GGTACCTATCGATTGTCAGGAGG (SEQ ID NO: 333) | 45 |

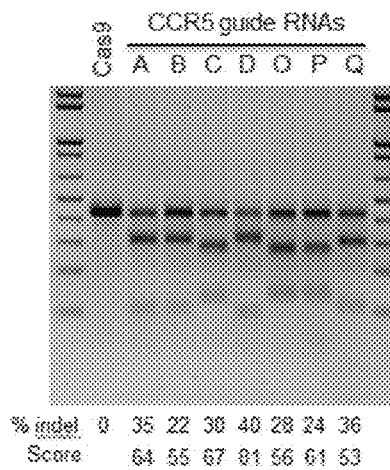

FIG. 4A

SEQUENCE LISTING

<160> NUMBER OF SEQ ID NOS: 353

<210> SEQ ID NO 1
<211> LENGTH: 23

```
<212> TYPE: DNA
<213> ORGANISM: Artificial
<220> FEATURE:
<223> OTHER INFORMATION: CCR5 gRNA target site sequence

<400> SEQUENCE: 1
tgacatcaat tattatacat cgg                                            23

<210> SEQ ID NO 2
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 2
cctgcctccg ctctactcac tgg                                            23

<210> SEQ ID NO 3
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 3
tactcactgg tgttcatctt tgg                                            23

<210> SEQ ID NO 4
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 4
ggtgttcatc tttggttttg tgg                                            23

<210> SEQ ID NO 5
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 5
gtgttcatct ttggttttgt ggg                                            23

<210> SEQ ID NO 6
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 6
tggttttgtg ggcaacatgc tgg                                            23

<210> SEQ ID NO 7
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 7
```
tcatcctgat aaactgcaaa agg                                          23

<210> SEQ ID NO 8
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 8
tgacatctac ctgctcaacc tgg                                          23

<210> SEQ ID NO 9
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 9
tccttcttac tgtccccttc tgg                                          23

<210> SEQ ID NO 10
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 10
ccttcttact gtccccttct ggg                                          23

<210> SEQ ID NO 11
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 11
ctcactatgc tgccgcccag tgg                                          23

<210> SEQ ID NO 12
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 12
tcactatgct gccgcccagt ggg                                          23

<210> SEQ ID NO 13
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 13
gctgccgccc agtgggactt tgg                                          23

<210> SEQ ID NO 14
<211> LENGTH: 23
<212> TYPE: DNA
<213> ORGANISM: Artificial

```
<220> FEATURE:
<223> OTHER INFORMATION: CCR5 gRNA target site sequence

<400> SEQUENCE: 14
acaatgtgtc aactcttgac agg                                              23

<210> SEQ ID NO 15
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 15
caatgtgtca actcttgaca ggg                                              23

<210> SEQ ID NO 16
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 16
ttgacagggc tctattttat agg                                              23

<210> SEQ ID NO 17
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 17
tattttatag gcttcttctc tgg                                              23

<210> SEQ ID NO 18
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 18
tcatcctcct gacaatcgat agg                                              23

<210> SEQ ID NO 19
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 19
cctgacaatc gataggtacc tgg                                              23

<210> SEQ ID NO 20
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 20
ctgtgtttgc tttaaaagcc agg                                              23
```

```
<210> SEQ ID NO 21
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 21
gtttgcttta aaagccagga cgg                                              23

<210> SEQ ID NO 22
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 22
aaagccagga cggtcaccttt tgg                                             23

<210> SEQ ID NO 23
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 23
aagccaggac ggtcaccttt ggg                                              23

<210> SEQ ID NO 24
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 24
agccaggacg gtcacctttg ggg                                              23

<210> SEQ ID NO 25
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 25
caggacggtc acctttgggg tgg                                              23

<210> SEQ ID NO 26
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 26
tggtgacaag tgtgatcact tgg                                              23

<210> SEQ ID NO 27
<211> LENGTH: 23
<212> TYPE: DNA
<213> ORGANISM: Artificial
<220> FEATURE:
<223> OTHER INFORMATION: CCR5 gRNA target site sequence
```

```
<400> SEQUENCE: 27
ggtgacaagt gtgatcactt ggg                                          23

<210> SEQ ID NO 28
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 28
gacaagtgtg atcacttggg tgg                                          23

<210> SEQ ID NO 29
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 29
aagtgtgatc acttgggtgg tgg                                          23

<210> SEQ ID NO 30
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 30
gctgtgtttg cgtctctccc agg                                          23

<210> SEQ ID NO 31
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 31
tttaccagat ctcaaaaaga agg                                          23

<210> SEQ ID NO 32
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 32
catacagtca gtatcaattc tgg                                          23

<210> SEQ ID NO 33
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 33
gacattaaag atagtcatct tgg                                          23

<210> SEQ ID NO 34
```

```
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 34
acattaaaga tagtcatctt ggg                                              23

<210> SEQ ID NO 35
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 35
cattaaagat agtcatcttg ggg                                              23

<210> SEQ ID NO 36
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 36
aaagatagtc atcttggggc tgg                                              23

<210> SEQ ID NO 37
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 37
ggtcctgccg ctgcttgtca tgg                                              23

<210> SEQ ID NO 38
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 38
tgtcatggtc atctgctact cgg                                              23

<210> SEQ ID NO 39
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 39
gtcatggtca tctgctactc ggg                                              23

<210> SEQ ID NO 40
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 40
```

-continued

```
gaatcctaaa aactctgctt cgg                                              23

<210> SEQ ID NO 41
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 41
ggtgtcgaaa tgagaagaag agg                                              23

<210> SEQ ID NO 42
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 42
gaaatgagaa gaagaggcac agg                                              23

<210> SEQ ID NO 43
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 43
aaatgagaag aagaggcaca ggg                                              23

<210> SEQ ID NO 44
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 44
agaagaggca cagggctgtg agg                                              23

<210> SEQ ID NO 45
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 45
tgattgttta ttttctcttc tgg                                              23

<210> SEQ ID NO 46
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 46
gattgtttat tttctcttct ggg                                              23

<210> SEQ ID NO 47
<211> LENGTH: 23
<212> TYPE: DNA
```

```
<213> ORGANISM: Artificial
<220> FEATURE:
<223> OTHER INFORMATION: CCR5 gRNA target site sequence

<400> SEQUENCE: 47
ccttctcctg aacaccttcc agg                                          23

<210> SEQ ID NO 48
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 48
aacaccttcc aggaattctt tgg                                          23

<210> SEQ ID NO 49
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 49
ataattgcag tagctctaac agg                                          23

<210> SEQ ID NO 50
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 50
ttgcagtagc tctaacaggt tgg                                          23

<210> SEQ ID NO 51
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 51
caggttggac caagctatgc agg                                          23

<210> SEQ ID NO 52
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 52
atgcaggtga cagagactct tgg                                          23

<210> SEQ ID NO 53
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 53
tgcaggtgac agagactctt ggg                                          23
```

<210> SEQ ID NO 54
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 54
cccatcatct atgcctttgt cgg                                    23

<210> SEQ ID NO 55
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 55
ccatcatcta tgcctttgtc ggg                                    23

<210> SEQ ID NO 56
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 56
catcatctat gcctttgtcg ggg                                    23

<210> SEQ ID NO 57
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 57
ctgttctatt ttccagcaag agg                                    23

<210> SEQ ID NO 58
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 58
tcagtttaca cccgatccac tgg                                    23

<210> SEQ ID NO 59
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 59
cagtttacac ccgatccact ggg                                    23

<210> SEQ ID NO 60
<211> LENGTH: 23
<212> TYPE: DNA
<213> ORGANISM: Artificial
<220> FEATURE:

```
<223> OTHER INFORMATION: CCR5 gRNA target site sequence

<400> SEQUENCE: 60
agtttacacc cgatccactg ggg                                              23

<210> SEQ ID NO 61
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 61
cacccgatcc actggggagc agg                                              23

<210> SEQ ID NO 62
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 62
tggggagcag gaaatatctg tgg                                              23

<210> SEQ ID NO 63
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 63
ggggagcagg aaatatctgt ggg                                              23

<210> SEQ ID NO 64
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 64
taataattga tgtcatagat tgg                                              23

<210> SEQ ID NO 65
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 65
ttcacattga tttttggca ggg                                               23

<210> SEQ ID NO 66
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 66
cttcacattg atttttggc agg                                               23
```

```
<210> SEQ ID NO 67
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 67
tttgcttcac attgattttt tgg                                          23

<210> SEQ ID NO 68
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 68
gtagagcgga ggcaggaggc ggg                                          23

<210> SEQ ID NO 69
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 69
agtagagcgg aggcaggagg cgg                                          23

<210> SEQ ID NO 70
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 70
gtgagtagag cggaggcagg agg                                          23

<210> SEQ ID NO 71
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 71
ccagtgagta gagcggaggc agg                                          23

<210> SEQ ID NO 72
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 72
aacaccagtg agtagagcgg agg                                          23

<210> SEQ ID NO 73
<211> LENGTH: 23
<212> TYPE: DNA
<213> ORGANISM: Artificial
<220> FEATURE:
<223> OTHER INFORMATION: CCR5 gRNA target site sequence
```

<400> SEQUENCE: 73
atgaacacca gtgagtagag cgg                                              23

<210> SEQ ID NO 74
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 74
ttttgcagtt tatcaggatg agg                                              23

<210> SEQ ID NO 75
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 75
tcagcctttt gcagtttatc agg                                              23

<210> SEQ ID NO 76
<211> LENGTH: 23
<212> TYPE: DNA
<213> ORGANISM: Artificial
<220> FEATURE:
<223> OTHER INFORMATION: CXCR5 gRNA target site sequence

<400> SEQUENCE: 76
cagagatggc caggttgagc agg                                              23

<210> SEQ ID NO 77
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 77
aaaacaggtc agagatggcc agg                                              23

<210> SEQ ID NO 78
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 78
aaggaaaaac aggtcagaga tgg                                              23

<210> SEQ ID NO 79
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 79
ggacagtaag aaggaaaaac agg                                              23

<210> SEQ ID NO 80
<211> LENGTH: 23

```
<212> TYPE: DNA
<213> ORGANISM: Artificial
<220> FEATURE:
<223> OTHER INFORMATION: CCR5 gRNA target site sequence

<400> SEQUENCE: 80
cccagaaggg gacagtaaga agg                                          23

<210> SEQ ID NO 81
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 81
cagcatagtg agcccagaag ggg                                          23

<210> SEQ ID NO 82
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 82
gcagcatagt gagcccagaa ggg                                          23

<210> SEQ ID NO 83
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 83
ggcagcatag tgagcccaga agg                                          23

<210> SEQ ID NO 84
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 84
atttccaaag tcccactggg cgg                                          23

<210> SEQ ID NO 85
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 85
tgtatttcca aagtcccact ggg                                          23

<210> SEQ ID NO 86
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 86
```
ttgtatttcc aaagtcccac tgg                                        23

<210> SEQ ID NO 87
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 87
ggtacctatc gattgtcagg agg                                        23

<210> SEQ ID NO 88
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 88
ccaggtacct atcgattgtc agg                                        23

<210> SEQ ID NO 89
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 89
acacagcatg gacgacagcc agg                                        23

<210> SEQ ID NO 90
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 90
cttttaaagc aaacacagca tgg                                        23

<210> SEQ ID NO 91
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 91
caccccaaag gtgaccgtcc tgg                                        23

<210> SEQ ID NO 92
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 92
cacacttgtc accaccccaa agg                                        23

<210> SEQ ID NO 93
<211> LENGTH: 23
<212> TYPE: DNA
<213> ORGANISM: Artificial

```
<220> FEATURE:
<223> OTHER INFORMATION: CCR5 gRNA target site sequence

<400> SEQUENCE: 93
atctggtaaa gatgattcct ggg                                              23

<210> SEQ ID NO 94
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 94
gatctggtaa agatgattcc tgg                                              23

<210> SEQ ID NO 95
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 95
aagaccttct ttttgagatc tgg                                              23

<210> SEQ ID NO 96
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 96
gtatggaaaa tgagagctgc agg                                              23

<210> SEQ ID NO 97
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 97
cagaattgat actgactgta tgg                                              23

<210> SEQ ID NO 98
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 98
agatgactat ctttaatgtc tgg                                              23

<210> SEQ ID NO 99
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 99
tgaccatgac aagcagcggc agg                                              23
```

```
<210> SEQ ID NO 100
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 100
cagatgacca tgacaagcag cgg                                              23

<210> SEQ ID NO 101
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 101
gacaccgaag cagagttttt agg                                              23

<210> SEQ ID NO 102
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 102
gagaaaataa acaatcatga tgg                                              23

<210> SEQ ID NO 103
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 103
aggagaagga caatgttgta ggg                                              23

<210> SEQ ID NO 104
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 104
caggagaagg acaatgttgt agg                                              23

<210> SEQ ID NO 105
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 105
cctggaaggt gttcaggaga agg                                              23

<210> SEQ ID NO 106
<211> LENGTH: 23
<212> TYPE: DNA
<213> ORGANISM: Artificial
<220> FEATURE:
<223> OTHER INFORMATION: CCR5 gRNA target site sequence
```

```
<400> SEQUENCE: 106
agaattcctg gaaggtgttc agg                                          23

<210> SEQ ID NO 107
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 107
caggccaaag aattcctgga agg                                          23

<210> SEQ ID NO 108
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 108
tattcaggcc aaagaattcc tgg                                          23

<210> SEQ ID NO 109
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 109
tagagctact gcaattattc agg                                          23

<210> SEQ ID NO 110
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 110
tctctgtcac ctgcatagct tgg                                          23

<210> SEQ ID NO 111
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 111
cgacaaaggc atagatgatg ggg                                          23

<210> SEQ ID NO 112
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 112
ccgacaaagg catagatgat ggg                                          23

<210> SEQ ID NO 113
```

```
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 113
cccgacaaag gcatagatga tgg                                              23

<210> SEQ ID NO 114
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 114
tctgaacttc tccccgacaa agg                                              23

<210> SEQ ID NO 115
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 115
gcttttggaa gaagactaag agg                                              23

<210> SEQ ID NO 116
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 116
agcgtttggc aatgtgcttt tgg                                              23

<210> SEQ ID NO 117
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 117
acagcatttg cagaagcgtt tgg                                              23

<210> SEQ ID NO 118
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 118
ctcgctcggg agcctcttgc tgg                                              23

<210> SEQ ID NO 119
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 119
```

```
taaactgagc ttgctcgctc ggg                                              23

<210> SEQ ID NO 120
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 120
gtaaactgag cttgctcgct cgg                                              23

<210> SEQ ID NO 121
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 121
ttcctgctcc ccagtggatc ggg                                              23

<210> SEQ ID NO 122
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 122
tttcctgctc cccagtggat cgg                                              23

<210> SEQ ID NO 123
<211> LENGTH: 23
<212> TYPE: DNA
<213> ORGANISM: Artificial
<220> FEATURE:
<223> OTHER INFORMATION: CCR5 gRNA target site sequence

<400> SEQUENCE: 123
agatatttcc tgctccccag tgg                                              23

<210> SEQ ID NO 124
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 124
atcatcttta ccagatctca aaagaaag                                         28

<210> SEQ ID NO 125
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 125
aactctgctt cggtgtcgaa atgagaag                                         28

<210> SEQ ID NO 126
<211> LENGTH: 28
<212> TYPE: DNA
```

```
<213> ORGANISM: Artificial
<220> FEATURE:
<223> OTHER INFORMATION: CCR5 gRNA target site sequence

<400> SEQUENCE: 126
tctgcttcgg tgtcgaaatg agaagaag                                    28

<210> SEQ ID NO 127
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 127
catcatctat gcctttgtcg gggagaag                                    28

<210> SEQ ID NO 128
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 128
atgcctttgt cggggagaag ttcagaaa                                    28

<210> SEQ ID NO 129
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 129
agtgagccca gaaggggaca gtaagaag                                    28

<210> SEQ ID NO 130
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 130
ctgggcggca gcatagtgag cccagaag                                    28

<210> SEQ ID NO 131
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 131
gatgatgaag aagattccag agaagaag                                    28

<210> SEQ ID NO 132
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 132
gaggatgatg aagaagattc cagagaag                                    28
```

```
<210> SEQ ID NO 133
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 133
atcgattgtc aggaggatga tgaagaag                                            28

<210> SEQ ID NO 134
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 134
caatgttgta gggagcccag aagagaaa                                            28

<210> SEQ ID NO 135
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 135
aaggacaatg ttgtagggag cccagaag                                            28

<210> SEQ ID NO 136
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 136
agaattcctg gaaggtgttc aggagaag                                            28

<210> SEQ ID NO 137
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 137
gcgtttggca atgtgctttt ggaagaag                                            28

<210> SEQ ID NO 138
<211> LENGTH: 28
<212> TYPE: DNA
<213> ORGANISM: Artificial
<220> FEATURE:
<223> OTHER INFORMATION: CCR5 gRNA target site sequence

<400> SEQUENCE: 138
ctggaaaata gaacagcatt tgcagaag                                            28

<210> SEQ ID NO 139
<211> LENGTH: 28
<212> TYPE: DNA
<213> ORGANISM: Artificial
<220> FEATURE:
```

```
<223> OTHER INFORMATION: CCR5 gRNA target site sequence

<400> SEQUENCE: 139
tcgggagcct cttgctggaa aatagaac                                          28

<210> SEQ ID NO 140
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 140
acttgaagac tcagactcag tgg                                               23

<210> SEQ ID NO 141
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 141
atgtccacct cgctttcctt tgg                                               23

<210> SEQ ID NO 142
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 142
cacctcgctt tcctttggag agg                                               23

<210> SEQ ID NO 143
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 143
ttcctttgga gaggatcttg agg                                               23

<210> SEQ ID NO 144
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 144
tttggagagg atcttgaggc tgg                                               23

<210> SEQ ID NO 145
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 145
gctggaccct ctgctcacag agg                                               23
```

```
<210> SEQ ID NO 146
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 146
tcacagaggt gagtgcgtgc tgg                                             23

<210> SEQ ID NO 147
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 147
cacagaggtg agtgcgtgct ggg                                             23

<210> SEQ ID NO 148
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 148
ggtgagtgcg tgctgggcag agg                                             23

<210> SEQ ID NO 149
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 149
ctgggcagag gttttaaatt tgg                                             23

<210> SEQ ID NO 150
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 150
aggttttaaa tttggctcca agg                                             23

<210> SEQ ID NO 151
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 151
tggctccaag gaaagcatag agg                                             23

<210> SEQ ID NO 152
<211> LENGTH: 23
<212> TYPE: DNA
<213> ORGANISM: Artificial
<220> FEATURE:
<223> OTHER INFORMATION: CXCR4 gRNA target site sequence
```

```
<400> SEQUENCE: 152
tccaaggaaa gcatagagga tgg                                              23

<210> SEQ ID NO 153
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 153
ccaaggaaag catagaggat ggg                                              23

<210> SEQ ID NO 154
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 154
caaggaaagc atagaggatg ggg                                              23

<210> SEQ ID NO 155
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 155
ggatggggtt cagacaacag tgg                                              23

<210> SEQ ID NO 156
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 156
gacaacagtg gaagaaagct agg                                              23

<210> SEQ ID NO 157
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 157
acaacagtgg aagaaagcta ggg                                              23

<210> SEQ ID NO 158
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 158
gtggaagaaa gctagggcct cgg                                              23

<210> SEQ ID NO 159
<211> LENGTH: 23
```

```
<210> SEQ ID NO 159
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 159
gaaagctagg gcctcggtga tgg                                              23

<210> SEQ ID NO 160
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 160
acccttgctt gatgatttcc agg                                              23

<210> SEQ ID NO 161
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 161
cttgcttgat gatttccagg agg                                              23

<210> SEQ ID NO 162
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 162
gatgatttcc aggaggatga agg                                              23

<210> SEQ ID NO 163
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 163
atgctgatcc caatgtagta agg                                              23

<210> SEQ ID NO 164
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 164
aatgtagtaa ggcagccaac agg                                              23

<210> SEQ ID NO 165
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 165
```

```
gccaacaggc gaagaaagcc agg                                             23

<210> SEQ ID NO 166
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 166
aggcgaagaa agccaggatg agg                                             23

<210> SEQ ID NO 167
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 167
agccaggatg aggatgactg tgg                                             23

<210> SEQ ID NO 168
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 168
tgaggatgac tgtggtcttg agg                                             23

<210> SEQ ID NO 169
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 169
gaggatgact gtggtcttga ggg                                             23

<210> SEQ ID NO 170
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 170
tcttgagggc cttgcgcttc tgg                                             23

<210> SEQ ID NO 171
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 171
tgagggcctt gcgcttctgg tgg                                             23

<210> SEQ ID NO 172
<211> LENGTH: 23
<212> TYPE: DNA
<213> ORGANISM: Artificial
```

```
<220> FEATURE:
<223> OTHER INFORMATION: CXCR4 gRNA target site sequence

<400> SEQUENCE: 172
cttgcgcttc tggtggccct tgg                                            23

<210> SEQ ID NO 173
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 173
gcccttggag tgtgacagct tgg                                            23

<210> SEQ ID NO 174
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 174
ggagatgata atgcaatagc agg                                            23

<210> SEQ ID NO 175
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 175
tgataatgca atagcaggac agg                                            23

<210> SEQ ID NO 176
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 176
caggacagga tgacaatacc agg                                            23

<210> SEQ ID NO 177
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 177
acaggatgac aataccaggc agg                                            23

<210> SEQ ID NO 178
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 178
tgacaatacc aggcaggata agg                                            23
```

```
<210> SEQ ID NO 179
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 179
caaccatgat gtgctgaaac tgg                                           23

<210> SEQ ID NO 180
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 180
cacaaccacc cacaagtcat tgg                                           23

<210> SEQ ID NO 181
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 181
acaaccaccc acaagtcatt ggg                                           23

<210> SEQ ID NO 182
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 182
caaccaccca caagtcattg ggg                                           23

<210> SEQ ID NO 183
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 183
acaagtcatt ggggtagaag cgg                                           23

<210> SEQ ID NO 184
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 184
gtcatctgcc tcactgacgt tgg                                           23

<210> SEQ ID NO 185
<211> LENGTH: 23
<212> TYPE: DNA
<213> ORGANISM: Artificial
<220> FEATURE:
<223> OTHER INFORMATION: CXCR4 gRNA target site sequence
```

-continued

```
<400> SEQUENCE: 185
gacgttggca aagatgaagt cgg                                              23

<210> SEQ ID NO 186
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 186
acgttggcaa agatgaagtc ggg                                              23

<210> SEQ ID NO 187
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 187
tgaagtcggg aatagtcagc agg                                              23

<210> SEQ ID NO 188
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 188
agtcgggaat agtcagcagg agg                                              23

<210> SEQ ID NO 189
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 189
gtcgggaata gtcagcagga ggg                                              23

<210> SEQ ID NO 190
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 190
ggaatagtca gcaggagggc agg                                              23

<210> SEQ ID NO 191
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 191
gaatagtcag caggagggca ggg                                              23

<210> SEQ ID NO 192
```

```
<210> SEQ ID NO 192
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 192
ttttcagcca acagcttcct tgg                                              23

<210> SEQ ID NO 193
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 193
cttccttggc ctctgactgt tgg                                              23

<210> SEQ ID NO 194
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 194
ccttggcctc tgactgttgg tgg                                              23

<210> SEQ ID NO 195
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 195
gcctctgact gttggtggcg tgg                                              23

<210> SEQ ID NO 196
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 196
actgttggtg gcgtggacga tgg                                              23

<210> SEQ ID NO 197
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 197
tggtggcgtg gacgatggcc agg                                              23

<210> SEQ ID NO 198
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 198
```
cgtggacgat ggccaggtag cgg					23

<210> SEQ ID NO 199
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 199
gtagcggtcc agactgatga agg					23

<210> SEQ ID NO 200
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 200
ggtccagact gatgaaggcc agg					23

<210> SEQ ID NO 201
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 201
gactgatgaa ggccaggatg agg					23

<210> SEQ ID NO 202
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 202
ggatgaggac actgctgtag agg					23

<210> SEQ ID NO 203
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 203
ggttgactgt gtagatgaca tgg					23

<210> SEQ ID NO 204
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 204
tgacatggac tgccttgcat agg					23

<210> SEQ ID NO 205
<211> LENGTH: 23
<212> TYPE: DNA

```
<213> ORGANISM: Artificial
<220> FEATURE:
<223> OTHER INFORMATION: CXCR4 gRNA target site sequence

<400> SEQUENCE: 205
cccaaagtac cagtttgcca cgg                                              23

<210> SEQ ID NO 206
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 206
cacggcatca actgcccaga agg                                              23

<210> SEQ ID NO 207
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 207
acggcatcaa ctgcccagaa ggg                                              23

<210> SEQ ID NO 208
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 208
agggaagcgt gatgacaaag agg                                              23

<210> SEQ ID NO 209
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 209
gaagcgtgat gacaaagagg agg                                              23

<210> SEQ ID NO 210
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 210
cgtgatgaca aagaggaggt cgg                                              23

<210> SEQ ID NO 211
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 211
agaggaggtc ggccactgac agg                                              23
```

<210> SEQ ID NO 212
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 212
tcatgcttct cagtttcttc tgg                                              23

<210> SEQ ID NO 213
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 213
tcttctggta acccatgacc agg                                              23

<210> SEQ ID NO 214
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 214
aatgccagtt aagaagatga tgg                                              23

<210> SEQ ID NO 215
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 215
taagaagatg atggagtaga tgg                                              23

<210> SEQ ID NO 216
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 216
gaagatgatg gagtagatgg tgg                                              23

<210> SEQ ID NO 217
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 217
aagatgatgg agtagatggt ggg                                              23

<210> SEQ ID NO 218
<211> LENGTH: 23
<212> TYPE: DNA
<213> ORGANISM: Artificial
<220> FEATURE:

<223> OTHER INFORMATION: CXCR4 gRNA target site sequence

<400> SEQUENCE: 218
tgatggagta gatggtgggc agg                                           23

<210> SEQ ID NO 219
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 219
tgaaattagc attttcttca cgg                                           23

<210> SEQ ID NO 220
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 220
agcattttct tcacggaaac agg                                           23

<210> SEQ ID NO 221
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 221
gcattttctt cacggaaaca ggg                                           23

<210> SEQ ID NO 222
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 222
acggaaacag ggttccttca tgg                                           23

<210> SEQ ID NO 223
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 223 gtccctgag cccatttcct cgg                                            23

<210> SEQ ID NO 224
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 224
gaagtgtata tctgcaaaag agg                                           23

```
<210> SEQ ID NO 225
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 225
tatatctgca aaagaggcaa agg                                                 23

<210> SEQ ID NO 226
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 226
ctgcaaaaga ggcaaaggaa tgg                                                 23

<210> SEQ ID NO 227
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 227
ctctccaaag gaaagcgagg tgg                                                 23

<210> SEQ ID NO 228
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 228
atcctctcca aaggaaagcg agg                                                 23

<210> SEQ ID NO 229
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 229
agcctcaaga tcctctccaa agg                                                 23

<210> SEQ ID NO 230
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 230
cactcacctc tgtgagcaga ggg                                                 23

<210> SEQ ID NO 231
<211> LENGTH: 23
<212> TYPE: DNA
<213> ORGANISM: Artificial
<220> FEATURE:
<223> OTHER INFORMATION: CXCR4 gRNA target site sequence
```

```
<400> SEQUENCE: 231
gcactcacct ctgtgagcag agg                                           23

<210> SEQ ID NO 232
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 232
cccatcctct atgctttcct tgg                                           23

<210> SEQ ID NO 233
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 233
caagtggatt tccatcaccg agg                                           23

<210> SEQ ID NO 234
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 234
ttgagaacac tgtgcacaag tgg                                           23

<210> SEQ ID NO 235
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 235
tcctggaaat catcaagcaa ggg                                           23

<210> SEQ ID NO 236
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 236
ctcctggaaa tcatcaagca agg                                           23

<210> SEQ ID NO 237
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 237
catcgactcc ttcatcctcc tgg                                           23

<210> SEQ ID NO 238
<211> LENGTH: 23
```

<212> TYPE: DNA
<213> ORGANISM: Artificial
<220> FEATURE:
<223> OTHER INFORMATION: CXCR4 gRNA target site sequence

<400> SEQUENCE: 238
gttggctgcc ttactacatt ggg                                          23

<210> SEQ ID NO 239
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 239
tgttggctgc cttactacat tgg                                          23

<210> SEQ ID NO 240
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 240
tcctggcttt cttcgcctgt tgg                                          23

<210> SEQ ID NO 241
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 241
gaccacagtc atcctcatcc tgg                                          23

<210> SEQ ID NO 242
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 242
caagggccac cagaagcgca agg                                          23

<210> SEQ ID NO 243
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 243
tccaagctgt cacactccaa ggg                                          23

<210> SEQ ID NO 244
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 244
ctccaagctg tcacactcca agg                                               23

<210> SEQ ID NO 245
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 245
atggttggcc ttatcctgcc tgg                                               23

<210> SEQ ID NO 246
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 246
cagtttcagc acatcatggt tgg                                               23

<210> SEQ ID NO 247
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 247
gttccagttt cagcacatca tgg                                               23

<210> SEQ ID NO 248
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 248
ctaccccaat gacttgtggg tgg                                               23

<210> SEQ ID NO 249
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 249
cttctacccc aatgacttgt ggg                                               23

<210> SEQ ID NO 250
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 250
gcttctaccc caatgacttg tgg                                               23

<210> SEQ ID NO 251
<211> LENGTH: 23
<212> TYPE: DNA
<213> ORGANISM: Artificial

```
<220> FEATURE:
<223> OTHER INFORMATION: CXCR4 gRNA target site sequence

<400> SEQUENCE: 251
catctttgcc aacgtcagtg agg                                              23

<210> SEQ ID NO 252
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 252
aggtggtcta tgttggcgtc tgg                                              23

<210> SEQ ID NO 253
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 253
gctgaaaagg tggtctatgt tgg                                              23

<210> SEQ ID NO 254
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 254
gaagctgttg gctgaaaagg tgg                                              23

<210> SEQ ID NO 255
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 255
aaggaagctg ttggctgaaa agg                                              23

<210> SEQ ID NO 256
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 256
tcagaggcca aggaagctgt tgg                                              23

<210> SEQ ID NO 257
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 257
ccaccaacag tcagaggcca agg                                              23
```

<210> SEQ ID NO 258
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 258
tccacgccac caacagtcag agg                                            23

<210> SEQ ID NO 259
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 259
catcagtctg gaccgctacc tgg                                            23

<210> SEQ ID NO 260
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 260
catcctggcc ttcatcagtc tgg                                            23

<210> SEQ ID NO 261
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 261
ctacagcagt gtcctcatcc tgg                                            23

<210> SEQ ID NO 262
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 262
ctttgggaac ttcctatgca agg                                            23

<210> SEQ ID NO 263
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 263
ccgtggcaaa ctggtacttt ggg                                            23

<210> SEQ ID NO 264
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 264
gccgtggcaa actggtactt tgg                                           23

<210> SEQ ID NO 265
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 265
cagttgatgc cgtggcaaac tgg                                           23

<210> SEQ ID NO 266
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 266
cttctgggca gttgatgccg tgg                                           23

<210> SEQ ID NO 267
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 267
tgtcatcacg cttcccttct ggg                                           23

<210> SEQ ID NO 268
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 268
ttgtcatcac gcttcccttc tgg                                           23

<210> SEQ ID NO 269
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 269
gtacaggctg cacctgtcag tgg                                           23

<210> SEQ ID NO 270
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 270
gaagcatgac ggacaagtac agg                                           23

<210> SEQ ID NO 271

```
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 271
gaagaaactg agaagcatga cgg                                              23

<210> SEQ ID NO 272
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 272
ggattggtca tcctggtcat ggg                                              23

<210> SEQ ID NO 273
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 273
tggattggtc atcctggtca tgg                                              23

<210> SEQ ID NO 274
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 274
gggcaatgga ttggtcatcc tgg                                              23

<210> SEQ ID NO 275
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 275
tggcattgtg ggcaatggat tgg                                              23

<210> SEQ ID NO 276
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 276
ttaactggca ttgtgggcaa tgg                                              23

<210> SEQ ID NO 277
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 277
```
atcttcttaa ctggcattgt ggg                                          23

<210> SEQ ID NO 278
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 278
catcttctta actggcattg tgg                                          23

<210> SEQ ID NO 279
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 279
tactccatca tcttcttaac tgg                                          23

<210> SEQ ID NO 280
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 280 agggactat gactccatga agg                                           23

<210> SEQ ID NO 281
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 281
caccgaggaa atgggctcag ggg                                          23

<210> SEQ ID NO 282
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 282
acaccgagga aatgggctca ggg                                          23

<210> SEQ ID NO 283
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 283
tacaccgagg aaatgggctc agg                                          23

<210> SEQ ID NO 284
<211> LENGTH: 23
<212> TYPE: DNA

```
<213> ORGANISM: Artificial
<220> FEATURE:
<223> OTHER INFORMATION: CXCR4 gRNA target site sequence

<400> SEQUENCE: 284
gataactaca ccgaggaaat ggg                                            23

<210> SEQ ID NO 285
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 285
agataactac accgaggaaa tgg                                            23

<210> SEQ ID NO 286
<211> LENGTH: 23
<212> TYPE: DNA
<213> ORGANISM: Artificial
<220> FEATURE:
<223> OTHER INFORMATION: CXCR4 gRNA target site sequence

<400> SEQUENCE: 286
cacttcagat aactacaccg agg                                            23

<210> SEQ ID NO 287
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 287
gatggggttc agacaacagt ggaagaaa                                       28

<210> SEQ ID NO 288
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 288
gtagtaaggc agccaacagg cgaagaaa                                       28

<210> SEQ ID NO 289
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 289
aaccacccac aagtcattgg ggtagaag                                       28

<210> SEQ ID NO 290
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 290
gtttgccacg gcatcaactg cccagaag                                       28
```

<210> SEQ ID NO 291
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 291
tccattgccc acaatgccag ttaagaag                                        28

<210> SEQ ID NO 292
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 292
catcaagcaa gggtgtgagt ttgagaac                                        28

<210> SEQ ID NO 293
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 293
gctgtcacac tccaagggcc accagaag                                        28

<210> SEQ ID NO 294
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 294
tcatgggtta ccagaagaaa ctgagaag                                        28

<210> SEQ ID NO 295
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 295
catcctggtc atgggttacc agaagaaa                                        28

<210> SEQ ID NO 296
<211> LENGTH: 28
<212> TYPE: DNA
<213> ORGANISM: Artificial
<220> FEATURE:
<223> OTHER INFORMATION: CXCR4 gRNA target site sequence

<400> SEQUENCE: 296
ggtcatcctg gtcatgggtt accagaag                                        28

<210> SEQ ID NO 297
<211> LENGTH: 28
<212> TYPE: DNA
<213> ORGANISM: Artificial
<220> FEATURE:

-continued

<223> OTHER INFORMATION: CXCR4 gRNA target site sequence

<400> SEQUENCE: 297
atgaaggaac cctgtttccg tgaagaaa                                           28

<210> SEQ ID NO 298
<211> LENGTH: 1368
<212> TYPE: PRT
<213> ORGANISM: Unknown
<220> FEATURE:
<223> OTHER INFORMATION: CAS protein

<400> SEQUENCE: 298

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335
```

```
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
```

-continued

```
             755                 760                 765
Thr Thr Gln Lys Gly Gln Lys Asn Ser Arg Glu Arg Met Lys Arg Ile
         770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
                 805                 810                 815
Gln Asn Gly Arg Asp Met Tyr Val Asp Gln Glu Leu Asp Ile Asn Arg
             820                 825                 830
Leu Ser Asp Tyr Asp Val Asp His Ile Val Pro Gln Ser Phe Leu Lys
             835                 840                 845
Asp Asp Ser Ile Asp Asn Lys Val Leu Thr Arg Ser Asp Lys Asn Arg
         850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                 885                 890                 895
Phe Asp Asn Leu Thr Lys Ala Glu Arg Gly Gly Leu Ser Glu Leu Asp
             900                 905                 910
Lys Ala Gly Phe Ile Lys Arg Gln Leu Val Glu Thr Arg Gln Ile Thr
             915                 920                 925
Lys His Val Ala Gln Ile Leu Asp Ser Arg Met Asn Thr Lys Tyr Asp
         930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                 965                 970                 975
Glu Ile Asn Asn Tyr His His Ala His Asp Ala Tyr Leu Asn Ala Val
             980                 985                 990
Val Gly Thr Ala Leu Ile Lys Lys Tyr Pro Lys Leu Glu Ser Glu Phe
             995                 1000                1005
Val Tyr Gly Asp Tyr Lys Val Tyr Asp Val Arg Lys Met Ile Ala
         1010                1015                1020
Lys Ser Glu Gln Glu Ile Gly Lys Ala Thr Ala Lys Tyr Phe Phe
         1025                1030                1035
Tyr Ser Asn Ile Met Asn Phe Phe Lys Thr Glu Ile Thr Leu Ala
         1040                1045                1050
Asn Gly Glu Ile Arg Lys Arg Pro Leu Ile Glu Thr Asn Gly Glu
         1055                1060                1065
Thr Gly Glu Ile Val Trp Asp Lys Gly Arg Asp Phe Ala Thr Val
         1070                1075                1080
Arg Lys Val Leu Ser Met Pro Gln Val Asn Ile Val Lys Lys Thr
         1085                1090                1095
Glu Val Gln Thr Gly Gly Phe Ser Lys Glu Ser Ile Leu Pro Lys
         1100                1105                1110
Arg Asn Ser Asp Lys Leu Ile Ala Arg Lys Lys Asp Trp Asp Pro
         1115                1120                1125
Lys Lys Tyr Gly Gly Phe Asp Ser Pro Thr Val Ala Tyr Ser Val
         1130                1135                1140
Leu Val Val Ala Lys Val Glu Lys Gly Lys Ser Lys Lys Leu Lys
         1145                1150                1155
Ser Val Lys Glu Leu Leu Gly Ile Thr Ile Met Glu Arg Ser Ser
         1160                1165                1170
```

-continued

```
Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 299
<211> LENGTH: 20
<212> TYPE: DNA
<213> ORGANISM: Artificial
<220> FEATURE:
<223> OTHER INFORMATION: gRNA

<400> SEQUENCE: 299
taaattcttt gctgacctgc                                          20

<210> SEQ ID NO 300
<211> LENGTH: 20
<212> TYPE: DNA
<213> ORGANISM: Artificial
<220> FEATURE:
<223> OTHER INFORMATION: gRNA

<400> SEQUENCE: 300
tagatccatt cctatgactg                                          20

<210> SEQ ID NO 301
<211> LENGTH: 20
<212> TYPE: DNA
<213> ORGANISM: Artificial
<220> FEATURE:
<223> OTHER INFORMATION: gRNA

<400> SEQUENCE: 301
cttcagtctg ataaaatcta                                          20

<210> SEQ ID NO 302
<211> LENGTH: 20
```

```
<212> TYPE: DNA
<213> ORGANISM: Artificial
<220> FEATURE:
<223> OTHER INFORMATION: gRNA

<400> SEQUENCE: 302
tttgatgtaa tccagcaggt                                               20

<210> SEQ ID NO 303
<211> LENGTH: 20
<212> TYPE: DNA
<213> ORGANISM: Artificial
<220> FEATURE:
<223> OTHER INFORMATION: gRNA

<400> SEQUENCE: 303
cacagagggc tacaatgtga                                               20

<210> SEQ ID NO 304
<211> LENGTH: 23
<212> TYPE: DNA
<213> ORGANISM: Artificial
<220> FEATURE:
<223> OTHER INFORMATION: Target site sequence with NGG

<400> SEQUENCE: 304
gtagagcgga ggcaggaggc ggg                                           23

<210> SEQ ID NO 305
<211> LENGTH: 23
<212> TYPE: DNA
<213> ORGANISM: Artificial
<220> FEATURE:
<223> OTHER INFORMATION: Target site sequence with NGG

<400> SEQUENCE: 305
gtgagtagag cggaggcagg agg                                           23

<210> SEQ ID NO 306
<211> LENGTH: 23
<212> TYPE: DNA
<213> ORGANISM: Artificial
<220> FEATURE:
<223> OTHER INFORMATION: Target site sequence with NGG

<400> SEQUENCE: 306
ggtgttcatc tttggttttg tgg                                           23

<210> SEQ ID NO 307
<211> LENGTH: 23
<212> TYPE: DNA
<213> ORGANISM: Artificial
<220> FEATURE:
<223> OTHER INFORMATION: Target site sequence with NGG

<400> SEQUENCE: 307
gtgttcatct ttggttttgt ggg                                           23

<210> SEQ ID NO 308
<211> LENGTH: 23
<212> TYPE: DNA
<213> ORGANISM: Artificial
<220> FEATURE:
<223> OTHER INFORMATION: Target site sequence with NGG

<400> SEQUENCE: 308
```

```
ggacagtaag aaggaaaaac agg                                              23

<210> SEQ ID NO 309
<211> LENGTH: 23
<212> TYPE: DNA
<213> ORGANISM: Artificial
<220> FEATURE:
<223> OTHER INFORMATION: Target site sequence with NGG

<400> SEQUENCE: 309
gctgccgccc agtgggactt tgg                                              23

<210> SEQ ID NO 310
<211> LENGTH: 23
<212> TYPE: DNA
<213> ORGANISM: Artificial
<220> FEATURE:
<223> OTHER INFORMATION: Target site sequence with NGG

<400> SEQUENCE: 310
gcagcatagt gagcccagaa ggg                                              23

<210> SEQ ID NO 311
<211> LENGTH: 23
<212> TYPE: DNA
<213> ORGANISM: Artificial
<220> FEATURE:
<223> OTHER INFORMATION: Target site sequence with NGG

<400> SEQUENCE: 311
ggcagcatag tgagcccaga agg                                              23

<210> SEQ ID NO 312
<211> LENGTH: 23
<212> TYPE: DNA
<213> ORGANISM: Artificial
<220> FEATURE:
<223> OTHER INFORMATION: Target site sequence with NGG

<400> SEQUENCE: 312
ggtacctatc gattgtcagg agg                                              23

<210> SEQ ID NO 313
<211> LENGTH: 23
<212> TYPE: DNA
<213> ORGANISM: Artificial
<220> FEATURE:
<223> OTHER INFORMATION: Target site sequence with NGG

<400> SEQUENCE: 313
gtttgcttta aaagccagga cgg                                              23

<210> SEQ ID NO 314
<211> LENGTH: 23
<212> TYPE: DNA
<213> ORGANISM: Artificial
<220> FEATURE:
<223> OTHER INFORMATION: Target site sequence with NGG

<400> SEQUENCE: 314
ggtgacaagt gtgatcactt ggg                                              23

<210> SEQ ID NO 315
<211> LENGTH: 23
<212> TYPE: DNA
<213> ORGANISM: Artificial
```

```
<220> FEATURE:
<223> OTHER INFORMATION: Target site sequence with NGG

<400> SEQUENCE: 315
gacaagtgtg atcacttggg tgg                                              23

<210> SEQ ID NO 316
<211> LENGTH: 23
<212> TYPE: DNA
<213> ORGANISM: Artificial
<220> FEATURE:
<223> OTHER INFORMATION: Target site sequence with NGG

<400> SEQUENCE: 316
gctgtgtttg cgtctctccc agg                                              23

<210> SEQ ID NO 317
<211> LENGTH: 23
<212> TYPE: DNA
<213> ORGANISM: Artificial
<220> FEATURE:
<223> OTHER INFORMATION: Target site sequence with NGG

<400> SEQUENCE: 317
gatctggtaa agatgattcc tgg                                              23

<210> SEQ ID NO 318
<211> LENGTH: 23
<212> TYPE: DNA
<213> ORGANISM: Artificial
<220> FEATURE:
<223> OTHER INFORMATION: Target site sequence with NGG

<400> SEQUENCE: 318
gtatggaaaa tgagagctgc agg                                              23

<210> SEQ ID NO 319
<211> LENGTH: 23
<212> TYPE: DNA
<213> ORGANISM: Artificial
<220> FEATURE:
<223> OTHER INFORMATION: Target site sequence with NGG

<400> SEQUENCE: 319
gacattaaag atagtcatct tgg                                              23

<210> SEQ ID NO 320
<211> LENGTH: 23
<212> TYPE: DNA
<213> ORGANISM: Artificial
<220> FEATURE:
<223> OTHER INFORMATION: Target site sequence with NGG

<400> SEQUENCE: 320
ggtcctgccg ctgcttgtca tgg                                              23

<210> SEQ ID NO 321
<211> LENGTH: 23
<212> TYPE: DNA
<213> ORGANISM: Artificial
<220> FEATURE:
<223> OTHER INFORMATION: Target site sequence with NGG

<400> SEQUENCE: 321
gtcatggtca tctgctactc ggg                                              23
```

```
<210> SEQ ID NO 322
<211> LENGTH: 23
<212> TYPE: DNA
<213> ORGANISM: Artificial
<220> FEATURE:
<223> OTHER INFORMATION: Target site sequence with NGG

<400> SEQUENCE: 322
gaatcctaaa aactctgctt cgg                                              23

<210> SEQ ID NO 323
<211> LENGTH: 23
<212> TYPE: DNA
<213> ORGANISM: Artificial
<220> FEATURE:
<223> OTHER INFORMATION: Target site sequence with NGG

<400> SEQUENCE: 323
ggtgtcgaaa tgagaagaag agg                                              23

<210> SEQ ID NO 324
<211> LENGTH: 23
<212> TYPE: DNA
<213> ORGANISM: Artificial
<220> FEATURE:
<223> OTHER INFORMATION: Target site sequence with NGG

<400> SEQUENCE: 324
gacaccgaag cagagttttt agg                                              23

<210> SEQ ID NO 325
<211> LENGTH: 23
<212> TYPE: DNA
<213> ORGANISM: Artificial
<220> FEATURE:
<223> OTHER INFORMATION: Target site sequence with NGG

<400> SEQUENCE: 325
gaaatgagaa gaagaggcac agg                                              23

<210> SEQ ID NO 326
<211> LENGTH: 23
<212> TYPE: DNA
<213> ORGANISM: Artificial
<220> FEATURE:
<223> OTHER INFORMATION: Target site sequence with NGG

<400> SEQUENCE: 326
gattgtttat tttctcttct ggg                                              23

<210> SEQ ID NO 327
<211> LENGTH: 23
<212> TYPE: DNA
<213> ORGANISM: Artificial
<220> FEATURE:
<223> OTHER INFORMATION: Target site sequence with NGG

<400> SEQUENCE: 327
gagaaaataa acaatcatga tgg                                              23

<210> SEQ ID NO 328
<211> LENGTH: 23
<212> TYPE: DNA
<213> ORGANISM: Artificial
<220> FEATURE:
<223> OTHER INFORMATION: Target site sequence with NGG
```

<400> SEQUENCE: 328
gcttttggaa gaagactaag agg                                    23

<210> SEQ ID NO 329
<211> LENGTH: 23
<212> TYPE: DNA
<213> ORGANISM: Artificial
<220> FEATURE:
<223> OTHER INFORMATION: Target site sequence with NGG

<400> SEQUENCE: 329
gtaaactgag cttgctcgct cgg                                    23

<210> SEQ ID NO 330
<211> LENGTH: 23
<212> TYPE: DNA
<213> ORGANISM: Artificial
<220> FEATURE:
<223> OTHER INFORMATION: Target site sequence with NGG

<400> SEQUENCE: 330
ggggagcagg aaatatctgt ggg                                    23

<210> SEQ ID NO 331
<211> LENGTH: 23
<212> TYPE: DNA
<213> ORGANISM: Artificial
<220> FEATURE:
<223> OTHER INFORMATION: Target site sequence with NGG

<400> SEQUENCE: 331
acaatgtgtc aactcttgac agg                                    23

<210> SEQ ID NO 332
<211> LENGTH: 23
<212> TYPE: DNA
<213> ORGANISM: Artificial
<220> FEATURE:
<223> OTHER INFORMATION: Target site sequence with NGG

<400> SEQUENCE: 332
tcactatgct gccgcccagt ggg                                    23

<210> SEQ ID NO 333
<211> LENGTH: 23
<212> TYPE: DNA
<213> ORGANISM: Artificial
<220> FEATURE:
<223> OTHER INFORMATION: Target site sequence with NGG

<400> SEQUENCE: 333
ggtacctatc gattgtcagg agg                                    23

<210> SEQ ID NO 334
<211> LENGTH: 20
<212> TYPE: DNA
<213> ORGANISM: Artificial
<220> FEATURE:
<223> OTHER INFORMATION: gRNA

<400> SEQUENCE: 334
gtcttgctcg agatgtgatg                                        20

<210> SEQ ID NO 335

```
<211> LENGTH: 47
<212> TYPE: DNA
<213> ORGANISM: Artificial
<220> FEATURE:
<223> OTHER INFORMATION: target sequence

<400> SEQUENCE: 335
tcccttcctg cctcatttca ggtgaataca tcaagacctg gaggcca            47

<210> SEQ ID NO 336
<211> LENGTH: 47
<212> TYPE: DNA
<213> ORGANISM: Artificial
<220> FEATURE:
<223> OTHER INFORMATION: target sequence

<400> SEQUENCE: 336
tcccttcctg cctcatttca ggtgaataca tcaagacctg gaggcca            47

<210> SEQ ID NO 337
<211> LENGTH: 47
<212> TYPE: DNA
<213> ORGANISM: Artificial
<220> FEATURE:
<223> OTHER INFORMATION: target sequence

<400> SEQUENCE: 337
tgctggctcg gctgccctga ggttgctcaa tcaagcacag gtttcaa            47

<210> SEQ ID NO 338
<211> LENGTH: 47
<212> TYPE: DNA
<213> ORGANISM: Artificial
<220> FEATURE:
<223> OTHER INFORMATION: target sequence

<400> SEQUENCE: 338
tgctggctcg gctgccctga ggttgctcaa tcaagcacag gtttcaa            47

<210> SEQ ID NO 339
<211> LENGTH: 47
<212> TYPE: DNA
<213> ORGANISM: Artificial
<220> FEATURE:
<223> OTHER INFORMATION: target sequence

<400> SEQUENCE: 339
taacagcgat gctgaccccc tgtgcctcta ccacttctat gaccaga            47

<210> SEQ ID NO 340
<211> LENGTH: 47
<212> TYPE: DNA
<213> ORGANISM: Artificial
<220> FEATURE:
<223> OTHER INFORMATION: target sequence

<400> SEQUENCE: 340
cgatgctgac cccctgtgcc tctaccactt ctatgaccag atggacc            47

<210> SEQ ID NO 341
<211> LENGTH: 49
<212> TYPE: DNA
<213> ORGANISM: Artificial
<220> FEATURE:
<223> OTHER INFORMATION: target sequence

<400> SEQUENCE: 341
```
tggtccttgc tgtgttctct gcggtgcttg gctccctgca gtttgggta          49

<210> SEQ ID NO 342
<211> LENGTH: 49
<212> TYPE: DNA
<213> ORGANISM: Artificial
<220> FEATURE:
<223> OTHER INFORMATION: target sequence

<400> SEQUENCE: 342
tggtccttgc tgtgttctct gcggtgcttg gctccctgca gtttgggta          49

<210> SEQ ID NO 343
<211> LENGTH: 47
<212> TYPE: DNA
<213> ORGANISM: Artificial
<220> FEATURE:
<223> OTHER INFORMATION: target sequence

<400> SEQUENCE: 343
tgggcgacag atgcgaaaga aacgagttcc agtgccaaga cgggaaa            47

<210> SEQ ID NO 344
<211> LENGTH: 47
<212> TYPE: DNA
<213> ORGANISM: Artificial
<220> FEATURE:
<223> OTHER INFORMATION: target sequence

<400> SEQUENCE: 344
gaaacgagtt ccagtgccaa gacgggaaat gcatctccta caagtgg            47

<210> SEQ ID NO 345
<211> LENGTH: 48
<212> TYPE: DNA
<213> ORGANISM: Artificial
<220> FEATURE:
<223> OTHER INFORMATION: target sequence

<400> SEQUENCE: 345
tcagagagga cactgcagtt gtccgtgcta gtagccttcg cttctgga           48

<210> SEQ ID NO 346
<211> LENGTH: 48
<212> TYPE: DNA
<213> ORGANISM: Artificial
<220> FEATURE:
<223> OTHER INFORMATION: target sequence

<400> SEQUENCE: 346
tcagagagga cactgcagtt gtccgtgcta gtagccttcg cttctgga           48

<210> SEQ ID NO 347
<211> LENGTH: 47
<212> TYPE: DNA
<213> ORGANISM: Artificial
<220> FEATURE:
<223> OTHER INFORMATION: target sequence

<400> SEQUENCE: 347
tgatgatctc agaggctcag tatccttgtc ctgggttgga gatagca            47

<210> SEQ ID NO 348
<211> LENGTH: 47
<212> TYPE: DNA

```
<213> ORGANISM: Artificial
<220> FEATURE:
<223> OTHER INFORMATION: target sequence

<400> SEQUENCE: 348
tgatgatctc agaggctcag tatccttgtc ctgggttgga gatagca                47

<210> SEQ ID NO 349
<211> LENGTH: 49
<212> TYPE: DNA
<213> ORGANISM: Artificial
<220> FEATURE:
<223> OTHER INFORMATION: target sequence

<400> SEQUENCE: 349
tggtaattat gacttttgga cagtccaagc tatatcgaag gtgagatca              49

<210> SEQ ID NO 350
<211> LENGTH: 49
<212> TYPE: DNA
<213> ORGANISM: Artificial
<220> FEATURE:
<223> OTHER INFORMATION: target sequence

<400> SEQUENCE: 350
tggtaattat gacttttgga cagtccaagc tatatcgaag gtgagatca              49

<210> SEQ ID NO 351
<211> LENGTH: 47
<212> TYPE: DNA
<213> ORGANISM: Artificial
<220> FEATURE:
<223> OTHER INFORMATION: target sequence

<400> SEQUENCE: 351
tcccttcctg cctcatttca ggtgaataca tcaagacctg gaggcca                47

<210> SEQ ID NO 352
<211> LENGTH: 47
<212> TYPE: DNA
<213> ORGANISM: Artificial
<220> FEATURE:
<223> OTHER INFORMATION: target sequence

<400> SEQUENCE: 352
tcccttcctg cctcatttca ggtgaataca tcaagacctg gaggcca                47

<210> SEQ ID NO 353
<211> LENGTH: 47
<212> TYPE: DNA
<213> ORGANISM: Artificial
<220> FEATURE:
<223> OTHER INFORMATION: target sequence

<400> SEQUENCE: 353
ctatgccctg cctcatttca ggtgaagatg aaatccctgg agcttgg                47
```

METHOD OF MAKING A DELETION IN A TARGET SEQUENCE IN ISOLATED PRIMARY CELLS USING CAS9 AND TWO GUIDE RNAS

RELATED APPLICATIONS

This application is a continuation of PCT Application No. PCT/US2014/033082, filed Apr. 4, 2014, which claims the benefit of U.S. Provisional Application Ser. No. 61/808,594, filed Apr. 4, 2013, the teachings of which are incorporated herein by reference in their entirety.

GOVERNMENT SUPPORT

This invention was made with government support under HL107440, R01-HL118744, R00-HL098364 and R01-DK095384 awarded by the National Institutes of Health. The government has certain rights in the invention.

BACKGROUND OF THE INVENTION

Clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus a $(N)_{20}$NGG target DNA sequence). This results in a double-strand break three nucleotides upstream of the NGG motif. The double strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, CRISPR/Cas systems could be useful tools for therapeutic applications, but unfortunately prior published reports have demonstrated an efficiency of allele targeting of only 2%-4% in human stem cells (Mali et al., *Science* 339:823-826 (2013)).

SUMMARY OF THE INVENTION

Work described herein demonstrates methods of allele targeting using CRISPR/Cas systems resulting in mutant cells with efficiencies of up to 80%. In particular, work described herein surprisingly and unexpectedly demonstrates that a multiple guide strategy (e.g., using two or more ribonucleic acids which guide Cas protein to and hybridize to a target polynucleotide sequence) efficiently and effectively deletes target polynucleotide sequences (e.g., B2M, HPRT, CCR5 and/or CXCR4) in primary somatic cells (e.g., human blood cells, e.g., CD34+ and T cells), in contrast to a single guide strategy which has been demonstrated by the inventors to efficiently delete target polynucleotide sequences in cell lines (e.g., 293T) but not in primary somatic cells. These vastly improved methods permit CRISPR/Cas systems to be utilized effectively for the first time for therapeutic purposes. Methods of delivery of CRISPR/Cas systems to human stem cells are provided. In addition, methods of specifically identifying useful RNA guide sequences are provided, along with particular guide sequences useful in targeting specific genes (e.g., B2M, HPRT, CCR5 and/or CXCR4). Moreover, methods of treatment (e.g., methods of treating HIV infection) utilizing the compositions and methods disclosed herein are provided.

In some aspects, the present invention provides a method for altering a target polynucleotide sequence in a cell comprising contacting the polynucleotide sequence with a clustered regularly interspaced short palindromic repeats-associated (Cas) protein and from one to two ribonucleic acids, wherein the ribonucleic acids direct Cas protein to and hybridize to a target motif of the target polynucleotide sequence, wherein the target polynucleotide sequence is cleaved, and wherein the efficiency of alteration of cells that express Cas protein is from about 50% to about 80%.

In some aspects, the present invention provides a method for treating or preventing a disorder associated with expression of a polynucleotide sequence in a subject, the method comprising (a) altering a target polynucleotide sequence in a cell ex vivo by contacting the polynucleotide sequence with a clustered regularly interspaced short palindromic repeats-associated (Cas) protein and from one to two ribonucleic acids, wherein the ribonucleic acids direct Cas protein to and hybridize to a target motif of the target polynucleotide sequence, wherein the target polynucleotide sequence is cleaved, and wherein the efficiency of alteration of cells that express Cas protein is from about 50% to about 80%, and (b) introducing the cell into the subject, thereby treating or preventing a disorder associated with expression of the polynucleotide sequence.

In some aspects, the present invention provides a method for simultaneously altering multiple target polynucleotide sequences in a cell comprising contacting the polynucleotide sequences with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 50% to about 80%.

In some aspects, the present invention provides a method for treating or preventing a disorder associated with expression of polynucleotide sequences in a subject, the method comprising (a) altering target polynucleotide sequences in a cell ex vivo by contacting the polynucleotide sequences with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 50% to about 80%, and (b) introducing the cell into the subject, thereby treating or preventing a disorder associated with expression of the polynucleotide sequences.

In some embodiments, the Cas protein is *Streptococcus pyogenes* Cas9 protein or a functional portion thereof. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional domains form a complex.

In some embodiments, the Cas protein is Cas9 protein from any bacterial species or functional portion thereof. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional domains form a complex.

In some embodiments, the Cas protein is complexed with the one to two ribonucleic acids. In some embodiments, the Cas protein is complexed with the multiple ribonucleic acids.

In some embodiments, the target motif is a 20-nucleotide DNA sequence. In some embodiments, each target motif is a 20-nucleotide DNA sequence. In some embodiments, the target motif is a 20-nucleotide DNA sequence beginning with G and immediately precedes an NGG motif recognized by the Cas protein. In some embodiments, each target motif is a 20-nucleotide DNA sequence beginning with G and immediately precedes an NGG motif recognized by the Cas protein. In some embodiments, the target motif is a 20-nucleotide DNA sequence and immediately precedes an NGG motif recognized by the Cas protein. In some embodiments, each target motif is a 20-nucleotide DNA sequence and immediately precedes an NGG motif recognized by the Cas protein. In some embodiments, the target motif is $G(N)_{19}NGG$. In some embodiments, each target motif is $G(N)_{19}NGG$. In some embodiments, the target motif is $(N)_{20}NGG$. In some embodiments, each target motif is $(N)_{20}NGG$.

In some embodiments, the target polynucleotide sequence is cleaved such that a double-strand break results. In some embodiments, each target polynucleotide sequence is cleaved such that a double-strand break results. In some embodiments, the target polynucleotide sequence is cleaved such that a single-strand break results. In some embodiments, each target polynucleotide sequence is cleaved such that a single-strand break results.

In some embodiments, the alteration is an indel. In some embodiments, the alteration results in reduced expression of the target polynucleotide sequence. In some embodiments, the alteration results in reduced expression of the target polynucleotide sequences. In some embodiments, the alteration results in a knock out of the target polynucleotide sequence.

In some embodiments, the alteration results in a knock out of the target polynucleotide sequences. In some embodiments, the alteration results in correction of the target polynucleotide sequence from an undesired sequence to a desired sequence. In some embodiments, the alteration results in correction of the target polynucleotide sequences from undesired sequences to desired sequences. In some embodiments, the alteration is a homozygous alteration. In some embodiments, each alteration is a homozygous alteration.

In some embodiments, subsequent to cleavage of the target polynucleotide sequence, homology-directed repair occurs. In some embodiments, homology-directed repair is performed using an exogenously introduced DNA repair template. In some embodiments, the exogenously introduced DNA repair template is single-stranded. In some embodiments, the exogenously introduced DNA repair template is double-stranded.

In some embodiments, subsequent to cleavage of the target polynucleotide sequences, homology-directed repair occurs. In some embodiments, homology-directed repair is performed using an exogenously introduced DNA repair template. In some embodiments, the exogenously introduced DNA repair template is single-stranded. In some embodiments, the exogenously introduced DNA repair template is double-stranded.

In some embodiments, the cell is a peripheral blood cell. In some embodiments, the cell is a stem cell or a pluripotent cell. In some embodiments, the cell is a hematopoietic stem cell. In some embodiments, the cell is a $CD34^+$ cell. In some embodiments, the cell is a $CD34^+$ mobilized peripheral blood cell. In some embodiments, the cell is a $CD34^+$ cord blood cell. In some embodiments, the cell is a $CD34^+$ bone marrow cell. In some embodiments, the cell is a $CD34^+$ $CD38$-Lineage-$CD90^+CD45RA^-$ cell. In some embodiments, the cell is a hepatocyte.

In some embodiments, the target polynucleotide sequence is CCR5. In some embodiments, at least one of the one to two ribonucleic acids comprises a sequence selected from the group consisting of the ribonucleic acid sequences of FIG. 1. In some embodiments, at least one of the one to two ribonucleic acids comprises a sequence with a single nucleotide mismatch to a sequence selected from the group consisting of the ribonucleic acid sequences of FIG. 1.

In some embodiments, the target polynucleotide sequence is CXCR4. In some embodiments, at least one of the one to two ribonucleic acids comprises a sequence selected from the group consisting of the ribonucleic acid sequences of FIG. 2. In some embodiments, at least one of the one to two ribonucleic acids comprises a sequence with a single nucleotide mismatch to a sequence selected from the group consisting of the ribonucleic acid sequences of FIG. 2.

In some embodiments, the target polynucleotide sequences comprise multiple different portions of CCR5. In some embodiments, each of the multiple ribonucleic acids comprises a different sequence selected from the group consisting of the ribonucleic acid sequences of FIG. 1. In some embodiments, each of the multiple ribonucleic acids comprises a sequence with a single nucleotide mismatch to a different sequence selected from the group consisting of the ribonucleic acid sequences of FIG. 1.

In some embodiments, the target polynucleotide sequences comprise multiple different portions of CXCR4 In some embodiments, each of the multiple ribonucleic acids comprises a different sequence selected from the group consisting of the ribonucleic acid sequences of FIG. 2. In some embodiments, each of the multiple ribonucleic acids comprises a sequence with a single nucleotide mismatch to a different sequence selected from the group consisting of the ribonucleic acid sequences of FIG. 2.

In some embodiments, the target polynucleotide sequences comprise at least a portion of CCR5 and at least a portion of CXCR4. In some embodiments, each of the multiple ribonucleic acids comprises a different sequence selected from the group consisting of the ribonucleic acid sequences of FIG. 1 and the ribonucleic acid sequences of FIG. 2. In some embodiments, each of the multiple ribonucleic acids comprises a sequence with a single nucleotide mismatch to a different sequence selected from the group consisting of the ribonucleic acid sequences of FIG. 1 and the ribonucleic acid sequences of FIG. 2.

In some embodiments, the disorder is a genetic disorder. In some embodiments, the disorder is a monogenic disorder. In some embodiments, the disorder is human immunodeficiency virus (HIV) infection. In some embodiments, the disorder is acquired immunodeficiency syndrome (AIDS).

In some embodiments, the one to two ribonucleic acids are designed to hybridize to a target motif immediately adjacent to a deoxyribonucleic acid motif recognized by the Cas protein. In some embodiments, each of the one to two ribonucleic acids are designed to hybridize to target motifs immediately adjacent to deoxyribonucleic acid motifs recognized by the Cas protein which flank a mutant allele located between the target motifs. In some embodiments, the multiple ribonucleic acids are designed to hybridize to target motifs immediately adjacent to deoxyribonucleic acid motifs recognized by the Cas protein. In some embodiments, the multiple ribonucleic acids are designed to hybridize to target motifs immediately adjacent to deoxyribonucleic acid motifs recognized by the Cas protein which flank mutant alleles located between the target motifs. In some embodiments, the one to two ribonucleic acids are selected to minimize hybridization with nucleic acid sequences other than the target polynucleotide sequence. In some embodiments, the multiple ribonucleic acids are selected to minimize hybridization with nucleic acid sequences other than the target polynucleotide sequence.

In some embodiments, the target motif is selected such that it contains at least two mismatches when compared with all other genomic nucleotide sequences in the cell. In some embodiments, each target motif is selected such that it contains at least two mismatches when compared with all other genomic nucleotide sequences in the cell. In some embodiments, the target motif is selected such that it contains at least one mismatch when compared with all other genomic nucleotide sequences in the cell.

In some embodiments, the target motif is selected such that it contains at least one mismatch when compared with all other genomic nucleotide sequences in the cell. In some embodiments, the one to two ribonucleic acids hybridize to a target motif that it contains at least two mismatches when compared with all other genomic nucleotide sequences in the cell.

In some embodiments, each of the multiple ribonucleic acids hybridize to target motifs that contain at least two mismatches when compared with all other genomic nucleotide sequences in the cell. In some embodiments, the one to two ribonucleic acids hybridize to a target motif that contains at least one mismatch when compared with all other genomic nucleotide sequences in the cell. In some embodiments, each of the multiple ribonucleic acids hybridize to target motifs that contain at least one mismatch when compared with all other genomic nucleotide sequences in the cell.

In some embodiments, the efficiency of alteration at each loci is from about 50% to about 80%. In some embodiments, the efficiency of alteration is at least about 5%. In some embodiments, the efficiency of alteration is at least about 10%. In some embodiments, the efficiency of alteration is from about 50% to about 80%.

In some embodiments, the Cas protein is encoded by a modified nucleic acid. In some embodiments, the modified nucleic acid comprises a ribonucleic acid containing at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. In some embodiments, at least one of the ribonucleic acids is a modified ribonucleic acid comprising one to two modified nucleotides selected from the group consisting of pseudouridine, S-methylcytodine, 7-thin-uridine, 5-methyluridine-5'-triphosphate, 4-thiouridine-5'-triphosphate, 5,6-dihydrouridine-5'-triphosphate, and 5-azauridine-5'-triphosphate.

In some embodiments, any of the Cas protein or the ribonucleic acids are expressed from a plasmid.

In some embodiments, any of the Cas protein or the ribonucleic acids are expressed using a promoter optimized for increased expression in stem cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter.

In some embodiments, the method further comprises selecting cells that express the Cas protein. In some embodiments, selecting cells comprises FACS. In some embodiments, FACs is used to select cells which co-express Cas and a fluorescent protein selected from the group consisting of green fluorescent protein and red fluorescent protein.

In some aspects, the present invention provides a method for altering a target polynucleotide sequence in a cell comprising contacting the polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target polynucleotide sequence, wherein the target polynucleotide sequence is cleaved, and wherein the efficiency of alteration of cells that express Cas protein is from about 8% to about 80%.

In some aspects, the present invention provides a method for treating or preventing a disorder associated with expression of a polynucleotide sequence in a subject, the method comprising (a) altering a target polynucleotide sequence in a cell ex vivo by contacting the polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target polynucleotide sequence, wherein the target polynucleotide sequence is cleaved, and wherein the efficiency of alteration is from about 8% to about 80%, and (b) introducing the cell into the subject, thereby treating or preventing a disorder associated with expression of the polynucleotide sequence.

In some aspects, the present invention provides a method for simultaneously altering multiple target polynucleotide sequences in a cell comprising contacting the polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 8% to about 80%.

In some aspects, the present invention provides a method for treating or preventing a disorder associated with expression of polynucleotide sequences in a subject, the method comprising (a) altering target polynucleotide sequences in a cell ex vivo by contacting the polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 8% to about 80%, and (b) introducing the cell into the subject, thereby treating or preventing a disorder associated with expression of the polynucleotide sequences.

In some aspects, the present invention provides a composition comprising at least one ribonucleic acid having a sequence selected from the group consisting of the ribonucleic acid sequences of FIG. 1.

In some aspects, the present invention provides a composition comprising at least one ribonucleic acid comprising a sequence with a single nucleotide mismatch to a sequence selected from the group consisting of the ribonucleic acid sequences of FIG. 1.

In some aspects, the present invention provides a composition comprising at least one ribonucleic acid having a sequence selected from the group consisting of the ribonucleic acid sequences of FIG. 2.

In some aspects, the present invention provides a composition comprising at least one ribonucleic acid comprising a sequence with a single nucleotide mismatch to a sequence selected from the group consisting of the ribonucleic acid sequences of FIG. 2.

In some aspects, the present invention provides a composition comprising at least one ribonucleic acid having a sequence selected from the group consisting of the ribonucleic acid sequences of FIG. 1, the ribonucleic acid sequences of FIG. 2, a sequence with a single nucleotide mismatch to a ribonucleic acid sequence of FIG. 1, and a sequence with a single nucleotide mismatch to a ribonucleic acid sequences of FIG. 2.

In some embodiments, the composition further comprises a nucleic acid sequence encoding a Cas protein. In some embodiments, the composition further comprises a nucleic acid sequence encoding a Cas9 protein or a functional portion thereof. In some embodiments, the nucleic acid comprises a modified ribonucleic acid comprising at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 1.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 2.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 1.

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 2.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 1, the ribonucleic acid sequences of FIG. 2, a sequence with a single nucleotide mismatch to a ribonucleic acid sequence of FIG. 1, and a sequence with a single nucleotide mismatch to a ribonucleic acid sequences of FIG. 2.

In some embodiments, the composition further comprises a nucleic acid sequence encoding a fluorescent protein selected from the group consisting of green fluorescent protein and red fluorescent protein.

In some embodiments, the composition further comprises a promoter operably linked to the chimeric nucleic acid. In some embodiments, the promoter is optimized for increased expression in human stem cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter.

In some embodiments, the Cas protein comprises a Cas9 protein or a functional portion thereof.

In some aspects, the present invention provides a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 1, the ribonucleic acid sequences of FIG. 2, a sequence with a single nucleotide mismatch to a ribonucleic acid sequence of FIG. 1, and a sequence with a single nucleotide mismatch to a ribonucleic acid sequences of FIG. 2. In some embodiments, the kit further comprises one or more cell lines, cultures, or populations selected from the group consisting of human pluripotent cells, primary human cells, and non-transformed cells. In some embodiments, the kit further comprises a DNA repair template.

In some embodiments, the cell comprises a primary cell. In some embodiments, the cell comprises a primary somatic cell. In some embodiments, the cell comprises an autologous primary somatic cell. In some embodiments, the cell comprises an allogeneic primary somatic cell. In some embodiments, the target polynucleotide sequence is B2M. In some embodiments, at least one of the one to two ribonucleic acids comprises a sequence optimized to target the B2M gene. In some embodiments, at least one of the one to two ribonucleic acids comprises a sequence with a single nucleotide mismatch to a sequence optimized to target the B2M gene. In some embodiments, the target polynucleotide sequences comprises multiple different portions of B2M. In some embodiments, each of the multiple ribonucleic acids comprises a different sequence optimized to target the B2M gene. In some embodiments, each of the multiple ribonucleic acids comprises a sequence with a single nucleotide mismatch to a different sequence optimized to target the B2M gene. In some embodiments, the one to two ribonucleic acids comprise two guide ribonucleic acid sequences.

In some embodiments, the one to two ribonucleic acids comprise two guide ribonucleic acid sequences. In some embodiments, the target polynucleotide sequence comprises CCR5. In some embodiments, the cell comprises a primary CD34+ hematopoietic progenitor cell. In some embodiments, the two guide ribonucleic acid sequences comprise any combination of two guide ribonucleic acid sequences which are complementary to a different sequence selected from the group consisting of SEQ ID NOs: 1-139. In some embodiments, the two guide ribonucleic acid sequences comprise any combination of two guide ribonucleic acid sequences which are complementary to offset sequences selected from the group consisting of SEQ ID NOs: 1-139. In some embodiments, the two guide ribonucleic acid sequences comprise any combination of two guide ribonucleic acid sequences which hybridize to and target Cas protein to offset target sites in CCR5 selected from the group consisting of SEQ ID NOs: 1-139. In some embodiments, the two guide ribonucleic acid sequences comprise any combination of two guide ribonucleic acid sequences from SEQ ID NOs: 298-303. In some embodiments, the two guide ribonucleic acid sequences comprise a pair of guide ribonucleic acids selected from the group consisting of SEQ ID NOs: 299 and 303, SEQ ID NOs: 298 and 300, SEQ ID NOs: 299 and 300, SEQ ID NOs: 298 and 303, SEQ ID NOs: 299 and 301, SEQ ID NOs: 298 and 299, SEQ ID NOs: 301 and 303, SEQ ID NOs: 298 and 302, and SEQ ID NOs: 298 and 301. In some embodiments, the two guide ribonucleic acid sequences comprise any combination of two guide ribonucleic acid sequences which are complementary to a different sequence selected from the group consisting of SEQ ID NOs: 304-333. In some embodiments, the two guide ribonucleic acid sequences comprise any combination of two guide ribonucleic acid sequences which are complementary to offset sequences selected from the group consisting of SEQ ID NOs: 304-333. In some embodiments, the two guide ribonucleic acid sequences comprise any combination of two guide ribonucleic acid sequences which hybridize to and target Cas protein to offset target sites in CCR5 selected from the group consisting of SEQ ID NOs: 304-333. In some embodiments, the target polynucleotide sequence comprises CXCR4. In some embodiments, the cell comprises a primary CD34+ hematopoietic progenitor cell. In some embodiments, the two guide ribonucleic acid sequences comprise any combination of two guide ribonucleic acid sequences which are complementary to a different sequence selected from the group consisting of SEQ ID NOs: 140-297. In some embodiments, the two guide ribonucleic acid sequences comprise any combination of two guide ribonucleic acid sequences which are complementary to offset sequences selected from the group consisting of SEQ ID NOs: 140-297. In some embodiments, the two guide ribonucleic acid sequences comprise any combination of two guide ribonucleic acid sequences which hybridize to and target Cas protein to offset target sites in CXCR4 selected from the group consisting of SEQ ID NOs: 140-297. In some embodiments, the target polynucleotide sequence comprises B2M. In some embodiments, the cell comprises a primary cell. In some embodiments, the two guide ribonucleic acid sequences comprise any combination of two guide ribonucleic acid sequences which are complementary to different sequences in the B2M gene. In some embodiments, the two guide ribonucleic acid sequences comprise any combination of two guide ribonucleic acid sequences which are complementary to offset sequences in the B2M gene. In some embodiments, the two guide ribonucleic acid sequences comprise any combination of two guide ribonucleic acid sequences which hybridize to and target Cas protein to offset target sites in B2M.

In some aspects, the invention provides a method for altering a target polynucleotide sequence in a primary cell comprising contacting the polynucleotide sequence with a clustered regularly interspaced short palindromic repeats-associated (Cas) protein and at least two ribonucleic acids, wherein the at least two ribonucleic acids comprise guide ribonucleic acids which direct Cas protein to and hybridize to a target motif of the target polynucleotide sequence, wherein the target polynucleotide sequence is cleaved. In some embodiments, the efficiency of alteration of cells that express Cas protein is from about 50% to about 80%.

In some aspects, the invention provides a method for altering a target polynucleotide sequence in a primary cell comprising contacting the polynucleotide sequence with a clustered regularly interspaced short palindromic repeats-associated (Cas) protein and at least two ribonucleic acids, wherein the at least two ribonucleic acids comprise guide ribonucleic acids which direct Cas protein to and hybridize to a target motif of the target polynucleotide sequence, wherein the target polynucleotide sequence is cleaved, and wherein the efficiency of alteration of cells that express Cas protein is from about 50% to about 80%.

In some aspects, the invention provides a method for treating or preventing a disorder associated with expression of a polynucleotide sequence in a subject, the method comprising (a) altering a target polynucleotide sequence in a primary cell ex vivo by contacting the polynucleotide sequence with a clustered regularly interspaced short palindromic repeats-associated (Cas) protein and at least two ribonucleic acids, wherein the at least two ribonucleic acids comprise guide ribonucleic acids which direct Cas protein to and hybridize to a target motif of the target polynucleotide sequence, wherein the target polynucleotide sequence is cleaved, and (b) introducing the cell into the subject, thereby treating or preventing a disorder associated with expression of the polynucleotide sequence. In some embodiments, the efficiency of alteration of cells that express Cas protein is from about 50% to about 80%.

In some aspects, the invention provides a method for treating or preventing a disorder associated with expression of a polynucleotide sequence in a subject, the method comprising (a) altering a target polynucleotide sequence in a primary cell ex vivo by contacting the polynucleotide sequence with a clustered regularly interspaced short palindromic repeats-associated (Cas) protein and at least two ribonucleic acids, wherein the at least two ribonucleic acids comprise guide ribonucleic acids which direct Cas protein to and hybridize to a target motif of the target polynucleotide sequence, wherein the target polynucleotide sequence is cleaved, and wherein the efficiency of alteration of cells that express Cas protein is from about 50% to about 80%, and (b) introducing the cell into the subject, thereby treating or preventing a disorder associated with expression of the polynucleotide sequence.

In some aspects, the invention provides, a method for simultaneously altering multiple target polynucleotide sequences in a primary cell comprising contacting the polynucleotide sequences with a clustered regularly interspaced short palindromic repeats-associated (Cas) protein and multiple ribonucleic acids, wherein the ribonucleic acids comprise guide ribonucleic acids which direct Cas protein to and hybridize to target motifs of the target polynucleotide sequences, wherein the target polynucleotide sequences are cleaved. In some embodiments, the efficiency of alteration of cells that express Cas protein is from about 50% to about 80%.

In some aspects, the invention provides a method for simultaneously altering multiple target polynucleotide sequences in a primary cell comprising contacting the polynucleotide sequences with a clustered regularly interspaced short palindromic repeats-associated (Cas) protein and multiple ribonucleic acids, wherein the ribonucleic acids comprise guide ribonucleic acids which direct Cas protein to and hybridize to target motifs of the target polynucleotide sequences, wherein the target polynucleotide sequences are cleaved, and wherein the efficiency of alteration of cells that express Cas protein is from about 50% to about 80%.

In some aspects, the disclosure provides a method for treating or preventing a disorder associated with expression of polynucleotide sequences in a subject, the method comprising (a) altering target polynucleotide sequences in a primary cell ex vivo by contacting the polynucleotide sequences with a clustered regularly interspaced short palindromic repeats-associated (Cas) protein and multiple ribonucleic acids, wherein the ribonucleic acids comprise guide ribonucleic acids which direct Cas protein to and hybridize to target motifs of the target polynucleotide sequences, wherein the target polynucleotide sequences are cleaved, and (b) introducing the cell into the subject, thereby treating or preventing a disorder associated with expression of the polynucleotide sequences. In some embodiments, the efficiency of alteration of cells that express Cas protein is from about 50% to about 80%.

In some aspects, the disclosure provides a method for treating or preventing a disorder associated with expression of polynucleotide sequences in a subject, the method comprising (a) altering target polynucleotide sequences in a primary cell ex vivo by contacting the polynucleotide sequences with a clustered regularly interspaced short palindromic repeats-associated (Cas) protein and multiple ribonucleic acids, wherein the ribonucleic acids comprise guide ribonucleic acids which direct Cas protein to and hybridize to target motifs of the target polynucleotide sequences, wherein the target polynucleotide sequences are cleaved, and wherein the efficiency of alteration of cells that express Cas protein is from about 50% to about 80%, and (b) introducing the cell into the subject, thereby treating or preventing a disorder associated with expression of the polynucleotide sequences.

In some embodiments, the Cas protein is *Streptococcus pyogenes* Cas9 protein or a functional portion thereof. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional domains form a complex. In some embodiments, the Cas protein is Cas9 protein from any bacterial species or functional portion thereof. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional domains form a complex. In some embodiments, the Cas protein is complexed with the one to two ribonucleic acids. In some embodiments, the Cas protein is complexed with the multiple ribonucleic acids.

In some embodiments, the target motif is a 20-nucleotide DNA sequence. In some embodiments, each target motif is a 20-nucleotide DNA sequence. In some embodiments, the target motif is a 20-nucleotide DNA sequence beginning with G and immediately precedes an NGG motif recognized by the Cas protein. In some embodiments, each target motif is a 20-nucleotide DNA sequence beginning with G and immediately precedes an NGG motif recognized by the Cas protein. In some embodiments, the target motif is a 20-nucleotide DNA sequence and immediately precedes an NGG motif recognized by the Cas protein. In some) embodiments, each target motif is a 20-nucleotide DNA sequence and immediately precedes an NGG motif recognized by the Cas protein. In some embodiments, the target motif is $G(N)_{19}NGG$. In some embodiments, each target motif is $G(N)_{19}NGG$. In some embodiments, the target motif is $(N)_{20}NGG$. In some embodiments, each target motif is $(N)_{20}NGG$. In some embodiments, the target motif comprises a sequence selected from the group consisting of SEQ ID NOs: 1-297 or 304-333. In some embodiments, the target motif comprises a sequence selected from the group consisting of SEQ ID NOs: 1-297 or 304-333. In some embodiments, the target polynucleotide sequence is cleaved such that a double-strand break results. In some embodiments, each target polynucleotide sequence is cleaved such that a double-strand break results. In some embodiments, the target polynucleotide sequence is cleaved such that a single-strand break results. In some embodiments, each target polynucleotide sequence is cleaved such that a single-strand break results. In some embodiments, the alteration is an indel. In some embodiments, the alteration results in reduced expression of the target polynucleotide sequence. In some embodiments, the alteration results in reduced expression of the target polynucleotide sequences. In some embodiments, the alteration results in a knock out of the target polynucleotide sequence. In some embodiments, the alteration results in a knock out of the target polynucleotide sequences. In some embodiments, the alteration results in correction of the target polynucleotide sequence from an undesired sequence to a desired sequence. In some embodiments, the alteration results in correction of the target polynucleotide sequences from undesired sequences to desired sequences. In some embodiments, the alteration is a homozygous alteration.

In some embodiments, each alteration is a homozygous alteration. In some embodiments, subsequent to cleavage of the target polynucleotide sequence, homology-directed repair occurs. In some embodiments, homology-directed repair is performed using an exogenously introduced DNA repair template. In some embodiments, the exogenously introduced DNA repair template is single-stranded. In some embodiments, the exogenously introduced DNA repair template is double-stranded. In some embodiments, subsequent to cleavage of the target polynucleotide sequences, homology-directed repair occurs. In some embodiments, homology-directed repair is performed using an exogenously introduced DNA repair template. In some embodiments, the exogenously introduced DNA repair template is single-stranded. In some embodiments, the exogenously introduced DNA repair template is double-stranded. In some embodiments, the cell is a peripheral blood cell. In some embodiments, the cell is a stem cell or a pluripotent cell. In some embodiments, the cell is a hematopoietic stem cell. In some embodiments, the cell is a $CD34^+$ cell. In some embodiments, the cell is a $CD34^+$ mobilized peripheral blood cell. In some embodiments, the cell is a $CD34^+$ cord blood cell. In some embodiments, the cell is a $CD34^+$ bone marrow cell. In some embodiments, the cell is a $CD34^+CD38$-Lineage-$CD90^+CD45RA^-$ cell. In some embodiments, the cell is a hepatocyte. In some embodiments, the cell is a primary cell. In some embodiments, the target polynucleotide sequence is CCR5.

In some embodiments, the two ribonucleic acids comprise a different sequence selected from the group consisting of SEQ ID NOs: 298-303. In some embodiments, the two guide ribonucleic acid sequences comprise a pair of guide ribonucleic acids selected from the group consisting of SEQ ID NOs: 299 and 303, SEQ ID NOs: 298 and 300, SEQ ID NOs: 299 and 300, SEQ ID NOs: 298 and 303, SEQ ID NOs: 299 and 301, SEQ ID NOs: 298 and 299, SEQ ID NOs: 301 and 303, SEQ ID NOs: 298 and 302, and SEQ ID NOs: 298 and 301. In some embodiments, the two ribonucleic acids comprise sequences which are complementary to and/or hybridize to different sequences selected from the group consisting of SEQ ID NOs: 1-139 and 304-333. In some embodiments, the two ribonucleic acids comprise sequences which are complementary to and/or hybridize to different sequences with a single nucleotide mismatch to a sequence selected from the group consisting of SEQ ID NOs: 1-139 and 304-333. In some embodiments, the two ribonucleic acids comprise sequences which are complementary to and/or hybridizes to offset sequences selected from the group consisting of SEQ ID NOs: 1-139 and 304-333. In some embodiments, the two ribonucleic acids comprise sequences which are complementary to and/or hybridize to offsets sequences with a single nucleotide mismatch to a sequence selected from the group consisting of SEQ ID NOs: 1-139 and 304-333. In some embodiments, the target polynucleotide sequence is CXCR4. In some embodiments, the two ribonucleic acids comprise sequences which are complementary to and/or hybridize to different sequences selected from the group consisting of SEQ ID NO: 140-297. In some embodiments, the two ribonucleic acids comprise sequences which are complementary to and/or hybridize to different sequences with a single nucleotide mismatch to a sequence selected from the group consisting of SEQ ID NO: 140-297. In some embodiments, the two ribonucleic acids comprise sequences which are complementary to and/or hybridize to offset sequences selected from the group consisting of SEQ ID NO: 140-297. In some embodiments, the two ribonucleic acids comprise sequences which are complementary to and/or hybridize to offset sequences with a single nucleotide mismatch to a sequence selected from the group consisting of SEQ ID NO: 140-297. In some embodiments, the target polynucleotide sequences comprise multiple different portions of CCR5. In some embodiments, each of the multiple ribonucleic acids comprises a sequence which is complementary to and/or hybridizes to a different sequence selected from the group consisting of SEQ ID NOs: 1-139 and 304-333. In some embodiments, each of the multiple ribonucleic acids comprises a sequence which is complementary to and/or hybridizes to an offset sequence selected from the group consisting of SEQ ID NOs: 1-139 and 304-333. In some embodiments, each of the multiple ribonucleic acids comprises a sequence which is complementary to and/or hybridizes to a sequence with a single nucleotide mismatch to a different sequence selected from the group consisting of SEQ ID NOs: 1-139 and 304-333. In some embodiments, each of the multiple ribonucleic acids comprises a sequence which is complementary to and/or hybridizes to a sequence with a single nucleotide mismatch to an offset sequence selected from the group consisting of SEQ ID NOs: 1-139 and 304-333.

In some embodiments, the target polynucleotide sequences comprise multiple different portions of CXCR4. In some embodiments, each of the multiple ribonucleic acids comprises a sequence which is complementary to and/or hybridizes to a different sequence selected from the group consisting of SEQ ID NOs: 140-297 and 304-333. In some embodiments, each of the multiple ribonucleic acids comprises a sequence which is complementary to and/or hybridizes to an offset sequence selected from the group consisting of SEQ ID NOs: 140-297 and 304-333. In some embodiments, each of the multiple ribonucleic acids comprises a sequence which is complementary to and/or hybridizes to a sequence with a single nucleotide mismatch to a different sequence selected from the group consisting of SEQ ID NOs: 140-297 and 304-333. In some embodiments, each of the multiple ribonucleic acids comprises a sequence which is complementary to and/or hybridizes to a sequence with a single nucleotide mismatch to an offset sequence selected from the group consisting of SEQ ID NOs: 140-297 and 304-333.

In some embodiments, the target polynucleotide sequences comprise at least a portion of CCR5 and at least a portion of CXCR4. In some embodiments, each of the multiple ribonucleic acids comprises a sequence which is complementary to and/or hybridizes to a different sequence selected from the group consisting of SEQ ID NOs: 1-297 and 304-333. In some embodiments, each of the multiple ribonucleic acids comprises a sequence which is complementary to and/or hybridizes to an offset sequence selected from the group consisting of SEQ ID NOs: 1-297 and 304-333. In some embodiments, each of the multiple ribonucleic acids comprises a sequence which is complementary to and/or hybridizes to a sequence with a single nucleotide mismatch to a different sequence selected from the group consisting of SEQ ID NOs: 1-297 and 304-333. In some embodiments, each of the multiple ribonucleic acids comprises a sequence which is complementary to and/or hybridizes to a sequence with a single nucleotide mismatch to an offset sequence selected from the group consisting of SEQ ID NOs: 1-297 and 304-333. In some embodiments, the multiple ribonucleic acids comprise at least two ribonucleic acid sequences which are complementary to and/or hybridize to offset sequences selected from the group consisting of SEQ ID NOs: 1-139 and 304-333, and at least two ribonucleic acid sequences which are complementary to and/or hybridize to offset sequences selected from the group consisting of SEQ ID NOs: 140-297. In some embodiments, the multiple ribonucleic acids comprises at least two ribonucleic acid sequences which are complementary to and/or hybridize to different sequences with a single nucleotide mismatch to an offset sequence selected from the group consisting of SEQ ID NOs: 1-139 and 304-333, and at least two ribonucleic acid sequences which are complementary to and/or hybridize to different sequences with a single nucleotide mismatch to an offset sequence selected from the group consisting of SEQ ID NOs: 140-297.

In some embodiments, the disorder is a genetic disorder. In some embodiments, the disorder is a monogenic disorder. In some embodiments, the disorder is human immunodeficiency virus (HIV) infection. In some embodiments, the disorder is acquired immunodeficiency syndrome (AIDS). In some embodiments, the two ribonucleic acids are designed to hybridize to a target motif immediately adjacent to a deoxyribonucleic acid motif recognized by the Cas protein. In some embodiments, each of the two ribonucleic acids are designed to hybridize to target motifs immediately adjacent to deoxyribonucleic acid motifs recognized by the Cas protein which flank a mutant allele located between the target motifs. In some embodiments, the multiple ribonucleic acids are designed to hybridize to target motifs immediately adjacent to deoxyribonucleic acid motifs recognized by the Cas protein. In some embodiments, the multiple ribonucleic acids are designed to hybridize to target motifs immediately adjacent to deoxyribonucleic acid motifs recognized by the Cas protein which flank mutant alleles located between the target motifs. In some embodiments, the two ribonucleic acids are selected to minimize hybridization with nucleic acid sequences other than the target polynucleotide sequence. In some embodiments, the multiple ribonucleic acids are selected to minimize hybridization with nucleic acid sequences other than the target polynucleotide sequence. In some embodiments, the target motif is selected such that it contains at least two mismatches when compared with all other genomic nucleotide sequences in the cell. In some embodiments, each target motif is selected such that it contains at least two mismatches when compared with all other genomic nucleotide sequences in the cell. In some embodiments, the target motif is selected such that it contains at least one mismatch when compared with all other genomic nucleotide sequences in the cell. In some embodiments, the target motif is selected such that it contains at least one mismatch when compared with all other genomic nucleotide sequences in the cell. In some embodiments, the two ribonucleic acids hybridize to a target motif that contains at least two mismatches when compared with all other genomic nucleotide sequences in the cell. In some embodiments, each of the multiple ribonucleic acids hybridize to target motifs that contain at least two mismatches when compared with all other genomic nucleotide sequences in the cell.

In some embodiments, the two ribonucleic acids hybridize to a target motif that contains at least one mismatch when compared with all other genomic nucleotide sequences in the cell. In some embodiments, each of the multiple ribonucleic acids hybridize to, target motifs that contain at least one mismatch when compared with all other genomic nucleotide sequences in the cell. In some embodiments, the efficiency of alteration at each loci is from about 50% to about 80%.

In some embodiments, the Cas protein is encoded by a modified nucleic acid. In some embodiments, the modified nucleic acid comprises a ribonucleic acid containing at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. In some embodiments, at least one of the two ribonucleic acids is a modified ribonucleic acid comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. In some embodiments, the two ribonucleic acids comprise modified ribonucleic acids comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

In some embodiments, any of the Cas protein or the ribonucleic acids are expressed from a plasmid. In some embodiments, any of the Cas protein or the ribonucleic acids are expressed using a promoter optimized for increased expression in stem cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter. In some embodiments, the method comprises selecting cells that express the Cas protein. In some embodiments, selecting cells comprises FACS. In some embodiments, FACs is used to select cells which co-express Cas and a fluorescent protein.

In some aspects, the invention provides a method for altering a target polynucleotide sequence in a cell comprising contacting the polynucleotide sequence in a cell selected from the group consisting of a human pluripotent cell, a primary human cell, and a non-transformed human cell, with a clustered regularly interspaced short palindromic repeats-associated (Cas) protein and two ribonucleic acids, wherein the ribonucleic acids direct Cas protein to and hybridize to a target motif of the target polynucleotide sequence, wherein the target polynucleotide sequence is cleaved. In some embodiments, the efficiency of alteration of cells that express Cas protein is from about 8% to about 80%.

In some aspects, the invention provides a method for altering a target polynucleotide sequence in a cell comprising contacting the polynucleotide sequence in a cell selected from the group consisting of a human pluripotent cell, a primary human cell, and a non-transformed human cell, with a clustered regularly interspaced short palindromic repeats-associated (Cas) protein and two ribonucleic acids, wherein the ribonucleic acids direct Cas protein to and hybridize to a target motif of the target polynucleotide sequence, wherein the target polynucleotide sequence is cleaved, and wherein the efficiency of alteration of cells that express Cas protein is from about 8% to about 80%.

In some aspects, the invention provides a method for treating or preventing a disorder associated with expression of a polynucleotide sequence in a subject, the method comprising (a) altering a target polynucleotide sequence in a cell ex vivo by contacting the polynucleotide sequence in a cell selected from the group consisting of a human pluripotent cell, a primary human cell, and a non-transformed human cell, with a clustered regularly interspaced short palindromic repeats-associated (Cas) protein and two ribonucleic acids, wherein the ribonucleic acids direct Cas protein to and hybridize to a target motif of the target polynucleotide sequence, wherein the target polynucleotide sequence is cleaved, and (b) introducing the cell into the subject, thereby treating or preventing a disorder associated with expression of the polynucleotide sequence. In some embodiments, the efficiency of alteration is from about 8% to about 80%.

In some aspects, the invention provides a method for treating or preventing a disorder associated with expression of a polynucleotide sequence in a subject, the method comprising (a) altering a target polynucleotide sequence in a cell ex vivo by contacting the polynucleotide sequence in a cell selected from the group consisting of a human pluripotent cell, a primary human cell, and a non-transformed human cell, with a clustered regularly interspaced short palindromic repeats-associated (Cas) protein and two ribonucleic acids, wherein the ribonucleic acids direct Cas protein to and hybridize to a target motif of the target polynucleotide sequence, wherein the target polynucleotide sequence is cleaved, and wherein the efficiency of alteration is from about 8% to about 80%, and (b) introducing the cell into the subject, thereby treating or preventing a disorder associated with expression of the polynucleotide sequence.

In some aspects, the invention provides a method for simultaneously altering multiple target polynucleotide sequences in a cell comprising contacting the polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved. In some embodiments, the efficiency of alteration of cells that express Cas protein is from about 8% to about 80%.

In some aspects, the invention provides a method for simultaneously altering multiple target polynucleotide sequences in a cell comprising contacting the polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 8% to about 80%.

In some aspects, the invention provides a method for treating or preventing a disorder associated with expression of polynucleotide sequences in a subject, the method comprising (a) altering target polynucleotide sequences in a cell ex vivo by contacting the polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and (b) introducing the cell into the subject, thereby treating or preventing a disorder associated with expression of the polynucleotide sequences. In some embodiments, the efficiency of alteration of cells that express Cas protein is from about 8% to about 80%.

In some aspects, the invention provides a method for treating or preventing a disorder associated with expression of polynucleotide sequences in a subject, the method comprising (a) altering target polynucleotide sequences in a cell ex vivo by contacting the polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 8% to about 80%, and (b) introducing the cell into the subject, thereby treating or preventing a disorder associated with expression of the polynucleotide sequences.

In some aspects, the disclosure provides a composition comprising at least two ribonucleic acids each comprising a different sequence selected from the group consisting of SEQ ID NOs: 298-303.

In some aspects, the disclosure provides a composition comprising at least two ribonucleic acids each comprising a sequence which is complementary to and/or hybridizes to a different sequence selected from the group consisting of SEQ ID NOs: 1-139 and 304-333.

In some aspects, the disclosure provides a composition comprising at least two ribonucleic acids each comprising a sequence which is complementary to and/or hybridizes to a sequence with a single nucleotide mismatch to a sequence selected from the group consisting of SEQ ID NOs: 1-139 and 304-333.

In some aspects, the disclosure provides a composition comprising at least two ribonucleic acids each comprising a sequence which is complementary to and/or hybridizes to a different sequence selected from the group consisting of SEQ ID NOs: 140-297.

In some aspects, the disclosure provides a composition comprising at least two ribonucleic acids each comprising a sequence which is complementary to and/or hybridizes to a sequence with a single nucleotide mismatch to a sequence selected from the group consisting of SEQ ID NOs: 140-297.

In some embodiments, at least one of the two ribonucleic acids is a modified ribonucleic acid comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

In some embodiments, the two ribonucleic acids comprise modified ribonucleic acids comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. In some embodiments, the composition includes a nucleic acid sequence encoding a Cas protein. In some embodiments, the composition includes a nucleic acid sequence encoding a Cas9 protein or a functional portion thereof. In some embodiments, the nucleic acid comprises a modified ribonucleic acid comprising at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

In some aspects, the invention provides a composition comprising a chimeric nucleic acid comprising a ribonucleic acid encoding a Cas protein and at least two additional ribonucleic acids each having a sequence selected from the group consisting of the ribonucleic acid sequences of SEQ ID NOs: 298-303.

In some aspects, the invention provides a chimeric nucleic acid comprising a ribonucleic acid encoding a Cas protein and at least two additional ribonucleic acids each having a sequence which is complementary to and/or hybridizes to a different sequence selected from the group consisting of SEQ ID NOs: 1-139 and 304-333.

In some aspects, the invention provides a composition comprising a chimeric nucleic acid comprising a ribonucleic acid encoding a Cas protein and at least two additional ribonucleic acids each having a sequence which is complementary to and/or hybridizes to a different sequence selected from the group consisting of SEQ ID NOs: 140-297.

In some aspects, the invention provides a composition comprising a chimeric nucleic acid comprising a ribonucleic acid encoding a Cas protein and at least two additional ribonucleic acid sequences each comprising a sequence which is complementary to and/or hybridizes to a sequence with a single nucleotide mismatch to a sequence selected from the group consisting of SEQ ID NOs: 1-139 and 304-333.

In some aspects, the invention provides a composition comprising a chimeric nucleic acid comprising a ribonucleic acid encoding a Cas protein and at least two additional ribonucleic acid sequences each comprising a sequence which is complementary to and/or hybridizes to a sequence with a single nucleotide mismatch to a sequence selected from the group consisting of SEQ ID NOs: 140-297.

In some embodiments, the composition includes a nucleic acid sequence encoding a detectable marker. In some embodiments, the composition includes a nucleic acid sequence encoding a fluorescent protein. In some embodiments, the composition includes a promoter operably linked to the chimeric nucleic acid. In some embodiments, the promoter is optimized for increased expression in human stem cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter. In some embodiments, the chimeric nucleic acid comprises at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate. In some embodiments, the Cas protein comprises a Cas9 protein or a functional portion thereof.

In some aspects, the invention provides a kit for altering a target polynucleotide sequence in a cell comprising a Cas9 protein or a nucleic acid encoding the Cas9 protein, and at least two ribonucleic acids each comprising a different sequence selected from the group consisting of the ribonucleic acid sequences of SEQ ID NOs: 298-303.

In some aspects, the invention provides a kit for altering a target polynucleotide sequence in a cell comprising a Cas9 protein or a nucleic acid encoding the Cas9 protein, and at least two ribonucleic acids each comprising a sequence which is complementary to and/or hybridizes to a different sequence selected from the group consisting of SEQ ID NOs: 1-139 and 304-333.

In some aspects, the invention provides a kit for altering a target polynucleotide sequence in a cell comprising a Cas9 protein or a nucleic acid encoding the Cas9 protein, and at least two ribonucleic acids each comprising a sequence which is complementary to and/or hybridizes to a different sequence selected from the group consisting of SEQ ID NOs: 140-297.

In some embodiments, the kit includes one or more cell lines, cultures, or populations selected from the group consisting of human pluripotent cells, primary human cells, and non-transformed cells. In some aspects, the kit includes a DNA repair template.

In some aspects, the invention provides a method of administering cells to a subject in need of such cells, the method comprising: (a) contacting a cell or population of cells ex vivo with a Cas protein and two ribonucleic acids which direct Cas protein to and hybridize to a target polynucleotide sequence encoding B2M in the cell or population of cells, wherein the target polynucleotide sequence is cleaved; and (b) administering the resulting cells from (a) to a subject in need of such cells.

In some aspects, the invention provides a method of administering cells to a subject in need of such cells, the method comprising: (a) contacting a cell or population of cells ex vivo with (i) a Cas protein, (ii) at least two ribonucleic acids which direct Cas protein to and hybridize to a target polynucleotide sequence encoding B2M in the cell or population of cells, and (iii) at least two additional ribonucleic acids which direct Cas protein to and hybridize to a target polynucleotide sequence in the cell or population of cells, wherein the target polynucleotide sequences are cleaved; and (b) administering the resulting cell or cells from (a) to a subject in need of such cells.

In some embodiments, cleavage of the target polynucleotide sequence encoding B2M in the cell or population of cells reduces the likelihood that the resulting cell or cells will trigger a host immune response when the cells are administered to the subject. In some aspects, the target polynucleotide sequence comprises CCR5. In some embodiments, the at least two ribonucleic acids comprise two different sequences selected from the group consisting of SEQ ID NOs: 298-303. In some embodiments, the at least two ribonucleic acids each comprise sequences which are complementary to and/or hybridize to a different sequence selected from the group consisting of SEQ ID NOs: 1-139 and 304-333. In some embodiments, the at least two ribonucleic acids each comprise sequences which are complementary to and/or hybridize to sequences comprising at least one nucleotide mismatch to different sequences selected from the group consisting of SEQ ID NOs: 1-139 and 304-333. In some embodiments, the target polynucleotide sequence comprises CXCR4. In some embodiments, the at least two ribonucleic acids each comprise sequences which are complementary to and/or hybridize to a different sequence selected from the group consisting of SEQ ID NOs: 140-297. In some embodiments, the at least two ribonucleic acids each comprise sequences which are complementary to and/or hybridize to sequences comprising at least one nucleotide mismatch to different sequences selected from the group consisting of SEQ ID NOs: 140-297. In some embodiments, the cell or population of cells comprises primary cells. In some embodiments, the subject in need of administration of cells is suffering from a disorder. In some embodiments, the disorder comprises a genetic disorder. In some embodiments, the disorder comprises an infection. In some embodiments, the disorder comprises HIV or AIDS. In some embodiments, the disorder comprises cancer.

In some aspects, the invention provides a method of reducing the likelihood that cells administered to a subject will trigger a host immune response in the subject, the method comprising: (a) contacting a cell or population of cells ex vivo with a Cas protein and two ribonucleic acids which direct Cas protein to and hybridize to a target polynucleotide sequence encoding B2M in the cell or population of cells, wherein the target polynucleotide sequence encoding B2M is cleaved, thereby reducing the likelihood that cells administered to the subject will trigger a host immune response in the subject; and (b) administering the resulting cells from (a) to a subject in need of such cells.

In some aspects, the invention provides a method of reducing the likelihood that cells administered to a subject will trigger a host immune response in the subject, the method comprising: (a) contacting a cell or population of cells ex vivo with (i) a Cas protein, (ii) at least two ribonucleic acids which direct Cas protein to and hybridize to a target polynucleotide sequence encoding B2M in the cell or population of cells, wherein the target polynucleotide sequence encoding B2M in the cell or population of cells is cleaved, thereby reducing the likelihood that the cell or population of cells will trigger a host immune response in the subject, and (iii) at least two additional ribonucleic acids which direct Cas protein to and hybridize to a target polynucleotide sequence in the cell or population of cells, wherein the target polynucleotide sequence is cleaved; and (b) administering the resulting cell or cells from (a) to a subject in need of such cells.

In some embodiments, the target polynucleotide sequence comprises CCR5. In some embodiments, the at least two ribonucleic acids comprise two different sequences selected from the group consisting of SEQ ID NOs: 298-303. In some embodiments, the at least two ribonucleic acids each comprise sequences which are complementary to and/or hybridize to a different sequence selected from the group consisting of SEQ ID NOs: 1-139 and 304-333. In some embodiments, the at least two ribonucleic acids each comprise sequences which are complementary to and/or hybridize to sequences comprising at least one nucleotide mismatch to different sequences selected from the group consisting of SEQ ID NOs: 1-139 and 304-333. In some embodiments, the target polynucleotide sequence comprises CXCR4. In some embodiments, the at least two ribonucleic acids each comprise sequences which are complementary to and/or hybridize to a different sequence selected from the group consisting of SEQ ID NOs: 140-297. In some embodiments, the at least two ribonucleic acids each comprise sequences which are complementary to and/or hybridize to sequences comprising at least one nucleotide mismatch to different sequences selected from the group consisting of SEQ ID NOs: 140-297. In some embodiments, the cell or population of cells comprises primary cells. In some embodiments, the subject in need of administration of cells is suffering from a disorder. In some embodiments, the disorder comprises a genetic disorder. In some embodiments, the disorder comprises an infection. In some embodiments, the disorder comprises HIV or AIDs. In some embodiments, the disorder comprises cancer.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 shows exemplary guide RNA sequences useful when the target polynucleotide sequence is human CCR5.

FIG. 2 shows exemplary guide RNA sequences useful when the target polynucleotide sequence is human CXCR4.

FIG. 3 shows an exemplary amino acid sequence of a Cas protein. Yellow highlights indicate Ruv-C-like domain. Underlining indicates HNH nuclease domain.

FIGS. 4A, 4B, 4C, 4D and 4E demonstrate that a single guide strategy achieves high efficiency genome editing in cell lines, but not in clinically relevant primary somatic cells. FIG. 4A is a table showing CRISPR-targeting sites in the CCR5 locus (single guides), which were found by scanning the human chemokine receptor CCR5 gene for optimized guide RNA sequences using a CRISPR design program (available on the world wide web at http://CRISPR.mit.edu) (left panel). A total of 11 guide RNAs having a score greater than 50 was tested for editing efficiency in a K562 cell line. FIG. 4A (right panel) shows the editing efficiency of 7 of selected guides (% indels) was measured by a CEL surveyor assay. FIG. 4B shows a comparative analysis of genome-editing efficiency in cell lines 293T, K562 (left two panels) and primary human CD34+ HSPCs (right two panels) illustrating inefficient genome editing efficiency in primary CD34+ cells. Cells were transfected with Cas9 (lane 1) together with guide RNA (lane 2) or expression plasmids (lane 3). FIG. 4C is a schematic illustrating CRISPR-targeting sites in the CCR5 locus (single guides). FIG. 4D shows the results of targeting the B2M locus with single guide RNAs in 293T cells. FIG. 4E shows the results of flow cytometry analysis using a single guide strategy targeting B2M in 293T cell, which demonstrate that B2M CRISPRs ablate B2M surface expression with high efficiency.

FIG. 5A shows that as compared to single guide (A or B), 2-guide combination (A+B) showed robust editing efficiency in targeting CCR5 in K562 cell line. FIG. 5B shows various guide combinations and spacing between each guide pair with orientation (upper panel). The PCR results (bottom left panel) and CEL assay (bottom right) show robust genome editing for tested guide pairs. FIG. 5C shows the results of PCR analysis indicating that with 2-guide combination wild-type Cas9 effectively deleted the DNA sequence between the two guides, in contrast to Nickase (D10A) which did not effectively delete the DNA sequence between the two guides.

FIG. 6A is a representative gel picture showing efficient clonal deletion frequency using two guides. Clonal deletion efficiency was determined by PCR carried on individual colony grown on methyl cellulose. FIG. 6B is a Table showing data obtained from two independent clonal deletion experiments, which suggests efficacious genome-editing in primary human CD34+ cells using a two-guide approach.

FIG. 7A shows the gating strategy for flow cytometry analysis of 293T cells electroporated with 1 μg Cas9 plus either 0.5 μg gRNA or 0.25 μg+0.25 μg gRNA targeting B2M 72 hours post-transfection in a 6-well format. FIG. 7B shows the results of a SURVEYOR assay with B2M CRISPR gRNAs in 293T cells (72 h). FIG. 7C shows that the double guide strategy does not improve B2M cutting efficiency in 293T cells, in contrast to the double guide strategy which significantly improves B2M cutting efficiency in primary cells (FIG. 5).

FIG. 8A shows the results of a flow cytometry analysis demonstrating B2M knock-out efficiency in CD4+ T cells (total live cells). FIG. 8B shows the results of a flow cytometry analysis demonstrating B2M knock-out efficiency in CD4+ T cells (gated on GFP+ cells). FIG. 8C shows a Table quantifying the results of a flow cytometry analysis demonstrating B2M knock-out efficiency in CD4+ T cells. FIG. 8D shows the results of a flow cytometry analysis of cells gated on live/7AAD neg/ GFP+ cells, demonstrating that the double guide strategy results in ablation of B2M surface expression.

DETAILED DESCRIPTION OF THE INVENTION

Figure 4B:
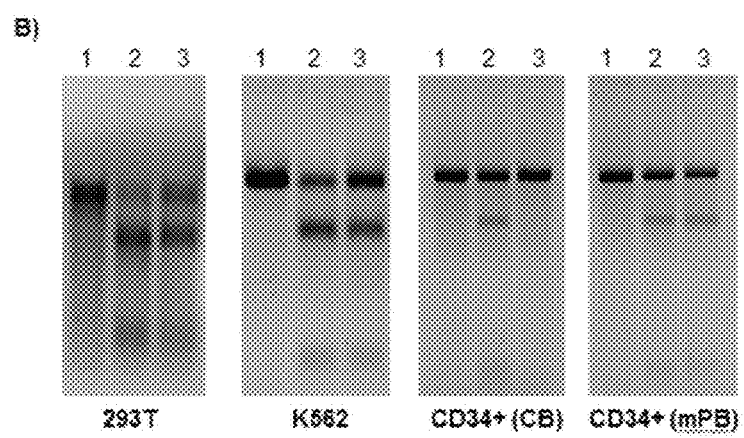

Work described herein demonstrates methods of allele targeting using CRISPR/Cas systems resulting in mutant cells with efficiencies of up to 80%. In particular, work described herein surprisingly and unexpectedly demonstrates that a multiple guide strategy (e.g., using two or more ribonucleic acids which guide Cas protein to and hybridize to a target polynucleotide sequence) efficiently and effectively deletes target polynucleotide sequences (e.g., B2M, HPRT, CCR5 and/or CXCR4) in primary somatic cells (e.g., human blood cells, e.g., CD34+ and T cells), in contrast to a single guide strategy which has been demonstrated by the inventors to efficiently delete target polynucleotide sequences in cell lines (e.g., 293T) but not in primary somatic cells. These vastly improved methods permit CRISPR/Cas systems to be utilized effectively for the first time for therapeutic purposes. Methods of delivery of CRISPR/Cas systems to human stem cells are provided. In addition, methods of specifically identifying useful RNA guide sequences are provided, along with particular guide sequences useful in targeting specific genes (e.g., B2M, HPRT, CCR5 and/or CXCR4). Moreover, methods of treatment (e.g., methods of treating HIV infection) utilizing the compositions and methods disclosed herein are provided. Moreover, methods of administering cells (e.g., methods of administering a cell that has a reduced likelihood of triggering a host immune response) utilizing the compositions and methods disclosed herein are provided.

In one aspect, the present invention provides a method for altering a target polynucleotide sequence in a cell.

An exemplary method for altering a target polynucleotide sequence in a cell comprises contacting the polynucleotide sequence with a clustered regularly interspaced short palindromic repeats-associated (Cas) protein and from one to two ribonucleic acids, wherein the ribonucleic acids direct Cas protein to and hybridize to a target motif of the target polynucleotide sequence, wherein the target polynucleotide sequence is cleaved, and wherein the efficiency of alteration of cells that express Cas protein is from about 50% to about 80%.

As used herein, the term "contacting" (i.e., contacting a polynucleotide sequence with a clustered regularly interspaced short palindromic repeats-associated (Cas) protein and/or ribonucleic acids) is intended to include incubating the Cas protein and/or the ribonucleic acids in the cell together in vitro (e.g., adding the Cas protein or nucleic acid encoding the Cas protein to cells in culture) or contacting a cell ex vivo. The step of contacting a target polynucleotide sequence with a Cas protein and/or ribonucleic acids as disclosed herein can be conducted in any suitable manner. For example, the cells may be treated in adherent culture, or in suspension culture. It is understood that the cells contacted with a Cas protein and/or ribonucleic acids as disclosed herein can also be simultaneously or subsequently contacted with another agent, such as a growth factor or other differentiation agent or environments to stabilize the cells, or to differentiate the cells further.

In another aspect, the present invention provides a method for treating or preventing a disorder associated with expression of a polynucleotide sequence in a subject.

The terms "treat", "treating", "treatment", etc., as applied to an isolated cell, include subjecting the cell to any kind of process or condition or performing any kind of manipulation or procedure on the cell. As applied to a subject, the terms refer to providing a cell in which a target polynucleotide sequence has been altered ex vivo according to the methods described herein to an individual. The individual is usually ill or injured, or at increased risk of becoming ill relative to an average member of the population and in need of such attention, care, or management.

As used herein, the term "treating" and "treatment" refers to administering to a subject an effective amount of cells with target polynucleotide sequences altered ex vivo according to the methods described herein so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a disorder associated with expression of a polynucleotide sequence, as well as those likely to develop such a disorder due to genetic susceptibility or other factors.

By "treatment," "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

An exemplary method for treating or preventing a disorder associated with expression of a polynucleotide sequence in a subject comprises (a) altering a target polynucleotide sequence in a cell ex vivo by contacting the polynucleotide sequence with a clustered regularly interspaced short palindromic repeats-associated (Cas) protein and from one to two ribonucleic acids, wherein the ribonucleic acids direct Cas protein to and hybridize to a target motif of the target polynucleotide sequence, wherein the target polynucleotide sequence is cleaved, and wherein the efficiency of alteration of cells that express Cas protein is from about 50% to about 80%, and (b) introducing the cell into the subject, thereby treating or preventing a disorder associated with expression of the polynucleotide sequence.

The present invention contemplates altering target polynucleotide sequences in any manner which is available to the skilled artisan utilizing a CRISPR/Cas system of the present invention. Any CRISPR/Cas system that is capable of altering a target polynucleotide sequence in a cell can be used. Such CRISPR-Cas systems can employ a variety of Cas proteins (Haft et al. *PLoS Comput Biol.* 2005; 1(6)e60). The molecular machinery of such Cas proteins that allows the CRISPR/Cas system to alter target polynucleotide sequences in cells include RNA binding proteins, endo- and exo-nucleases, helicases, and polymerases. In some embodiments, the CRISPR/Cas system is a CRISPR type I system. In some embodiments, the CRISPR/Cas system is a CRISPR type II system.

The CRISPR/Cas systems of the present invention can be used to alter a target polynucleotide sequence in a cell. The present invention contemplates altering target polynucleotide sequences in a cell for any purpose. In some embodiments, the target polynucleotide sequence in a cell is altered to produce a mutant cell. As used herein, a "mutant cell" refers to a cell with a resulting genotype that differs from its original genotype. In some instances, a "mutant cell" exhibits a mutant phenotype, for example when a normally functioning gene is altered using the CRISPR/Cas systems of the present invention. In other instances, a "mutant cell" exhibits a wild-type phenotype, for example when a CRISPR/Cas system of the present invention is used to correct a mutant genotype. In some embodiments, the target polynucleotide sequence in a cell is altered to correct or repair a genetic mutation (e.g., to restore a normal phenotype to the cell). In some embodiments, the target polynucleotide sequence in a cell is altered to induce a genetic mutation (e.g., to disrupt the function of a gene or genomic element).

In some embodiments, the alteration is an indel. As used herein, "indel" refers to a mutation resulting from an insertion, deletion, or a combination thereof. As will be appreciated by those skilled in the art, an indel in a coding region of a genomic sequence will result in a frameshift mutation, unless the length of the indel is a multiple of three. In some embodiments, the alteration is a point mutation. As used herein, "point mutation" refers to a substitution that replaces one of the nucleotides. A CRISPR/Cas system of the present invention can be used to induce an indel of any length or a point mutation in a target polynucleotide sequence.

In some embodiments, the alteration results in a knock out of the target polynucleotide sequence or a portion thereof. Knocking out a target polynucleotide sequence or a portion thereof using a CRISPR/Cas system of the present invention can be useful for a variety of applications. For example, knocking out a target polynucleotide sequence in a cell can be performed in vitro for research purposes. For ex vivo purposes, knocking out a target polynucleotide sequence in a cell can be useful for treating or preventing a disorder associated with expression of the target polynucleotide sequence (e.g., by knocking out a mutant allele in a cell ex vivo and introducing those cells comprising the knocked out mutant allele into a subject).

As used herein, "knock out" includes deleting all or a portion of the target polynucleotide sequence in a way that interferes with the function of the target polynucleotide sequence. For example, a knock out can be achieved by altering a target polynucleotide sequence by inducing an indel in the target polynucleotide sequence in a functional domain of the target polynucleotide sequence (e.g., a DNA binding domain). Those skilled in the art will readily appreciate how to use the CRISPR/Cas systems of the present invention to knock out a target polynucleotide sequence or a portion thereof based upon the details described herein.

In some embodiments, the alteration results in reduced expression of the target polynucleotide sequence. The terms "decrease," "reduced," "reduction," and "decrease" are all used herein generally to mean a decrease by a statistically significant amount. However, for avoidance of doubt, decrease," "reduced," "reduction," "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

In some embodiments, the alteration is a homozygous alteration. In some embodiments, the alteration is a heterozygous alteration.

In some embodiments, the alteration results in correction of the target polynucleotide sequence from an undesired sequence to a desired sequence. The CRISPR/Cas systems of the present invention can be used to correct any type of mutation or error in a target polynucleotide sequence. For example, the CRISPR/Cas systems of the present invention can be used to insert a nucleotide sequence that is missing from a target polynucleotide sequence due to a deletion. The CRISPR/Cas systems of the present invention can also be used to delete or excise a nucleotide sequence from a target polynucleotide sequence due to an insertion mutation. In some instances, the CRISPR/Cas systems of the present invention can be used to replace an incorrect nucleotide sequence with a correct nucleotide sequence (e.g., to restore function to a target polynucleotide sequence that is impaired due to a loss of function mutation, i.e., a SNP).

The CRISPR/Cas systems of the present invention can alter target polynucleotides with surprisingly high efficiency as compared to conventional CRISPR/Cas systems. In certain embodiments, the efficiency of alteration is at least about 5%. In certain embodiments, the efficiency of alteration is at least about 10%. In certain embodiments, the efficiency of alteration is from about 10% to about 80%. In certain embodiments, the efficiency of alteration is from about 30% to about 80%. In certain embodiments, the efficiency of alteration is from about 50% to about 80%. In some embodiments, the efficiency of alteration is greater than or equal to about 80%.

The CRISPR/Cas systems of the present invention can be used to alter any target polynucleotide sequence in a cell. Those skilled in the art will readily appreciate that desirable target polynucleotide sequences to be altered in any particular cell may correspond to any genomic sequence for which expression of the genomic sequence is associated with a disorder or otherwise facilitates entry of a pathogen into the cell. For example, a desirable target polynucleotide sequence to alter in a cell may be a polynucleotide sequence corresponding to a genomic sequence which contains a disease associated single polynucleotide polymorphism. In such example, the CRISPR/Cas systems of the present invention can be used to correct the disease associated SNP in a cell by replacing it with a wild-type allele. As another example, a polynucleotide sequence of a target gene which is responsible for entry or proliferation of a pathogen into a cell may be a suitable target for deletion or insertion to disrupt the function of the target gene to prevent the pathogen from entering the cell or proliferating inside the cell.

In some embodiments, the target polynucleotide sequence is a genomic sequence. In some embodiments, the target polynucleotide sequence is a human genomic sequence. In some embodiments, the target polynucleotide sequence is a mammalian genomic sequence. In some embodiments, the target polynucleotide sequence is a vertebrate genomic sequence.

In some embodiments, a target polynucleotide sequence is a pathogenic genomic sequence. Exemplary pathogenic genomic sequences include, but are not limited to a viral genomic sequence, a bacterial genomic sequence, a fungal genomic sequence, a toxin genomic sequence, or a parasitic genomic sequence. In such embodiments, the CRISPR/Cas systems of the present invention can be used to disrupt the function of a pathogen (e.g., to treat or prevent an infection by the pathogen) by, cleaving a genomic sequence of the pathogen (e.g., a genomic sequence that is critical for entry into a cell, or responsible for multiplication, growth or survival once the pathogen is inside a cell).

In some embodiments, the target polynucleotide sequence is beta-2-microglobulin (B2M; Gene ID: 567). The B2M polynucleotide sequence encodes a serum protein associated with the heavy chain of the major histocompatibility complex (MHC) class I molecules which are expressed on the surface of virtually all nucleated cells. B2M protein comprises a beta-pleated sheet structure that has been found to form amyloid fibrils in certain pathological conditions. The B2M gene has 4 exons which span approximately 8 kb. B2M has been observed in the serum of normal individuals and in elevated amounts in urine from patients having Wilson disease, cadmium poisoning, and various conditions leading to renal tubular dysfunction. Other pathological conditions known to be associated with the B2M include, without limitation, a homozygous mutation (e.g., ala11pro) in the B2M gene has been reported in individuals having familial hypercatabolic hypoproteinemia, a heterozygous mutation (e.g., asp76asn) in the B2M gene has been reported in individuals having familial visceral amyloidosis In some embodiments, the target polynucleotide sequence is a variant of B2M. In some embodiments, the target polynucleotide sequence is a homolog of B2M. In some embodiments, the target polynucleotide sequence is an ortholog of B2M.

In some embodiments, the target polynucleotide sequence is hypoxanthine phosphoribosyltransferase 1 (HPRT1; Gene ID: 3251).

In some embodiments, the target polynucleotide sequence is CCR5 (Gene ID: 1234, also known as CC-CKR-5, CCCKR5, CCR-5, CD195, CKR-5, CKR5, CMKBR5, and IDDM22). In some embodiments, the target polynucleotide sequence is a variant of CCR5. In some embodiments, the target polynucleotide sequence is a homolog of CCR5. In some embodiments, the target polynucleotide sequence is an ortholog of CCR5.

In some embodiments, the target polynucleotide sequence is CXCR4 (Gene ID: 7852, also known as FB22; HM89; LAP3; LCR1; NPYR; WHIM; CD184; LESTR; NPY3R; NPYRL; HSY3RR; NPYY3R; and D2S201E). In some embodiments, the target polynucleotide sequence is a variant of CXCR4. In some embodiments, the target polynucleotide sequence is a homolog of CXCR4. In some embodiments, the target polynucleotide sequence is an ortholog of CXCR4. It should be appreciated that the CRISPR/Cas systems of the present invention can cleave target polynucleotide sequences in a variety of ways. In some embodiments, the target polynucleotide sequence is cleaved such that a double-strand break results. In some embodiments, the target polynucleotide sequence is cleaved such that a single-strand break results.

The methods of the present invention can be used to alter any target polynucleotide sequence in a cell, as long as the target polynucleotide sequence in the cell contains a suitable target motif that allows at least one ribonucleic acid of the CRISPR/Cas system to direct the Cas protein to and hybridize to the target motif. Those skilled in the art will appreciate that the target motif for targeting a particular polynucleotide depends on the CRISPR/Cas system being used, and the sequence of the polynucleotide to be targeted.

In some embodiments, the target motif is at least 20 bp in length. In some embodiments, the target motif is a 20-nucleotide DNA sequence. In some embodiments, the target motif is a 20-nucleotide DNA sequence beginning with G and immediately precedes an NGG motif recognized by the Cas protein. In some embodiments, the target motif is $G(N)_{19}NGG$. In some embodiments, the target motif is a 20-nucleotide DNA sequence and immediately precedes an NGG motif recognized by the Cas protein. In some embodiments, the target motif is $(N)_{20}NGG$.

The target motifs of the present invention can be selected to minimize off-target effects of the CRISPR/Cas systems of the present invention. In some embodiments, the target motif is selected such that it contains at least two mismatches when compared with all other genomic nucleotide sequences in the cell. In some embodiments, the target motif is selected such that it contains at least one mismatch when compared with all other genomic nucleotide sequences in the cell. Those skilled in the art will appreciate that a variety of techniques can be used to select suitable target motifs for minimizing off-target effects (e.g., bioinformatics analyses).

In some embodiments, the target motif comprises a DNA sequence selected from the group consisting of SEQ ID NOs: 1-139. In some embodiments, the target motif comprises a DNA sequence comprising at least one nucleotide mismatch compared to a DNA sequence selected from the group consisting of SEQ ID NOs: 1-139. In some embodiments, the target motif comprises a DNA sequence comprising at least two nucleotide mismatches compared to a DNA sequence selected from the group consisting of SEQ ID NOs: 1-139. In some embodiments, the target motif comprises a DNA sequence selected from the group consisting of SEQ ID NOs: 140-297. In some embodiments, the target motif comprises a DNA sequence comprising at least one nucleotide mismatch compared to a DNA sequence selected from the group consisting of SEQ ID NOs: 140-297. In some embodiments, the target motif comprises a DNA sequence comprising at least two nucleotide mismatches compared to a DNA sequence selected from the group consisting of SEQ ID NOs: 140-297. In some embodiments, the target motif comprises a DNA sequence selected from the group consisting of SEQ ID NOs: 304-333. In some embodiments, the target motif comprises a DNA sequence comprising at least one nucleotide mismatch compared to a DNA sequence selected from the group consisting of SEQ ID NOs: 304-333. In some embodiments, the target motif comprises a DNA sequence comprising at least two nucleotide mismatches compared to a DNA sequence selected from the group consisting of SEQ ID NOs: 304-333. In some embodiments, the CRISPR/Cas systems of the present invention utilize homology-directed repair to correct target polynucleotide sequences. In some embodiments, subsequent to cleavage of the target polynucleotide sequence, homology-directed repair occurs. In some embodiments, homology-directed repair is performed using an exogenously introduced DNA repair template. The exogenously introduced DNA repair template can be single-stranded or double-stranded. The DNA repair template can be of any length. Those skilled in the art will appreciate that the length of any particular DNA repair template will depend on the target polynucleotide sequence that is to be corrected. The DNA repair template can be designed to repair or replace any target polynucleotide sequence, particularly target polynucleotide sequences comprising disease associated polymorphisms (e.g., SNPs). For example, homology-directed repair of a mutant allele comprising such SNPs can be achieved with a CRISPR/Cas system by selecting two target motifs which flank the mutant allele, and an designing a DNA repair template to match the wild-type allele.

In some embodiments, a CRISPR/Cas system of the present invention includes a Cas protein and at least one to two one ribonucleic acids that are capable of directing the Cas protein to and hybridizing to a target motif of a target polynucleotide sequence.

As used herein, "protein" and "polypeptide" are used interchangeably to refer to a series of amino acid residues joined by peptide bonds (i.e., a polymer of amino acids) and include modified amino acids (e.g., phosphorylated, glycated, glycosolated, etc.) and amino acid analogs. Exemplary polypeptides or proteins include gene products, naturally occurring proteins, homologs, paralogs, fragments and other equivalents, variants, and analogs of the above.

In some embodiments, a Cas protein comprises one or more amino acid substitutions or modifications. In some embodiments, the one or more amino acid substitutions comprises a conservative amino acid substitution. In some instances, substitutions and/or modifications can prevent or reduce proteolytic degradation and/or extend the half-life of the polypeptide in a cell. In some embodiments, the Cas protein can comprise a peptide bond replacement (e.g., urea, thiourea, carbamate, sulfonyl urea, etc.). In some embodiments, the Cas protein can comprise a naturally occurring amino acid. In some embodiments, the Cas protein can comprise an alternative amino acid (e.g., D-amino acids, beta-amino acids, homocysteine, phosphoserine, etc.). In some embodiments, a Cas protein can comprise a modification to include a moiety (e.g., PEGylation, glycosylation, lipidation, acetylation, end-capping, etc.).

In some embodiments, a Cas protein comprises a core Cas protein. Exemplary Cas core proteins include, but are not limited to Cas1, Cas2, Cas3, Cas4, Cas5, Cash, Cas7, Cas8 and Cas9. In some embodiments, a Cas protein comprises a Cas protein of an *E. coli* subtype (also known as CASS2). Exemplary Cas proteins of the *E. Coli* subtype include, but are not limited to Cse1, Cse2, Cse3, Cse4, and Cas5e. In some embodiments, a Cas protein comprises a Cas protein of the Ypest subtype (also known as CASS3). Exemplary Cas proteins of the Ypest subtype include, but are not limited to Csy1, Csy2, Csy3, and Csy4. In some embodiments, a Cas protein comprises a Cas protein of the Nmeni subtype (also known as CASS4). Exemplary Cas proteins of the Nmeni subtype include, but are not limited to Csn1 and Csn2. In some embodiments, a Cas protein comprises a Cas protein of the Dvu1g subtype (also known as CASS1). Exemplary Cas proteins of the Dvu1g subtype include Csd1, Csd2, and Cas5d. In some embodiments, a Cas protein comprises a Cas protein of the Tneap subtype (also known as CASS7). Exemplary Cas proteins of the Tneap subtype include, but are not limited to, Cst1, Cst2, Cas5t. In some embodiments, a Cas protein comprises a Cas protein of the Hmari subtype. Exemplary Cas proteins of the Hmari subtype include, but are not limited to Csh1, Csh2, and Cas5h. In some embodiments, a Cas protein comprises a Cas protein of the Apern subtype (also known as CASS5). Exemplary Cas proteins of the Apern subtype include, but are not limited to Csa1, Csa2, Csa3, Csa4, Csa5, and Cas5a. In some embodiments, a Cas protein comprises a Cas protein of the Mtube subtype (also known as CASS6). Exemplary Cas proteins of the Mtube subtype include, but are not limited to Csm1, Csm2, Csm3, Csm4, and Csm5. In some embodiments, a Cas protein comprises a RAMP module Cas protein. Exemplary RAMP module Cas proteins include, but are not limited to, Cmr1, Cmr2, Cmr3, Cmr4, Cmr5, and Cmr6.

In some embodiments, the Cas protein is a *Streptococcus pyogenes* Cas9 protein or a functional portion thereof. In some embodiments, the Cas protein is Cas9 protein from any bacterial species or functional portion thereof. Cas9 protein is a member of the type II CRISPR systems which typically include a trans-coded small RNA (tracrRNA), endogenous ribonuclease 3 (rnc) and a Cas protein. Cas 9 protein (also known as CRISPR-associated endonuclease Cas9/Csn1) is a polypeptide comprising 1368 amino acids. An exemplary amino acid sequence of a Cas9 protein (SEQ ID NO: 298) is shown in FIG. 3. Cas 9 contains 2 endonuclease domains, including an RuvC-like domain (residues 7-22, 759-766 and 982-989) which cleaves target DNA that is noncomplementary to crRNA, and an HNH nuclease domain (residues 810-872) which cleave target DNA complementary to crRNA. In FIG. 3, the RuvC-like domain is highlighted in yellow and the HNH nuclease domain is underlined.

As used herein, "functional portion" refers to a portion of a peptide which retains its ability to complex with at least one ribonucleic acid (e.g., guide RNA (gRNA)) and cleave a target polynucleotide sequence. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional domains form a complex.

In some embodiments, a functional portion of the Cas9 protein comprises a functional portion of a RuvC-like domain. In some embodiments, a functional portion of the Cas9 protein comprises a functional portion of the HNH nuclease domain.

It should be appreciated that the present invention contemplates various of ways of contacting a target polynucleotide sequence with a Cas protein (e.g., Cas9). In some embodiments, exogenous Cas protein can be introduced into the cell in polypeptide form. In certain embodiments, Cas proteins can be conjugated to or fused to a cell-penetrating polypeptide or cell-penetrating peptide. As used herein, "cell-penetrating polypeptide" and "cell-penetrating peptide" refers to a polypeptide or peptide, respectively, which facilitates the uptake of molecule into a cell. The cell-penetrating polypeptides can contain a detectable label.

In certain embodiments, Cas proteins can be conjugated to or fused to a charged protein (e.g., that carries a positive, negative or overall neutral electric charge). Such linkage may be covalent. In some embodiments, the Cas protein can be fused to a superpositively charged GFP to significantly increase the ability of the Cas protein to penetrate a cell (Cronican et al. *ACS Chem Biol.* 2010; 5(8):747-52).

In certain embodiments, the Cas protein can be fused to a protein transduction domain (PTD) to facilitate its entry into a cell. Exemplary PTDs include Tat, oligoarginine, and penetratin.

In some embodiments, the Cas9 protein comprises a Cas9 polypeptide fused to a cell-penetrating peptide. In some embodiments, the Cas9 protein comprises a Cas9 polypeptide fused to a PTD. In some embodiments, the Cas9 protein comprises a Cas9 polypeptide fused to a tat domain. In some embodiments, the Cas9 protein comprises a Cas9 polypeptide fused to an oligoarginine domain. In some embodiments, the Cas9 protein comprises a Cas9 polypeptide fused to a penetratin domain. In some embodiments, the Cas9 protein comprises a Cas9 polypeptide fused to a superpositively charged GFP.

In some embodiments, the Cas protein can be introduced into a cell containing the target polynucleotide sequence in the form of a nucleic acid encoding the Cas protein (e.g., Cas9). The process of introducing the nucleic acids into cells can be achieved by any suitable technique. Suitable techniques include calcium phosphate or lipid-mediated transfection, electroporation, and transduction or infection using a viral vector. In some embodiments, the nucleic acid comprises DNA. In some embodiments, the nucleic acid comprises a modified DNA, as described herein. In some embodiments, the nucleic acid comprises mRNA. In some embodiments, the nucleic acid comprises a modified mRNA, as described herein (e.g., a synthetic, modified mRNA).

In some embodiments, the Cas protein is complexed with the one to two ribonucleic acids. In some embodiments, the Cas protein is complexed with two ribonucleic acids. In some embodiments, the Cas protein is encoded by a modified nucleic acid, as described herein (e.g., a synthetic, modified mRNA).

The methods of the present invention contemplate the use of any ribonucleic acid that is capable of directing a Cas protein to and hybridizing to a target motif of a target polynucleotide sequence. In some embodiments, at least one of the ribonucleic acids comprises tracrRNA. In some embodiments, at least one of the ribonucleic acids comprises CRISPR RNA (crRNA). In some embodiments, at least one of the ribonucleic acids comprises a guide RNA that directs the Cas protein to and hybridizes to a target motif of the target polynucleotide sequence in a cell. In some embodiments, both of the one to two ribonucleic acids comprise a guide RNA that directs the Cas protein to and hybridizes to a target motif of the target polynucleotide sequence in a cell. The ribonucleic acids of the present invention can be selected to hybridize to a variety of different target motifs, depending on the particular CRISPR/Cas system employed, and the sequence of the target polynucleotide, as will be appreciated by those skilled in the art. The one to two ribonucleic acids can also be selected to minimize hybridization with nucleic acid sequences other than the target polynucleotide sequence. In some embodiments, the one to two ribonucleic acids hybridize to a target motif that contains at least two mismatches when compared with all other genomic nucleotide sequences in the cell. In some embodiments, the one to two ribonucleic acids hybridize to a target motif that contains at least one mismatch when compared with all other genomic nucleotide sequences in the cell. In some embodiments, the one to two ribonucleic acids are designed to hybridize to a target motif immediately adjacent to a deoxyribonucleic acid motif recognized by the Cas protein. In some embodiments, each of the one to two ribonucleic acids are designed to hybridize to target motifs immediately adjacent to deoxyribonucleic acid motifs recognized by the Cas protein which flank a mutant allele located between the target motifs.

In some embodiments, at least one of the one to two ribonucleic acids comprises a sequence selected from the group consisting of the ribonucleic acid sequences of FIG. 1. In some embodiments, at least one of the one to two ribonucleic acids comprises a sequence with a single nucleotide mismatch to a sequence selected from the group consisting of the ribonucleic acid sequences of FIG. 1.

In some embodiments, at least one of the one to two ribonucleic acids comprises a sequence selected from the group consisting of the ribonucleic acid sequences of FIG. 2. In some embodiments, at least one of the one to two ribonucleic acids comprises a sequence with a single nucleotide mismatch to a sequence selected from the group consisting of the ribonucleic acid sequences of FIG. 2.

In some embodiments, each of the one to two ribonucleic acids comprises guide RNAs that directs the Cas protein to and hybridizes to a target motif of the target polynucleotide sequence in a cell. In some embodiments, the two guide RNA sequences comprise any combination of two guide ribonucleic acid sequences selected from the group consisting of SEQ ID NOs: 1-139. In some embodiments, the two guide RNA sequences comprise any combination of two guide ribonucleic acid sequences comprising RNA sequences which are complementary to two different sequences selected from the group consisting of SEQ ID NOs: 1-139. In some embodiments, the two guide RNA sequences comprise any combination of two guide ribonucleic acid sequences comprising RNA sequences which are complementary to two different offset sequences selected from the group consisting of SEQ ID NOs: 1-139. In some embodiments, the two guide RNA sequences comprise any combination of two guide ribonucleic acid sequences comprising RNA sequences which are complementary to two different sequences comprising at least one nucleotide mismatch compared to a sequence selected from the group consisting of SEQ ID NOs: 1-139. In some embodiments, the two guide RNA sequences comprise any combination of two guide ribonucleic acid sequences comprising RNA sequences which are complementary to two different offset sequences comprising at least one nucleotide mismatch compared to a sequence selected from the group consisting of SEQ ID NOs: 1-139. In some embodiments, the two guide RNA sequences comprise any combination of two guide ribonucleic acid sequences comprising RNA sequences which hybridize to two different sequences selected from the group consisting of SEQ ID NOs: 1-139. In some embodiments, the two guide RNA sequences comprise any combination of two guide ribonucleic acid sequences comprising RNA sequences which hybridize to two different offset sequences selected from the group consisting of SEQ ID NOs: 1-139. In some embodiments, the two guide RNA sequences comprise any combination of two guide ribonucleic acid sequences comprising RNA sequences which hybridize to two different sequences comprising at least one nucleotide mismatch compared to a sequence selected from the group consisting of SEQ ID NOs: 1-139. In some embodiments, the two guide RNA sequences comprise any combination of two guide ribonucleic acid sequences comprising RNA sequences which hybridize to two different offset sequences comprising at least one nucleotide mismatch compared to a sequence selected from the group consisting of SEQ ID NOs: 1-139.

In some embodiments, the two guide RNA sequences comprise any combination of two guide ribonucleic acid sequences selected from the group consisting of SEQ ID NOs: 140-297. In some embodiments, the two guide RNA sequences comprise any combination of two guide ribonucleic acid sequences comprising RNA sequences which are complementary to two different sequences selected from the group consisting of SEQ ID NOs: 140-297. In some embodiments, the two guide RNA sequences comprise any combination of two guide ribonucleic acid sequences comprising RNA sequences which are complementary to two different offset sequences selected from the group consisting of SEQ ID NOs: 140-297. In some embodiments, the two guide RNA sequences comprise any combination of two guide ribonucleic acid sequences comprising RNA sequences which are complementary to two different sequences comprising at least one nucleotide mismatch compared to a sequence selected from the group consisting of SEQ ID NOs: 140-297. In some embodiments, the two guide RNA sequences comprise any combination of two guide ribonucleic acid sequences comprising RNA sequences which are complementary to two different offset sequences comprising at least one nucleotide mismatch compared to a sequence selected from the group consisting of SEQ ID NOs: 140-297. In some embodiments, the two guide RNA sequences comprise any combination of two guide ribonucleic acid sequences comprising RNA sequences which hybridize to two different sequences selected from the group consisting of SEQ ID NOs: 140-297. In some embodiments, the two guide RNA sequences comprise any combination of two guide ribonucleic acid sequences comprising RNA sequences which hybridize to two different offset sequences selected from the group consisting of SEQ ID NOs: 140-297. In some embodiments, the two guide RNA sequences comprise any combination of two guide ribonucleic acid sequences comprising RNA sequences which hybridize to two different sequences comprising at least one nucleotide mismatch compared to a sequence selected from the group consisting of SEQ ID NOs: 140-297. In some embodiments, the two guide RNA sequences comprise any combination of two guide ribonucleic acid sequences comprising RNA sequences which hybridize to two different offset sequences comprising at least one nucleotide mismatch compared to a sequence selected from the group consisting of SEQ ID NOs: 140-297.

In some embodiments, the two guide RNA sequences comprise any combination of two guide ribonucleic acid sequences selected from the group consisting of SEQ ID NOs: 298-303. In some embodiments, the two guide ribonucleic acid sequences comprise a pair of guide ribonucleic acids selected from the group consisting of SEQ ID NOs: 299 and 303, SEQ ID NOs: 298 and 300, SEQ ID NOs: 299 and 300, SEQ ID NOs: 298 and 303, SEQ ID NOs: 299 and 301, SEQ ID NOs: 298 and 299, SEQ ID NOs: 301 and 303, SEQ ID NOs: 298 and 302, and SEQ ID NOs: 298 and 301. In some embodiments, the two guide RNA sequences comprise any combination of two guide ribonucleic acid sequences comprising RNA sequences which are complementary to two different sequences selected from the group consisting of SEQ ID NOs: 304-333. In some embodiments, the two guide RNA sequences comprise any combination of two guide ribonucleic acid sequences comprising RNA sequences which are complementary to two different offset sequences selected from the group consisting of SEQ ID NOs: 304-333. In some embodiments, the two guide RNA sequences comprise any combination of two guide ribonucleic acid sequences comprising RNA sequences which are complementary to two different sequences comprising at least one nucleotide mismatch compared to a sequence selected from the group consisting of SEQ ID NOs: 304-333. In some embodiments, the two guide RNA sequences comprise any combination of two guide ribonucleic acid sequences comprising RNA sequences which are complementary to two different offset sequences comprising at least one nucleotide mismatch compared to a sequence selected from the group consisting of SEQ ID NOs: 304-333. In some embodiments, the two guide RNA sequences comprise any combination of two guide ribonucleic acid sequences comprising RNA sequences which hybridize to two different sequences selected from the group consisting of SEQ ID NOs: 304-333. In some embodiments, the two guide RNA sequences comprise any combination of two guide ribonucleic acid sequences comprising RNA sequences which hybridize to two different offset sequences selected from the group consisting of SEQ ID NOs: 304-333. In some embodiments, the two guide RNA sequences comprise any combination of two guide ribonucleic acid sequences comprising RNA sequences which hybridize to two different sequences comprising at least one nucleotide mismatch compared to a sequence selected from the group consisting of SEQ ID NOs: 304-333. In some embodiments, the two guide RNA sequences comprise any combination of two guide ribonucleic acid sequences comprising RNA sequences which hybridize to two different offset sequences comprising at least one nucleotide mismatch compared to a sequence selected from the group consisting of SEQ ID NOs: 304-333.

In some embodiments, the two ribonucleic acids (e.g., guide RNAs) are complementary to and/or hybridize to sequences on the same strand of a target polynucleotide sequence. In some embodiments, the two ribonucleic acids (e.g., guide RNAs) are complementary to and/or hybridize to sequences on the opposite strands of a target polynucleotide sequence. In some embodiments, the two ribonucleic acids (e.g., guide RNAs) are not complementary to and/or do not hybrize to sequences on the opposite strands of a target polynucleotide sequence. In some embodiments, the two ribonucleic acids (e.g., guide RNAs) are complementary to and/or hybridize to overlapping target motifs of a target polynucleotide sequence. In some embodiments, the two ribonucleic acids (e.g., guide RNAs) are complementary to and/or hybridize to offset target motifs of a target polynucleotide sequence.

The present invention also contemplates multiplex genomic editing. Those skilled in the art will appreciate that the description above with respect to genomic editing of a single gene is equally applicable to the multiplex genomic editing embodiments described below.

In another aspect, the present invention provides a method for simultaneously altering multiple target polynucleotide sequences in a cell.

An exemplary method for simultaneously altering multiple target polynucleotide sequences in a cell comprises contacting the polynucleotide sequences with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 50% to about 80%.

In yet another aspect, the present invention provides a method for treating or preventing a disorder associated with expression of polynucleotide sequences in a subject.

An exemplary method for treating or preventing a disorder associated with expression of polynucleotide sequences in a subject comprises (a) altering target polynucleotide sequences in a cell ex vivo by contacting the polynucleotide sequences with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 50% to about 80%, and (b) introducing the cell into the subject, thereby treating or preventing a disorder associated with expression of the polynucleotide sequences.

As used herein, the terms "administering," "introducing" and "transplanting" are used interchangeably in the context of the placement of cells, e.g. cells described herein comprising a target polynucleotide sequence altered according to the methods of the invention into a subject, by a method or route which results in at least partial localization of the introduced cells at a desired site. The cells can be implanted directly to the desired site, or alternatively be administered by any appropriate route which results in delivery to a desired location in the subject where at least a portion of the implanted cells or components of the cells remain viable. The period of viability of the cells after administration to a subject can be as short as a few hours, e. g. twenty-four hours, to a few days, to as long as several years. In some instances, the cells can also be administered a location other than the desired site, such as in the liver or subcutaneously, for example, in a capsule to maintain the implanted cells at the implant location and avoid migration of the implanted cells.

For ex vivo methods, cells can include autologous cells, i.e., a cell or cells taken from a subject who is in need of altering a target polynucleotide sequence in the cell or cells (i.e., the donor and recipient are the same individual). Autologous cells have the advantage of avoiding any immunologically-based rejection of the cells. Alternatively, the cells can be heterologous, e.g., taken from a donor. The second subject can be of the same or different species. Typically, when the cells come from a donor, they will be from a donor who is sufficiently immunologically compatible with the recipient, i.e., will not be subject to transplant rejection, to lessen or remove the need for immunosuppression. In some embodiments, the cells are taken from a xenogeneic source, i.e., a non-human mammal that has been genetically engineered to be sufficiently immunologically compatible with the recipient, or the recipient's species. Methods for determining immunological compatibility are known in the art, and include tissue typing to assess donor-recipient compatibility for HLA and ABO determinants. See, e.g., *Transplantation Immunology*, Bach and Auchincloss, Eds. (Wiley, John & Sons, Incorporated 1994).

Any suitable cell culture media can be used for ex vivo methods of the invention.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

In some embodiments, the alteration results in reduced expression of the target polynucleotide sequences. In some embodiments, the alteration results in a knock out of the target polynucleotide sequences. In some embodiments, the alteration results in correction of the target polynucleotide sequences from undesired sequences to desired sequences. In some embodiments, each alteration is a homozygous alteration. In some embodiments, the efficiency of alteration at each loci is from about 5% to about 80%. In some embodiments, the efficiency of alteration at each loci is from about 10% to about 80%. In some embodiments, the efficiency of alteration at each loci is from about 30% to about 80%. In some embodiments, the efficiency of alteration at each loci is from about 50% to about 80%. In some embodiments, the efficiency of alteration at each loci is from greater than or equal to about 80%.

In some embodiments, each target polynucleotide sequence is cleaved such that a double-strand break results.

In some embodiments, each target polynucleotide sequence is cleaved such that a single-strand break results.

In some embodiments, the target polynucleotide sequences comprise multiple different portions of B2M. In some embodiments, the target polynucleotide sequences comprise multiple different portions of CCR5. In some embodiments, the target polynucleotide sequences comprise multiple different portions of CXCR4. In some embodiments, the target polynucleotide sequences comprise at least a portion of CCR5 and at least a portion of CXCR4.

In some embodiments, each target motif is a 20-nucleotide DNA sequence. In some embodiments, each target motif is a 20-nucleotide DNA sequence beginning with G and immediately precedes an NGG motif recognized by the Cas protein. In some embodiments, each target motif is a 20-nucleotide DNA sequence and immediately precedes an NGG motif recognized by the Cas protein. In some embodiments, each target motif is G(N)19NGG. In some embodiments, each target motif is (N)20NGG. In some embodiments, each target motif is selected such that it contains at least two mismatches when compared with all other genomic nucleotide sequences in the cell. In some embodiments, each target motif is selected such that it contains at least two mismatches when compared with all other genomic nucleotide sequences in the cell.

In some embodiments, each target motif comprises a different DNA sequence selected from the group consisting of SEQ ID NOs: 1-139. In some embodiments, each target motif comprises a different DNA sequence comprising at least one nucleotide mismatch compared to a DNA sequence selected from the group consisting of SEQ ID NOs: 1-139. In some embodiments, each target motif comprises a DNA sequence comprising at least two nucleotide mismatches compared to a DNA sequence selected from the group consisting of SEQ ID NOs: 1-139. In some embodiments, each target motif comprises a different DNA sequence selected from the group consisting of SEQ ID NOs: 140-297. In some embodiments, each target motif comprises a different DNA sequence comprising at least one nucleotide mismatch compared to a DNA sequence selected from the group consisting of SEQ ID NOs: 140-297. In some embodiments, each target motif comprises a different DNA sequence comprising at least two nucleotide mismatches compared to a DNA sequence selected from the group consisting of SEQ ID NOs: 140-297. In some embodiments, each target motif comprises a different DNA sequence selected from the group consisting of SEQ ID NOs: 304-333. In some embodiments, each target motif comprises a different DNA sequence comprising at least one nucleotide mismatch compared to a DNA sequence selected from the group consisting of SEQ ID NOs: 304-333. In some embodiments, each target motif comprises a different DNA sequence comprising at least two nucleotide mismatches compared to a DNA sequence selected from the group consisting of SEQ ID NOs: 304-333.

In some embodiments, subsequent to cleavage of the target polynucleotide sequences, homology-directed repair occurs. In some embodiments, homology-directed repair is performed using an exogenously introduced DNA repair template. In some embodiments, exogenously introduced DNA repair template is single-stranded. In some embodiments, exogenously introduced DNA repair template is double-stranded.

In some embodiments, the Cas protein (e.g., Cas9) is complexed with the multiple ribonucleic acids. In some embodiments, the multiple ribonucleic acids are selected to minimize hybridization with nucleic acid sequences other than the target polynucleotide sequence (e.g., multiple alterations of a single target polynucleotide sequence). In some embodiments, the multiple ribonucleic acids are selected to minimize hybridization with nucleic acid sequences other than the target polynucleotide sequences (e.g., one or more alterations of multiple target polynucleotide sequences). In some embodiments, each of the multiple ribonucleic acids hybridize to target motifs that contain at least two mismatches when compared with all other genomic nucleotide sequences in the cell. In some embodiments, each of the multiple ribonucleic acids hybridize to target motifs that contain at least one mismatch when compared with all other genomic nucleotide sequences in the cell. In some embodiments, each of the multiple ribonucleic acids are designed to hybridize to target motifs immediately adjacent to deoxyribonucleic acid motifs recognized by the Cas protein. In some embodiments, each of the multiple ribonucleic acids are designed to hybridize to target motifs immediately adjacent to deoxyribonucleic acid motifs recognized by the Cas protein which flank mutant alleles located between the target motifs.

In some embodiments, each of the multiple ribonucleic acids comprises a different sequence selected from the group consisting of the ribonucleic acid sequences of FIG. 1. In some embodiments, each of the multiple ribonucleic acids comprises a sequence with a single nucleotide mismatch to a different sequence selected from the group consisting of the ribonucleic acid sequences of FIG. 1. In some embodiments, each of the multiple ribonucleic acids comprises a different sequence selected from the group consisting of the ribonucleic acid sequences of FIG. 2. In some embodiments, each of the multiple ribonucleic acids comprises a sequence with a single nucleotide mismatch to a different sequence selected from the group consisting of the ribonucleic acid sequences of FIG. 2. In some embodiments, each of the multiple ribonucleic acids comprises a different sequence selected from the group consisting of the ribonucleic acid sequences of FIG. 1 and the ribonucleic acid sequences of FIG. 2. In some embodiments, each of the multiple ribonucleic acids comprises a sequence with a single nucleotide mismatch to a different sequence selected from the group consisting of the ribonucleic acid sequences of FIG. 1 and the ribonucleic acid sequences of FIG. 2.

In some embodiments, each of the multiple ribonucleic acids comprises a different ribonucleic acid sequence which is complementary to and/or hybridizes to a sequence selected from the group consisting of SEQ ID NOs: 1-139 (FIG. 1). In some embodiments, each of the multiple ribonucleic acids comprises a different ribonucleic acid sequence which is complementary to and/or hybridizes to a sequence with a single nucleotide mismatch to a sequence selected from the group consisting of SEQ ID NOs: 1-139 (FIG. 1). In some embodiments, each of the multiple ribonucleic acids comprises a different ribonucleic acid sequence which is complementary to and/or hybridizes to a sequence selected from the group consisting of SEQ ID NOs: 140-297 (FIG. 2). In some embodiments, each of the multiple ribonucleic acids comprises a different ribonucleic acid sequence which is complementary to and/or hybridizes to a sequence with a single nucleotide mismatch to a sequence selected from the group consisting of SEQ ID NOs: 140-297 (FIG. 2).

In some embodiments, each of the multiple ribonucleic acids comprises a different sequence selected from the group consisting of the ribonucleic acid sequences of SEQ ID NOs: 298-303. In some embodiments, each of the multiple ribonucleic acids comprises a different ribonucleic acid sequence which is complementary to and/or hybridizes to a sequence selected from the group consisting of SEQ ID NOs: 304-333. In some embodiments, each of the multiple ribonucleic acids comprises a different ribonucleic acid sequence which is complementary to and/or hybridizes to a sequence with a single nucleotide mismatch to a sequence selected from the group consisting of SEQ ID NOs: 304-333.

It should be appreciated that any of the Cas protein or the ribonucleic acids can be expressed from a plasmid. In some embodiments, any of the Cas protein or the ribonucleic acids are expressed using a promoter optimized for increased expression in stem cells (e.g., human stem cells). In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter.

In some embodiments, the methods of the present invention further comprise selecting cells that express the Cas protein. The present invention contemplates any suitable method for selecting cells. In some embodiments, selecting cells comprises FACS. In some embodiments, FACs is used to select cells which co-express Cas and a fluorescent protein selected from the group consisting of green fluorescent protein and red fluorescent protein.

The present invention contemplates treating and/or preventing a variety of disorders which are associated with expression of a target polynucleotide sequences. It should be appreciated that the methods and compositions described herein can be used to treat or prevent disorders associated with increased expression of a target polynucleotide sequence, as well as decreased expression of a target polynucleotide sequence in a cell. Increased and decreased expression of a target polynucleotide sequence includes circumstances where the expression levels of the target polynucleotide sequence are increased or decreased, respectively, as well as circumstances in which the function and/or level of activity of an expression product of the target polynucleotide sequence increases or decreases, respectively, compared to normal expression and/or activity levels. Those skilled in the art will appreciate that treating or preventing a disorder associated with increased expression of a target polynucleotide sequence can be assessed by determining whether the levels and/or activity of the target polynucleotide sequence (or an expression product thereof) are decreased in a relevant cell after contacting a cell with a composition described herein. The skilled artisan will also appreciate that treating or preventing a disorder associated with decreased expression of a target polynucleotide sequence can be assessed by determining whether the levels and/or activity of the target polynucleotide sequence (or an expression product thereof) are increased in the relevant cell after contacting a cell with a composition described herein.

In some embodiments, the disorder is a genetic disorder. In some embodiments, the disorder is a monogenic disorder. In some embodiments, the disorder is a multigenic disorder. In some embodiments, the disorder is a disorder associated with one or more SNPs. Exemplary disorders associated with one or more SNPs include a complex disease described in U.S. Pat. No. 7,627,436, Alzheimer's disease as described in PCT International Application Publication No. WO/2009/112882, inflammatory diseases as described in U.S. Patent Application Publication No. 2011/0039918, polycystic ovary syndrome as described in U.S. Patent Application Publication No. 2012/0309642, cardiovascular disease as described in U.S. Pat. No. 7,732,139, Huntington's disease as described in U.S. Patent Application Publication No. 2012/0136039, thromboembolic disease as described in European Patent Application Publication No. EP2535424, neurovascular diseases as described in PCT International Application Publication No. WO/2012/001613, psychosis as described in U.S. Patent Application Publication No. 2010/0292211, multiple sclerosis as described in U.S. Patent Application Publication No. 2011/0319288, schizophrenia, schizoaffective disorder, and bipolar disorder as described in PCT International Application Publication No. WO/2006/023719A2, bipolar disorder and other ailments as described in U.S. Patent Application Publication No. U.S. 2011/0104674, colorectal cancer as described in PCT International Application Publication No. WO/2006/104370A1, a disorder associated with a SNP adjacent to the AKT1 gene locus as described in U.S. Patent Application Publication No. U.S. 2006/0204969, an eating disorder as described in PCT International Application Publication No. WO/2003/012143A1, autoimmune disease as described in U.S. Patent Application Publication No. U.S. 2007/0269827, fibrostenosing disease in patients with Crohn's disease as described in U.S. Pat. No. 7,790,370, and Parkinson's disease as described in U.S. Pat. No. 8,187,811, each of which is incorporated herein by reference in its entirety. Other disorders associated with one or more SNPs which can be treated or prevented according to the methods of the present invention will be apparent to the skilled artisan.

In some embodiments, the disorder is human immunodeficiency virus (HIV) infection. In some embodiments, the disorder is acquired immunodeficiency syndrome (AIDS).

The methods of the present invention are capable of altering target polynucleotide sequences in a variety of different cells. In some embodiments, the methods of the present invention are used to alter target polynucleotide sequences in cells ex vivo for subsequent introduction into a subject. In some embodiments, the cell is a peripheral blood cell. In some embodiments, the cell is a stem cell or a pluripotent cell. In some embodiments, the cell is a hematopoietic stem cell. In some embodiments, the cell is a CD34+ cell. In some embodiments, the cell is a CD34+ mobilized peripheral blood cell. In some embodiments, the cell is a CD34+ cord blood cell. In some embodiments, the cell is a CD34+ bone marrow cell. In some embodiments, the cell is a CD34+CD38-Lineage-CD90+CD45RA– cell. In some embodiments, the cell is a CD4+ cell. In some embodiments, the cell is a CD4+ T cell. In some embodiments, the cell is a hepatocyte. In some embodiments, the cell is a human pluripotent cell. In some embodiments, the cell is a primary human cell. In some embodiments, the cell is a primary CD34+ cell. In some embodiments, the cell is a primary CD34+ hematopoietic progenitor cell (HPC). In some embodiments, the cell is a primary CD4+ cell. In some embodiments, the cell is a primary CD4+ T cell. In some embodiments, the cell is an autologous primary cell. In some embodiments, the cell is an autologous primary somatic cell. In some embodiments, the cell is an allogeneic primary cell. In some embodiments, the cell is an allogeneic primary somatic cell. In some embodiments, the cell is a nucleated cell. In some embodiments, the cell is a non-transformed cell. In some embodiments, the cell is not a cancer cell. In some embodiments, the cell is not a tumor cell. In some embodiments, the cell is not a transformed cell.

In some aspects, the present invention provides a method for altering a target polynucleotide sequence in a cell comprising contacting the polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target polynucleotide sequence, wherein the target polynucleotide sequence is cleaved, and wherein the efficiency of alteration of cells that express Cas protein is from about 8% to about 80%.

In some aspects, the present invention provides a method for treating or preventing a disorder associated with expression of a polynucleotide sequence in a subject, the method comprising (a) altering a target polynucleotide sequence in a cell ex vivo by contacting the polynucleotide sequence in a cell selected from the group consisting of a human pluripotent cell, a primary human cell, and a non-transformed human cell, with a clustered regularly interspaced short palindromic repeats-associated (Cas) protein and from one to two ribonucleic acids, wherein the ribonucleic acids direct Cas protein to and hybridize to a target motif of the target polynucleotide sequence, wherein the target polynucleotide sequence is cleaved, and wherein the efficiency of alteration is from about 8% to about 80%, and (b) introducing the cell into the subject, thereby treating or preventing a disorder associated with expression of the polynucleotide sequence.

In some aspects, the present invention provides a method for simultaneously altering multiple target polynucleotide sequences in a cell comprising contacting the polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 8% to about 80%.

In some aspects, the present invention provides a method for treating or preventing a disorder associated with expression of polynucleotide sequences in a subject, the method comprising (a) altering target polynucleotide sequences in a cell ex vivo by contacting the polynucleotide sequences in a cell selected from the group consisting of a human pluripotent cell, a primary human cell, and a non-transformed human cell, with a clustered regularly interspaced short palindromic repeats-associated (Cas) protein and multiple ribonucleic acids, wherein the ribonucleic acids direct Cas protein to and hybridize to target motifs of the target polynucleotide sequences, wherein the target polynucleotide sequences are cleaved, and wherein the efficiency of alteration of cells that express Cas protein is from about 8% to about 80%, and (b) introducing the cell into the subject, thereby treating or preventing a disorder associated with expression of the polynucleotide sequences.

The present invention also provides compositions comprising Cas proteins of the present invention or functional portions thereof, nucleic acids encoding the Cas proteins or functional portions thereof, and ribonucleic acid sequences which direct Cas proteins to and hybridize to target motifs of target polynucleotides in a cell.

In some aspects, the present invention provides a composition comprising at least one ribonucleic acid having a sequence selected from the group consisting of the ribonucleic acid sequences of FIG. 1. In some aspects, the present invention provides a composition comprising at least one ribonucleic acid having a sequence which is complementary to and/or hybridizes to a sequence selected from the group consisting of SEQ ID NOs: 1-139 (FIG. 1).

In some aspects, the present invention provides a composition comprising at least one ribonucleic acid comprising a sequence with a single nucleotide mismatch to a sequence selected from the group consisting of the ribonucleic acid sequences of FIG. 1. In some aspects, the present invention provides a composition comprising at least one ribonucleic acid having a sequence which is complementary to and/or hybridizes to a sequence with a single nucleotide mismatch to a sequence selected from the group consisting of SEQ ID NOs: 1-139 (FIG. 1).

In some aspects, the present invention provides a composition comprising at least one ribonucleic acid having a sequence selected from the group consisting of the ribonucleic acid sequences of FIG. 2. In some aspects, the present invention provides a composition comprising at least one ribonucleic acid having a sequence which is complementary to and/or hybridizes to a sequence selected from the group consisting of SEQ ID NOs: 140-297 (FIG. 2).

In some aspects, the present invention provides a composition comprising at least one ribonucleic acid comprising a sequence with a single nucleotide mismatch to a sequence selected from the group consisting of the ribonucleic acid sequences of FIG. 2. In some aspects, the present invention provides a composition comprising at least one ribonucleic acid having a sequence which is complementary to and/or hybridizes to a sequence with a single nucleotide mismatch to a sequence selected from the group consisting of SEQ ID NOs: 140-297 (FIG. 2).

In some aspects, the present invention provides a composition comprising at least one ribonucleic acid having a sequence selected from the group consisting of the ribonucleic acid sequences of SEQ ID NOs: 298-303. In some aspects, the present invention provides a composition comprising at least one ribonucleic acid having a sequence which is complementary to and/or hybridizes to a sequence selected from the group consisting of SEQ ID NOs: 304-333. In some aspects, the present invention provides a composition comprising at least one ribonucleic acid having a sequence which is complementary to and/or hybridizes to a sequence comprising at least one nucleotide mismatch compared to a sequence selected from the group consisting of SEQ ID NOs: 304-333. In some aspects, the present invention provides a composition comprising at least one ribonucleic acid having a sequence selected from the group consisting of the ribonucleic acid sequences of FIG. 1, the ribonucleic acid sequences of FIG. 2, a sequence with a single nucleotide mismatch to a ribonucleic acid sequence of FIG. 1, and a sequence with a single nucleotide mismatch to a ribonucleic acid sequences of FIG. 2.

In some embodiments, at least one of the ribonucleic acids in the composition is a modified ribonucleic acid as described herein (e.g., a synthetic, modified ribonucleic acid, e.g., comprising one to two modified nucleotides selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate, or any other modified nucleotides or modifications described herein).

In some embodiments, a composition of the present invention comprises a nucleic acid sequence encoding a Cas protein. In some embodiments, a composition of the present invention comprises nucleic acid sequence encoding Cas9 protein or a functional portion thereof.

In some embodiments, the nucleic acid encoding the Cas protein (e.g., Cas9) comprises a modified ribonucleic acid as described herein (e.g., a synthetic, modified mRNA described herein, e.g., comprising at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate or any other modified nucleotides or modifications described herein).

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 1. In some aspects, the present invention provides a composition comprising a chimeric nucleic acid comprising a ribonucleic acid encoding a Cas protein and at least one additional ribonucleic acid having a sequence which is complementary to and/or hybridizes to a sequence selected from the group consisting of SEQ ID NOs: 1-139 (FIG. 1). In some aspects, the present invention provides a composition comprising a chimeric nucleic acid comprising a ribonucleic acid encoding a Cas protein and two additional ribonucleic acid each having a sequence which is complementary to and/or hybridizes to a different sequence selected from the group consisting of SEQ ID NOs: 1-139 (FIG. 1). In some aspects, the present invention provides a composition comprising a chimeric nucleic acid comprising a ribonucleic acid encoding a Cas protein and two additional ribonucleic acid each having a sequence which is complementary to and/or hybridizes to an offset sequence selected from the group consisting of SEQ ID NOs: 1-139 (FIG. 1). In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 2. In some aspects, the present invention provides a composition comprising a chimeric nucleic acid comprising a ribonucleic acid encoding a Cas protein and at least one additional ribonucleic acid having a sequence which is complementary to and/or hybridizes to a sequence selected from the group consisting of SEQ ID NOs: 140-297 (FIG. 2). In some aspects, the present invention provides a composition comprising a chimeric nucleic acid comprising a ribonucleic acid encoding a Cas protein and two additional ribonucleic acids each having a sequence which is complementary to and/or hybridizes to a different sequence selected from the group consisting of SEQ ID NOs: 140-297 (FIG. 2). In some aspects, the present invention provides a composition comprising a chimeric nucleic acid comprising a ribonucleic acid encoding a Cas protein and two additional ribonucleic acids each having a sequence which is complementary to and/or hybridizes to an offset sequence selected from the group consisting of SEQ ID NOs: 140-297 (FIG. 2).

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 1. In some aspects, the present invention provides a composition comprising a chimeric nucleic acid comprising a ribonucleic acid encoding a Cas protein and at least one additional ribonucleic acid sequence which is complementary to and/or hybridizes to a sequence with a single nucleotide mismatch to a sequence selected from the group consisting of SEQ ID NOs: 1-139 (FIG. 1). In some aspects, the present invention provides a composition comprising a chimeric nucleic acid comprising a ribonucleic acid encoding a Cas protein and two additional ribonucleic acid sequences each of which are complementary to and/or hybridize to different sequences with single nucleotide mismatches to a sequence selected from the group consisting of SEQ ID NOs: 1-139 (FIG. 1). In some aspects, the present invention provides a composition comprising a chimeric nucleic acid comprising a ribonucleic acid encoding a Cas protein and two additional ribonucleic acid sequences each of which are complementary to and/or hybridize to offset sequences with single nucleotide mismatches to a sequence selected from the group consisting of SEQ ID NOs: 1-139 (FIG. 1).

In some aspects, the present invention provides a composition comprising a chimeric nucleic acid comprising a ribonucleic acid encoding a Cas protein and at least one additional ribonucleic acid sequence comprising a sequence with a single nucleotide mismatch to a sequence selected from the group consisting of the ribonucleic acid sequences of FIG. 2. In some aspects, the present invention provides a composition comprising a chimeric nucleic acid comprising a ribonucleic acid encoding a Cas protein and at least one additional ribonucleic acid sequence which is complementary to and/or hybridizes to a sequence with a single nucleotide mismatch to a sequence selected from the group consisting of SEQ ID NOs: 140-297 (FIG. 1). In some aspects, the present invention provides a composition comprising a chimeric nucleic acid comprising a ribonucleic acid encoding a Cas protein and two additional ribonucleic acid sequences each of which is complementary to and/or hybridizes to a different sequence with a single nucleotide mismatch to a sequence selected from the group consisting of SEQ ID NOs: 140-297 (FIG. 1). In some aspects, the present invention provides a composition comprising a chimeric nucleic acid comprising a ribonucleic acid encoding a Cas protein and two additional ribonucleic acid sequences each of which is complementary to and/or hybridizes to an offset sequence with a single nucleotide mismatch to a sequence selected from the group consisting of SEQ ID NOs: 140-297 (FIG. 1).

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of SEQ ID NOs: 298-303.

In some aspects, the present invention provides a composition comprising a chimeric nucleic acid comprising a ribonucleic acid encoding a Cas protein and at least two additional ribonucleic acid having a sequence selected from the group consisting of the ribonucleic acid sequences of SEQ ID NOs: 298-303.

In some aspects, the present invention provides a composition comprising a chimeric nucleic acid comprising a ribonucleic acid encoding a Cas protein and two guide ribonucleic acids comprising SEQ ID NOs: 299 and 303. In some aspects, the present invention provides a composition comprising a chimeric nucleic acid comprising a ribonucleic acid encoding a Cas protein and two guide ribonucleic acids comprising SEQ ID NOs: 298 and 300. In some aspects, the present invention provides a composition comprising a chimeric nucleic acid comprising a ribonucleic acid encoding a Cas protein and two guide ribonucleic acids comprising SEQ ID NOs: 299 and 300. In some aspects, the present invention provides a composition comprising a chimeric nucleic acid comprising a ribonucleic acid encoding a Cas protein and two guide ribonucleic acids comprising SEQ ID NOs: 298 and 303. In some aspects, the present invention provides a composition comprising a chimeric nucleic acid comprising a ribonucleic acid encoding a Cas protein and two guide ribonucleic acids comprising SEQ ID NOs: 299 and 301. In some aspects, the present invention provides a composition comprising a chimeric nucleic acid comprising a ribonucleic acid encoding a Cas protein and two guide ribonucleic acids comprising SEQ ID NOs: 298 and 299. In some aspects, the present invention provides a composition comprising a chimeric nucleic acid comprising a ribonucleic acid encoding a Cas protein and two guide ribonucleic acids comprising SEQ ID NOs: 301 and 303. In some aspects, the present invention provides a composition comprising a chimeric nucleic acid comprising a ribonucleic acid encoding a Cas protein and two guide ribonucleic acids comprising SEQ ID NOs: 298 and 302. In some aspects, the present invention provides a composition comprising a chimeric nucleic acid comprising a ribonucleic acid encoding a Cas protein and two guide ribonucleic acids comprising SEQ ID NOs: 298 and 301.

In some aspects, the present invention provides a composition comprising at least one ribonucleic acid having a sequence which is complementary to and/or hybridizes to a sequence selected from the group consisting of SEQ ID NOs: 304-333. In some aspects, the present invention provides a composition comprising at least two ribonucleic acids each having a sequence which is complementary to and/or hybridizes to a different sequence selected from the group consisting of SEQ ID NOs: 304-333. In some aspects, the present invention provides a composition comprising at least two ribonucleic acids each having a sequence which is complementary to and/or hybridizes to an offset sequence selected from the group consisting of SEQ ID NOs: 304-333. In some aspects, the present invention provides a composition comprising at least one ribonucleic acid having a sequence which is complementary to and/or hybridizes to a sequence comprising at least one nucleotide mismatch compared to a sequence selected from the group consisting of SEQ ID NOs: 304-333. In some aspects, the present invention provides a composition comprising at least two ribonucleic acids each having a sequence which is complementary to and/or hybridizes to a different sequence comprising at least one nucleotide mismatch compared to a sequence selected from the group consisting of SEQ ID NOs: 304-333. In some aspects, the present invention provides a composition comprising at least two ribonucleic acids each having a sequence which is complementary to and/or hybridizes to an offset sequence comprising at least one nucleotide mismatch compared to a sequence selected from the group consisting of SEQ ID NOs: 304-333.

In some aspects, the present invention provides a composition comprising a chimeric nucleic acid comprising a ribonucleic acid encoding a Cas protein and at least one additional ribonucleic acid having a sequence selected from the group consisting of the ribonucleic acid sequences of FIG. 1, the ribonucleic acid sequences of FIG. 2, a sequence with a single nucleotide mismatch to a ribonucleic acid sequence of FIG. 1, and a sequence with a single nucleotide mismatch to a ribonucleic acid sequences of FIG. 2.

In some embodiments, a composition of the present invention comprises a nucleic acid sequence encoding a fluorescent protein selected from the group consisting of green fluorescent protein and red fluorescent protein. In some embodiments, a composition of the present invention comprises a promoter operably linked to the chimeric nucleic acid. In some embodiments, the promoter is optimized for increased expression in human stem cells. In some embodiments, the promoter is optimized for increased expression in primary human cells. In some embodiments, the promoter is selected from the group consisting of a Cytomegalovirus (CMV) early enhancer element and a chicken beta-actin promoter, a chicken beta-actin promoter, an elongation factor-1 alpha promoter, and a ubiquitin promoter.

In some embodiments, the Cas protein comprises a Cas9 protein or a functional portion thereof.

The present invention also provides kits for practicing any of the methods of the present invention, as well as kits comprising the compositions of the present invention, and instructions for using the kits for altering target polynucleotide sequences in a cell.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of FIG. 1, the ribonucleic acid sequences of FIG. 2, a sequence with a single nucleotide mismatch to a ribonucleic acid sequence of FIG. 1, and a sequence with a single nucleotide mismatch to a ribonucleic acid sequences of FIG. 2.

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of SEQ ID NO: 1-139 (FIG. 1).

In some aspects, the present invention comprises a kit for altering a target polynucleotide sequence in a cell comprising a Cas9 protein or a nucleic acid encoding the Cas9 protein, and at least one ribonucleic acid sequence which is complementary to and/or hybridizes to a sequence selected from the group consisting of SEQ ID NO: 1-139 (FIG. 1).

In some aspects, the present invention comprises a kit for altering a target polynucleotide sequence in a cell comprising a Cas9 protein or a nucleic acid encoding the Cas9 protein, and at least one ribonucleic acid sequence which is complementary to and/or hybridizes to a sequence comprising at least one nucleotide mismatch to a sequence selected from the group consisting of SEQ ID NO: 1-139 (FIG. 1).

In some aspects, the present invention comprises a kit for altering a target polynucleotide sequence in a cell comprising a Cas9 protein or a nucleic acid encoding the Cas9 protein, and at least two ribonucleic acid sequences selected from the group consisting of the ribonucleic acid sequences of SEQ ID NO: 1-139 (FIG. 1).

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to a different sequence selected from the group consisting of SEQ ID NO: 1-139 (FIG. 1).

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to an offset sequence selected from the group consisting of SEQ ID NO: 1-139 (FIG. 1).

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to a different sequence comprising at least one nucleotide mismatch to a sequence selected from the group consisting of SEQ ID NO: 1-139 (FIG. 1).

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to an offset sequence comprising at least one nucleotide mismatch to a sequence selected from the group consisting of SEQ ID NO: 1-139 (FIG. 1).

In some aspects, the present invention comprises a kit for altering a target polynucleotide sequence in a cell comprising a Cas9 protein or a nucleic acid encoding the Cas9 protein, and at least one ribonucleic acid sequence selected from the group consisting of the ribonucleic acid sequences of SEQ ID NO: 140-297 (FIG. 2).

In some aspects, the present invention comprises a kit for altering a target polynucleotide sequence in a cell comprising a Cas9 protein or a nucleic acid encoding the Cas9 protein, and at least one ribonucleic acid sequence which is complementary to and/or hybridizes to a sequence selected from the group consisting of SEQ ID NO: 140-297 (FIG. 2).

In some aspects, the present invention comprises a kit for altering a target polynucleotide sequence in a cell comprising a Cas9 protein or a nucleic acid encoding the Cas9 protein, and at least one ribonucleic acid sequence which is complementary to and/or hybridizes to a sequence comprising at least one nucleotide mismatch to a sequence selected from the group consisting of SEQ ID NO: 140-297 (FIG. 2).

In some aspects, the present invention comprises a kit for altering a target polynucleotide sequence in a cell comprising a Cas9 protein or a nucleic acid encoding the Cas9 protein, and at least two ribonucleic acid sequences selected from the group consisting of the ribonucleic acid sequences of SEQ ID NO: 140-297 (FIG. 2).

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to a different sequence selected from the group consisting of SEQ ID NO: 140-297 (FIG. 2).

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to an offset sequence selected from the group consisting of SEQ ID NO: 140-297 (FIG. 2).

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to a different sequence comprising at least one nucleotide mismatch to a sequence selected from the group consisting of SEQ ID NO: 140-297 (FIG. 2).

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to an offset sequence comprising at least one nucleotide mismatch to a sequence selected from the group consisting of SEQ ID NO: 140-297 (FIG. 2).

In some aspects, the present invention comprises a kit for altering a target polynucleotide sequence in a cell comprising a Cas9 protein or a nucleic acid encoding the Cas9 protein, and at least two ribonucleic acid sequences selected from the group consisting of the ribonucleic acid sequences of SEQ ID NO: 298-303. In some embodiments, the at least two ribonucleic acid sequences of SEQ ID NO: 298-303 are complementary to and/or hybridize to offset target sequences.

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to a different sequence selected from the group consisting of SEQ ID NO: 304-333.

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/of hybridizes to an offset sequence selected from the group consisting of SEQ ID NO: 304-333.

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to a different sequence comprising at least one nucleotide mismatch to a sequence selected from the group consisting of SEQ ID NO: 304-333.

In some aspects, the present invention comprises a kit for altering a target polynucleotide sequence in a cell comprising a Cas9 protein or a nucleic acid encoding the Cas9 protein, and at least two ribonucleic acid sequences each of which is complementary to and/or hybridizes to an offset sequence comprising at least one nucleotide mismatch to a sequence selected from the group consisting of SEQ ID NO: 304-333.

In some embodiments, the kit comprises one or more cell lines, cultures, or populations selected from the group consisting of human pluripotent cells, primary human cells, and non-transformed cells. In some embodiments, the kit comprises a DNA repair template.

In some aspects, the invention provides a method of administering cells to a subject in need of such cells, the method comprising: (a) contacting a cell or population of cells ex vivo with a Cas protein and two ribonucleic acids which direct Cas protein to and hybridize to a target polynucleotide sequence encoding B2M in the cell or population of cells, wherein the target polynucleotide sequence is cleaved; and (b) administering the resulting cells from (a) to a subject in need of such cells.

In some aspects, the invention provides a method of administering cells to a subject in need of such cells, the method comprising: (a) contacting a cell or population of cells ex vivo with (i) a Cas protein, (ii) at least two ribonucleic acids which direct Cas protein to and hybridize to a target polynucleotide sequence encoding B2M in the cell or population of cells, and (iii) at least two additional ribonucleic acids which direct Cas protein to and hybridize to a target polynucleotide sequence in the cell or population of cells, wherein the target polynucleotide sequences are cleaved; and (b) administering the resulting cell or cells from (a) to a subject in need of such cells.

B2M is an accessory chain of the MHC class I proteins which is necessary for the expression of MHC class I proteins on the surface of cells. It is believed that engineering cells (e.g., mutant cells) devoid of surface MHC class I may reduce the likelihood that the engineered cells will be detected by cytotoxic T cells when the engineered cells are administered to a host. Accordingly, in some embodiments, cleavage of the target polynucleotide sequence encoding B2M in the cell or population of cells reduces the likelihood that the resulting cell or cells will trigger a host immune response when the cells are administered to the subject.

In some aspects, the invention provides a method of reducing the likelihood that cells administered to a subject will trigger a host immune response in the subject, the method comprising: (a) contacting a cell or population of cells ex vivo with a Cas protein and two ribonucleic acids which direct Cas protein to and hybridize to a target polynucleotide sequence encoding B2M in the cell or population of cells, wherein the target polynucleotide sequence encoding B2M is cleaved, thereby reducing the likelihood that cells administered to the subject will trigger a host immune response in the subject; and (b) administering the resulting cells from (a) to a subject in need of such cells.

In some aspects, the invention provides a method of reducing the likelihood that cells administered to a subject will trigger a host immune response in the subject, the method comprising: (a) contacting a cell or population of cells ex vivo with (i) a Cas protein, (ii) at least two ribonucleic acids which direct Cas protein to and hybridize to a target polynucleotide sequence encoding B2M in the cell or population of cells, wherein the target polynucleotide sequence encoding B2M in the cell or population of cells is cleaved, thereby reducing the likelihood that the cell or population of cells will trigger a host immune response in the subject, and (iii) at least two additional ribonucleic acids which direct Cas protein to and hybridize to a target polynucleotide sequence in the cell or population of cells, wherein the target polynucleotide sequence is cleaved; and (b) administering the resulting cell or cells from (a) to a subject in need of such cells.

It is contemplated that the methods of administering cells can be adapted for any purpose in which administering such cells is desirable. In some embodiments, the subject in need of administration of cells is suffering from a disorder. For example, the subject may be suffering from a disorder in which the particular cells are decreased in function or number, and it may be desirable to administer functional cells obtained from a healthy or normal individual in which the particular cells are functioning properly and to administer an adequate number of those healthy cells to the individual to restore the function provided by those cells (e.g., hormone producing cells which have decreased in cell number or function, immune cells which have decreased in cell number or function, etc.). In such instances, the healthy cells can be engineered to decrease the likelihood of host rejection of the healthy cells. In some embodiments, the disorder comprises a genetic disorder. In some embodiments, the disorder comprises an infection. In some embodiments, the disorder comprises HIV or AIDS. In some embodiments, the disorder comprises cancer.

In some aspects, the invention provides a method of reducing the likelihood that cells administered to a subject will trigger a host immune response in the subject, the method comprising: (a) contacting a cell or population of cells ex vivo with a Cas protein and two ribonucleic acids which direct Cas protein to and hybridize to a target polynucleotide sequence encoding B2M in the cell or population of cells, wherein the target polynucleotide sequence encoding B2M is cleaved, thereby reducing the likelihood that cells administered to the subject will trigger a host immune response in the subject; and (b) administering the resulting cells from (a) to a subject in need of such cells.

In some aspects, the invention provides a method of reducing the likelihood that cells administered to a subject will trigger a host immune response in the subject, the method comprising: (a) contacting a cell or population of cells ex vivo with (i) a Cas protein, (ii) at least two ribonucleic acids which direct Cas protein to and hybridize to a target polynucleotide sequence encoding B2M in the cell or population of cells, wherein the target polynucleotide sequence encoding B2M in the cell or population of cells is cleaved, thereby reducing the likelihood that the cell or population of cells will trigger a host immune response in the subject, and (iii) at least two additional ribonucleic acids which direct Cas protein to and hybridize to a target polynucleotide sequence in the cell or population of cells, wherein the target polynucleotide sequence is cleaved; and (b) administering the resulting cell or cells from (a) to a subject in need of such cells. As used herein "nucleic acid," in its broadest sense, includes any compound and/or substance that comprise a polymer of nucleotides linked via a phosphodiester bond. Exemplary nucleic acids include ribonucleic acids (RNAs), deoxyribonucleic acids (DNAs), threose nucleic acids (TNAs), glycol nucleic acids (GNAs), peptide nucleic acids (PNAs), locked nucleic acids (LNAs) or hybrids thereof. They may also include RNAi-inducing agents, RNAi agents, siRNAs, shRNAs, miRNAs, antisense RNAs, ribozymes, catalytic DNA, tRNA, RNAs that induce triple helix formation, aptamers, vectors, etc. In some embodiments, the nucleic acid encoding the Cas protein is an mRNA. In some embodiments, the Cas protein is encoded by a modified nucleic acid (e.g., a synthetic, modified mRNA described herein).

The present invention contemplates the use of any nucleic acid modification available to the skilled artisan. The nucleic acids of the present invention can include any number of modifications. In some embodiments, the nucleic acid comprises one or more modifications selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl)adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine, and combinations thereof.

Preparation of modified nucleosides and nucleotides used in the manufacture or synthesis of modified RNAs of the present invention can involve the protection and deprotection of various chemical groups. The need for protection and deprotection, and the selection of appropriate protecting groups can be readily determined by one skilled in the art.

The chemistry of protecting groups can be found, for example, in Greene, et al., Protective Groups in Organic Synthesis, 2d. Ed., Wiley & Sons, 1991, which is incorporated herein by reference in its entirety.

Modified nucleosides and nucleotides can be prepared according to the synthetic methods described in Ogata et al. Journal of Organic Chemistry 74:2585-2588, 2009; Purmal et al. Nucleic Acids Research 22(1): 72-78, 1994; Fukuhara et al. Biochemistry 1(4): 563-568, 1962; and Xu et al. Tetrahedron 48(9): 1729-1740, 1992, each of which are incorporated by reference in their entirety.

Modified nucleic acids (e.g., ribonucleic acids) need not be uniformly modified along the entire length of the molecule. Different nucleotide modifications and/or backbone structures may exist at various positions in the nucleic acid. One of ordinary skill in the art will appreciate that the nucleotide analogs or other modification(s) may be located at any position(s) of a nucleic acid such that the function of the nucleic acid is not substantially decreased. A modification may also be a 5' or 3' terminal modification. The nucleic acids may contain at a minimum one and at maximum 100% modified nucleotides, or any intervening percentage, such as at least 50% modified nucleotides, at least 80% modified nucleotides, or at least 90% modified nucleotides.

In some embodiments, at least one of the one to two ribonucleic acids is a modified ribonucleic acid. In some embodiments, each of the one to two ribonucleic acids is a modified ribonucleic acid. In some embodiments, at least one of the multiple ribonucleic acids is a modified ribonucleic acid. In some embodiments, a plurality of the multiple ribonucleic acids are modified. In some embodiments, each of the multiple ribonucleic acids are modified. Those skilled in the art will appreciate that the modified ribonucleic acids can include one or more of the nucleic acid modification described herein.

In some aspects, provided herein are synthetic, modified RNA molecules encoding polypeptides, where the synthetic, modified RNA molecules comprise one or more modifications, such that introducing the synthetic, modified RNA molecules to a cell results in a reduced innate immune response relative to a cell contacted with synthetic RNA molecules encoding the polypeptides not comprising the one or more modifications. In some embodiments, the Cas protein comprises a synthetic, modified RNA molecule encoding a Cas protein. In some embodiments, the Cas protein comprises a synthetic, modified RNA molecule encoding a Cas9 protein.

The synthetic, modified RNAs described herein include modifications to prevent rapid degradation by endo- and exo-nucleases and to avoid or reduce the cell's innate immune or interferon response to the RNA. Modifications include, but are not limited to, for example, (a) end modifications, e.g., 5' end modifications (phosphorylation dephosphorylation, conjugation, inverted linkages, etc.), 3' end modifications (conjugation, DNA nucleotides, inverted linkages, etc.), (b) base modifications, e.g., replacement with modified bases, stabilizing bases, destabilizing bases, or bases that base pair with an expanded repertoire of partners, or conjugated bases, (c) sugar modifications (e.g., at the 2' position or 4' position) or replacement of the sugar, as well as (d) internucleoside linkage modifications, including modification or replacement of the phosphodiester linkages. To the extent that such modifications interfere with translation (i.e., results in a reduction of 50% or more in translation relative to the lack of the modification—e.g., in a rabbit reticulocyte in vitro translation assay), the modification is not suitable for the methods and compositions described herein. Specific examples of synthetic, modified RNA compositions useful with the methods described herein include, but are not limited to, RNA molecules containing modified or non-natural internucleoside linkages. Synthetic, modified RNAs having modified internucleoside linkages include, among others, those that do not have a phosphorus atom in the internucleoside linkage. In other embodiments, the synthetic, modified RNA has a phosphorus atom in its internucleoside linkage(s).

Non-limiting examples of modified internucleoside linkages include phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference in its entirety.

Modified internucleoside linkages that do not include a phosphorus atom therein have internucleoside linkages that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of modified oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and 5,677,439, each of which is herein incorporated by reference in its entirety.

Some embodiments of the synthetic, modified RNAs described herein include nucleic acids with phosphorothioate internucleoside linkages and oligonucleosides with heteroatom internucleoside linkage, and in particular —$CH_2$—NH—$CH_2$-, —$CH_2$-N($CH_3$)-O—$CH_2$-[known as a methylene(methylimino) or MMI], —$CH_2$-O—N($CH_3$)-$CH_2$-, —$CH_2$-N($CH_3$)-N($CH_3$)-$CH_2$- and —N($CH_3$)-$CH_2$-$CH_2$- [wherein the native phosphodiester internucleoside linkage is represented as —O—P—O—$CH_2$-] of the above-referenced U.S. Pat. No. 5,489,677, and the amide backbones of the above-referenced U.S. Pat. No. 5,602,240, both of which are herein incorporated by reference in their entirety. In some embodiments, the nucleic acid sequences featured herein have morpholino backbone structures of the above-referenced U.S. Pat. No. 5,034,506, herein incorporated by reference in its entirety.

Synthetic, modified RNAs described herein can also contain one or more substituted sugar moieties. The nucleic acids featured herein can include one of the following at the 2' position: H (deoxyribose); OH (ribose); F; O—, S—, or N-alkyl; O—, S—, or N-alkenyl; O—, S- or N-alkynyl; or O-alkyl-O-alkyl, wherein the alkyl, alkenyl and alkynyl can be substituted or unsubstituted C1 to C10 alkyl or C2 to C10 alkenyl and alkynyl. Exemplary modifications include O[($CH_2$)nO]m$CH_3$, O($CH_2$).nO$CH_3$, O($CH_2$)nNH$_2$, O($CH_2$)n$CH_3$, O($CH_2$)nON$H_2$, and O($CH_2$)nON[($CH_2$)n$CH_3$)]$_2$, where n and m are from 1 to about 10. In some embodiments, synthetic, modified RNAs include one of the following at the 2' position: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, a reporter group, an intercalator, a group for improving the pharmacokinetic properties of an RNA, or a group for improving the pharmacodynamic properties of a synthetic, modified RNA, and other substituents having similar properties. In some embodiments, the modification includes a 2' methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O($CH_2$)2ON($CH_3$)2 group, also known as 2'-DMAOE, and 2'-dimethylaminoethoxyethoxy (also known in the art as 2'-O-dimethylaminoethoxyethyl or 2'-DMAEOE), i.e., 2'-O—$CH_2$-O—$CH_2$-N($CH_2$)2.

Other modifications include 2'-methoxy (2'-OCH3), 2'-aminopropoxy (2'-OCH2CH2CH2NH2) and 2'-fluoro (2'-F). Similar modifications can also be made at other positions on the nucleic acid sequence, particularly the 3' position of the sugar on the 3' terminal nucleotide or in 2'-5' linked nucleotides and the 5' position of 5' terminal nucleotide. A synthetic, modified RNA can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

As non-limiting examples, synthetic, modified RNAs described herein can include at least one modified nucleoside including a 2'-O-methyl modified nucleoside, a nucleoside comprising a 5' phosphorothioate group, a 2'-amino-modified nucleoside, 2'-alkyl-modified nucleoside, morpholino nucleoside, a phosphoramidate or a non-natural base comprising nucleoside, or any combination thereof.

In some embodiments of this aspect and all other such aspects described herein, the at least one modified nucleoside is selected from the group consisting of 5-methylcytidine (5mC), N6-methyladenosine (m6A), 3,2'-O-dimethyluridine (m4U), 2-thiouridine (s2U), 2' fluorouridine, pseudouridine, 2'-O-methyluridine (Um), 2' deoxyuridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I).

Alternatively, a synthetic, modified RNA can comprise at least two modified nucleosides, at least 3, at least 4, at least 5, at least 6, at least 7, at least 8, at least 9, at least 10, at least 15, at least 20 or more, up to the entire length of the nucleotide. At a minimum, a synthetic, modified RNA molecule comprising at least one modified nucleoside comprises a single nucleoside with a modification as described herein. It is not necessary for all positions in a given synthetic, modified RNA to be uniformly modified, and in fact more than one of the aforementioned modifications can be incorporated in a single synthetic, modified RNA or even at a single nucleoside within a synthetic, modified RNA. However, it is preferred, but not absolutely necessary, that each occurrence of a given nucleoside in a molecule is modified (e.g., each cytosine is a modified cytosine e.g., 5mC). However, it is also contemplated that different occurrences of the same nucleoside can be modified in a different way in a given synthetic, modified RNA molecule (e.g., some cytosines modified as 5mC, others modified as 2'-O-methylcytidine or other cytosine analog). The modifications need not be the same for each of a plurality of modified nucleosides in a synthetic, modified RNA. Furthermore, in some embodiments of the aspects described herein, a synthetic, modified RNA comprises at least two different modified nucleosides. In some such preferred embodiments of the aspects described herein, the at least two different modified nucleosides are 5-methylcytidine and pseudouridine. A synthetic, modified RNA can also contain a mixture of both modified and unmodified nucleosides.

As used herein, "unmodified" or "natural" nucleosides or nucleobases include the purine bases adenine (A) and guanine (G), and the pyrimidine bases thymine (T), cytosine (C) and uracil (U). In some embodiments, a synthetic, modified RNA comprises at least one nucleoside ("base") modification or substitution. Modified nucleosides include other synthetic and natural nucleobases such as inosine, xanthine, hypoxanthine, nubularine, isoguanisine, tubercidine, 2-(halo)adenine, 2-(alkyl)adenine, 2-(propyl)adenine, 2 (amino)adenine, 2-(aminoalkyl)adenine, 2 (aminopropyl) adenine, 2 (methylthio) N6 (isopentenyl)adenine, 6 (alkyl) adenine, 6 (methyl)adenine, 7 (deaza)adenine, 8 (alkenyl) adenine, 8-(alkyl)adenine, 8 (alkynyl)adenine, 8 (amino) adenine, 8-(halo)adenine, 8-(hydroxyl)adenine, 8 (thioalkyl) adenine, 8-(thiol)adenine, N6-(isopentyl)adenine, N6 (methyl)adenine, N6,N6 (dimethyl)adenine, 2-(alkyl)guanine, 2 (propyl)guanine, 6-(alkyl)guanine, 6 (methyl)guanine, 7 (alkyl)guanine, 7 (methyl)guanine, 7 (deaza)guanine, 8 (alkyl)guanine, 8-(alkenyl)guanine, 8 (alkynyl)guanine, 8-(amino)guanine, 8 (halo)guanine, 8-(hydroxyl)guanine, 8 (thioalkyl)guanine, 8-(thiol)guanine, N(methyl)guanine, 2-(thio)cytosine, 3 (deaza) 5 (aza)cytosine, 3-(alkyl)cytosine, 3 (methyl)cytosine, 5-(alkyl)cytosine, 5-(alkynyl)cytosine, 5 (halo)cytosine, 5 (methyl)cytosine, 5 (propynyl) cytosine, 5 (propynyl)cytosine, 5 (trifluoromethyl)cytosine, 6-(azo)cytosine, N4 (acetyl)cytosine, 3 (3 amino-3 carboxypropyl)uracil, 2-(thio)uracil, 5 (methyl) 2 (thio)uracil, 5 (methylaminomethyl)-2 (thio)uracil, 4-(thio)uracil, 5 (methyl) 4 (thio)uracil, 5 (methylaminomethyl)-4 (thio)uracil, 5 (methyl) 2,4 (dithio)uracil, 5 (methylaminomethyl)-2,4 (dithio)uracil, 5 (2-aminopropyl)uracil, 5-(alkyl)uracil, 5-(alkynyl)uracil, 5-(allylamino)uracil, 5 (aminoallyl)uracil, 5 (aminoalkyl)uracil, 5 (guanidiniumalkyl)uracil, 5 (1,3-diazole-1-alkyl)uracil, 5-(cyanoalkyl)uracil, 5-(dialkylaminoalkyl)uracil, 5 (dimethylaminoalkyl)uracil, 5-(halo)uracil, 5-(methoxy)uracil, uracil-5 oxyacetic acid, 5 (methoxycarbonylmethyl)-2-(thio)uracil, 5 (methoxycarbonyl-methyl)uracil, 5 (propynyl)uracil, 5 (propynyl)uracil, 5 (trifluoromethyl)uracil, 6 (azo)uracil, dihydrouracil, N3 (methyl)uracil, 5-uracil (i.e., pseudouracil), 2 (thio)pseudouracil, 4 (thio)pseudouracil, 2,4-(dithio)psuedouracil, 5-(alkyl)pseudouracil, 5-(methyl)pseudouracil, 5-(alkyl)-2-(thio)pseudouracil, 5-(methyl)-2-(thio)pseudouracil, 5-(alkyl)-4 (thio)pseudouracil, 5-(methyl)-4 (thio)pseudouracil, 5-(alkyl)-2,4 (dithio)pseudouracil, 5-(methyl)-2,4 (dithio)pseudouracil, 1 substituted pseudouracil, 1 substituted 2(thio)-pseudouracil, 1 substituted 4 (thio)pseudouracil, 1 substituted 2,4-(dithio)pseudouracil, 1 (aminocarbonylethylenyl)-pseudouracil, 1 (aminocarbonylethylenyl)-2(thio)-pseudouracil, 1 (aminocarbonylethylenyl)-4 (thio)pseudouracil, 1 (aminocarbonylethylenyl)-2,4-(dithio)pseudouracil, 1 (aminoalkylaminocarbonylethylenyl)-pseudouracil, 1 (aminoalkylaminocarbonylethylenyl)-2(thio)-pseudouracil, 1 (aminoalkylaminocarbonylethylenyl)-4 (thio)pseudouracil, 1 (aminoalkylaminocarbonylethylenyl)-2,4-(dithio) pseudouracil, 1,3-(diaza)-2-(oxo)-phenoxazin-1-yl, 1-(aza)-2-(thio)-3-(aza)-phenoxazin-1-yl, 1,3-(diaza)-2-(oxo)-phenthiazin-1-yl, 1-(aza)-2-(thio)-3-(aza)-phenthiazin-1-yl, 7-substituted 1,3-(diaza)-2-(oxo)-phenoxazin-1-yl, 7-substituted 1-(aza)-2-(thio)-3-(aza)-phenoxazin-1-yl, 7-substituted 1,3-(diaza)-2-(oxo)-phenthiazin-1-yl, 7-substituted 1-(aza)-2-(thio)-3-(aza)-phenthiazin-1-yl, 7-(aminoalkylhydroxy)-1,3-(diaza)-2-(oxo)-phenoxazin-1-yl, 7-(aminoalkylhydroxy)-1-(aza)-2-(thio)-3-(aza)-phenoxazin-1-yl, 7-(aminoalkylhydroxy)-1,3-(diaza)-2-(oxo)-phenthiazin-1-yl, 7-(aminoalkylhydroxy)-1-(aza)-2-(thio)-3-(aza)-phenthiazin-1-yl, 7-(guanidiniumalkylhydroxy)-1,3-(diaza)-2-(oxo)-phenoxazin-1-yl, 7-(guanidiniumalkylhydroxy)-1-(aza)-2-(thio)-3-(aza)-phenoxazin-1-yl, 7-(guanidiniumalkylhydroxy)-1,3-(diaza)-2-(oxo)-phenthiazin-1-yl, 7-(guanidiniumalkylhydroxy)-1-(aza)-2-(thio)-3-(aza)-phenthiazin-1-yl, 1,3,5-(triaza)-2,6-(dioxa)-naphthalene, inosine, xanthine, hypoxanthine, nubularine, tubercidine, isoguanisine, inosinyl, 2-aza-inosinyl, 7-deaza-inosinyl, nitroimidazolyl, nitropyrazolyl, nitrobenzimidazolyl, nitroindazolyl, aminoindolyl, pyrrolopyrimidinyl, 3-(methyl)isocarbostyrilyl, 5-(methyl)isocarbostyrilyl, 3-(methyl)-7-(propynyl)isocarbostyrilyl, 7-(aza)indolyl, 6-(methyl)-7-(aza)indolyl, imidizopyridinyl, 9-(methyl)-imidizopyridinyl, pyrrolopyrizinyl, isocarbostyrilyl, 7-(propynyl)isocarbostyrilyl, propynyl-7-(aza)indolyl, 2,4,5-(trimethyl)phenyl, 4-(methyl)indolyl, 4,6-(dimethyl)indolyl, phenyl, napthalenyl, anthracenyl, phenanthracenyl, pyrenyl, stilbenzyl, tetracenyl, pentacenyl, difluorotolyl, 4-(fluoro)-6-(methyl)benzimidazole, 4-(methyl)benzimidazole, 6-(azo) thymine, 2-pyridinone, 5 nitroindole, 3 nitropyrrole, 6-(aza) pyrimidine, 2 (amino)purine, 2,6-(diamino)purine, 5 substituted pyrimidines, N2-substituted purines, N6-substituted purines, 06-substituted purines, substituted 1,2,4-triazoles, pyrrolo-pyrimidin-2-on-3-yl, 6-phenyl-pyrrolo-pyrimidin-2-on-3-yl, para-substituted-6-phenyl-pyrrolo-pyrimidin-2-on-3-yl, ortho-substituted-6-phenyl-pyrrolo-pyrimidin-2-on-3-yl, bis-ortho-substituted-6-phenyl-pyrrolo-pyrimidin-2-on-3-yl, para-(aminoalkylhydroxy)-6-phenyl-pyrrolo-pyrimidin-2-on-3-yl, ortho-(aminoalkylhydroxy)-6-phenyl-pyrrolo-pyrimidin-2-on-3-yl, bis-ortho-(aminoalkylhydroxy)-6-phenyl-pyrrolo-pyrimidin-2-on-3-yl, pyridopyrimidin-3-yl, 2-oxo-7-amino-pyridopyrimidin-3-yl, 2-oxo-pyridopyrimidine-3-yl, or any O-alkylated or N-alkylated derivatives thereof. Modified nucleosides also include natural bases that comprise conjugated moieties, e.g. a ligand. As discussed herein above, the RNA containing the modified nucleosides must be translatable in a host cell (i.e., does not prevent translation of the polypeptide encoded by the modified RNA). For example, transcripts containing s2U and m6A are translated poorly in rabbit reticulocyte lysates, while pseudouridine, m5U, and m5C are compatible with efficient translation. In addition, it is known in the art that 2'-fluoro-modified bases useful for increasing nuclease resistance of a transcript, leads to very inefficient translation. Translation can be assayed by one of ordinary skill in the art using e.g., a rabbit reticulocyte lysate translation assay.

Further modified nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in Int. Appl. No. PCT/US09/038,425, filed Mar. 26, 2009; those disclosed in The Concise Encyclopedia Of Polymer Science And Engineering, pages 858-859, Kroschwitz, J. L, ed. John Wiley & Sons, 1990, and those disclosed by Englisch et al., Angewandte Chemie, International Edition, 1991, 30, 613.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference in its entirety, and U.S. Pat. No. 5,750,692, also herein incorporated by reference in its entirety.

Another modification for use with the synthetic, modified RNAs described herein involves chemically linking to the RNA one or more ligands, moieties or conjugates that enhance the activity, cellular distribution or cellular uptake of the RNA. The synthetic, modified RNAs described herein can further comprise a 5' cap. In some embodiments of the aspects described herein, the synthetic, modified RNAs comprise a 5' cap comprising a modified guanine nucleotide that is linked to the 5' end of an RNA molecule using a 5'-5' triphosphate linkage. As used herein, the term "5' cap" is also intended to encompass other 5' cap analogs including, e.g., 5' diguanosine cap, tetraphosphate cap analogs having a methylene-bis(phosphonate) moiety (see e.g., Rydzik, A M et al., (2009) Org Biomol Chem 7(22):4763-76), dinucleotide cap analogs having a phosphorothioate modification (see e.g., Kowalska, J. et al., (2008) RNA 14(6):1119-1131), cap analogs having a sulfur substitution for a non-bridging oxygen (see e.g., Grudzien-Nogalska, E. et al., (2007) RNA 13(10): 1745-1755), N7-benzylated dinucleoside tetraphosphate analogs (see e.g., Grudzien, E. et al., (2004) RNA 10(9):1479-1487), or anti-reverse cap analogs (see e.g., Jemielity, J. et al., (2003) RNA 9(9): 1108-1122 and Stepinski, J. et al., (2001) RNA 7(10):1486-1495). In one such embodiment, the 5' cap analog is a 5' diguanosine cap. In some embodiments, the synthetic, modified RNA does not comprise a 5' triphosphate.

The 5' cap is important for recognition and attachment of an mRNA to a ribosome to initiate translation. The 5' cap also protects the synthetic, modified RNA from 5' exonuclease mediated degradation. It is not an absolute requirement that a synthetic, modified RNA comprise a 5' cap, and thus in other embodiments the synthetic, modified RNAs lack a 5' cap. However, due to the longer half-life of synthetic, modified RNAs comprising a 5' cap and the increased efficiency of translation, synthetic, modified RNAs comprising a 5' cap are preferred herein.

The synthetic, modified RNAs described herein can further comprise a 5' and/or 3' untranslated region (UTR). Untranslated regions are regions of the RNA before the start codon (5') and after the stop codon (3'), and are therefore not translated by the translation machinery. Modification of an RNA molecule with one or more untranslated regions can improve the stability of an mRNA, since the untranslated regions can interfere with ribonucleases and other proteins involved in RNA degradation. In addition, modification of an RNA with a 5' and/or 3' untranslated region can enhance translational efficiency by binding proteins that alter ribosome binding to an mRNA. Modification of an RNA with a 3' UTR can be used to maintain a cytoplasmic localization of the RNA, permitting translation to occur in the cytoplasm of the cell. In one embodiment, the synthetic, modified RNAs described herein do not comprise a 5' or 3' UTR. In another embodiment, the synthetic, modified RNAs comprise either a 5' or 3' UTR. In another embodiment, the synthetic, modified RNAs described herein comprise both a 5' and a 3' UTR. In one embodiment, the 5' and/or 3' UTR is selected from an mRNA known to have high stability in the cell (e.g., a murine alpha-globin 3' UTR). In some embodiments, the 5' UTR, the 3' UTR, or both comprise one or more modified nucleosides.

In some embodiments, the synthetic, modified RNAs described herein further comprise a Kozak sequence. The "Kozak sequence" refers to a sequence on eukaryotic mRNA having the consensus (gcc)gccRccAUGG, where R is a purine (adenine or guanine) three bases upstream of the start codon (AUG), which is followed by another 'G'. The Kozak consensus sequence is recognized by the ribosome to initiate translation of a polypeptide. Typically, initiation occurs at the first AUG codon encountered by the translation machinery that is proximal to the 5' end of the transcript. However, in some cases, this AUG codon can be bypassed in a process called leaky scanning. The presence of a Kozak sequence near the AUG codon will strengthen that codon as the initiating site of translation, such that translation of the correct polypeptide occurs. Furthermore, addition of a Kozak sequence to a synthetic, modified RNA will promote more efficient translation, even if there is no ambiguity regarding the start codon. Thus, in some embodiments, the synthetic, modified RNAs described herein further comprise a Kozak consensus sequence at the desired site for initiation of translation to produce the correct length polypeptide. In some such embodiments, the Kozak sequence comprises one or more modified nucleosides.

In some embodiments, the synthetic, modified RNAs described herein further comprise a "poly (A) tail", which refers to a 3' homopolymeric tail of adenine nucleotides, which can vary in length (e.g., at least 5 adenine nucleotides) and can be up to several hundred adenine nucleotides). The inclusion of a 3' poly(A) tail can protect the synthetic, modified RNA from degradation in the cell, and also facilitates extra-nuclear localization to enhance translation efficiency. In some embodiments, the poly(A) tail comprises between 1 and 500 adenine nucleotides; in other embodiments the poly(A) tail comprises at least 5, at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 225, at least 250, at least 275, at least 300, at least 325, at least 350, at least 375, at least 400, at least 425, at least 450, at least 475, at least 500 adenine nucleotides or more. In one embodiment, the poly(A) tail comprises between 1 and 150 adenine nucleotides. In another embodiment, the poly(A) tail comprises between 90 and 120 adenine nucleotides. In some such embodiments, the poly(A) tail comprises one or more modified nucleosides.

It is contemplated that one or more modifications to the synthetic, modified RNAs described herein permit greater stability of the synthetic, modified RNA in a cell. To the extent that such modifications permit translation and either reduce or do not exacerbate a cell's innate immune or interferon response to the synthetic, modified RNA with the modification, such modifications are specifically contemplated for use herein. Generally, the greater the stability of a synthetic, modified RNA, the more protein can be produced from that synthetic, modified RNA. Typically, the presence of AU-rich regions in mammalian mRNAs tend to destabilize transcripts, as cellular proteins are recruited to AU-rich regions to stimulate removal of the poly(A) tail of the transcript. Loss of a poly(A) tail of a synthetic, modified RNA can result in increased RNA degradation. Thus, in one embodiment, a synthetic, modified RNA as described herein does not comprise an AU-rich region. In particular, it is preferred that the 3' UTR substantially lacks AUUUA sequence elements.

In one embodiment, a ligand alters the cellular uptake, intracellular targeting or half-life of a synthetic, modified RNA into which it is incorporated. In some embodiments a ligand provides an enhanced affinity for a selected target, e.g., molecule, cell or cell type, intracellular compartment, e.g., mitochondria, cytoplasm, peroxisome, lysosome, as, e.g., compared to a composition absent such a ligand. Preferred ligands do not interfere with expression of a polypeptide from the synthetic, modified RNA.

The ligand can be a substance, e.g., a drug, which can increase the uptake of the synthetic, modified RNA or a composition thereof into the cell, for example, by disrupting the cell's cytoskeleton, e.g., by disrupting the cell's microtubules, microfilaments, and/or intermediate filaments. The drug can be, for example, taxol, vincristine, vinblastine, cytochalasin, nocodazole, japlakinolide, latrunculin A, phalloidin, swinholide A, indanocine, or myoservin.

In another aspect, the ligand is a moiety, e.g., a vitamin, which is taken up by a host cell. Exemplary vitamins include vitamin A, E, and K. Other exemplary vitamins include B vitamin, e.g., folic acid, B12, riboflavin, biotin, pyridoxal or other vitamins or nutrients taken up, for example, by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

The synthetic, modified RNAs described herein can be synthesized and/or modified by methods well established in the art, such as those described in "Current Protocols in Nucleic Acid Chemistry," Beaucage, S. L. et al. (Edrs.), John Wiley & Sons, Inc., New York, N.Y., USA, which is hereby incorporated herein by reference in its entirety. Transcription methods are described further herein in the Examples.

In one embodiment of the aspects described herein, a template for a synthetic, modified RNA is synthesized using "splint-mediated ligation," which allows for the rapid synthesis of DNA constructs by controlled concatenation of long oligos and/or dsDNA PCR products and without the need to introduce restriction sites at the joining regions. It can be used to add generic untranslated regions (UTRs) to the coding sequences of genes during T7 template generation. Splint mediated ligation can also be used to add nuclear localization sequences to an open reading frame, and to make dominant-negative constructs with point mutations starting from a wild-type open reading frame. Briefly, single-stranded and/or denatured dsDNA components are annealed to splint oligos which bring the desired ends into conjunction, the ends are ligated by a thermostable DNA ligase and the desired constructs amplified by PCR. A synthetic, modified RNA is then synthesized from the template using an RNA polymerase in vitro. After synthesis of a synthetic, modified RNA is complete, the DNA template is removed from the transcription reaction prior to use with the methods described herein.

In some embodiments of these aspects, the synthetic, modified RNAs are further treated with an alkaline phosphatase.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

As used herein "A and/or B", where A and B are different claim terms, generally means at least one of A, B, or both A and B. For example, one sequence which is complementary to and/or hybridizes to another sequence includes (i) one sequence which is complementary to the other sequence even though the one sequence may not necessarily hybridize to the other sequence under all conditions, (ii) one sequence which hybridizes to the other sequence even if the one sequence is not perfectly complementary to the other sequence, and (iii) sequences which are both complementary to and hybridize to the other sequence.

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

EXAMPLES

Example 1

Transcription activator-like effector nucleases (TALENs) bind as a pair around a genomic site, in which a double-strand break (DSB) is introduced by a dimer of FokI nuclease domains. The use of a TALEN genome-editing system to rapidly and efficiently generate mutant alleles of 15 different genes in human pluripotent stem cells (hPSCs) as a means of performing rigorous disease modeling was recently reported (Ding et al., Cell Stem Cell 12:238-251 (2013)); the proportions of clones bearing at least one mutant allele ranged from 2%-34%.

As described below, the relative efficacies of CRISPRs and TALENs targeting the same genomic sites in the same hPSC lines was assessed with the use of the same delivery platform described previously (Ding et al., Cell Stem Cell 12:238-251 (2013)). In the TALEN genome-editing system, the CAG promoter was used to co-translate (via a viral 2A peptide) each TALEN with green fluorescent protein (GFP) or red fluorescent protein (RFP). For CRISPRs, a human codon-optimized Cas9 gene was subcloned with a C-terminal nuclear localization signal (Mali et al., Science 339:823-826 (2013)) into the same CAG expression plasmid with GFP, and the guide RNA (gRNA) was separately expressed from a plasmid with the human U6 polymerase III promoter (Mali et al., Science 339:823-826 (2013)). The 20-nucleotide protospacer sequence for each gRNA was introduced using polymerase chain reaction (PCR)-based methods. Whether using TALENs or CRISPRs, equal amounts of the two plasmids were co-electroporated into hPSCs (either 25 μg of each plasmid, or 12.5 μg of each plasmid along with 25 μg of a DNA repair template if attempting knock-in) followed by fluorescence-activated cell sorting (FACS) after 24-48 hours, clonal expansion of single cells, and screening for mutations at the genomic target site via PCR.

gRNAs were designed matching G(N)19NGG sequences in seven loci in six genes (AKT2, CELSR2, CIITA, GLUT4, LINC00116, and SORT1) previously successfully targeted with TALENs (Ding et al., Cell Stem Cell 12:238-251 (2013)) and one additional locus in LDLR. In this system, CRISPRs consistently and substantially outperformed TALENs across loci and hPSC lines (see Table S1). The TALENs yielded clones with at least one mutant allele at efficiencies of 0%-34%, but matched CRISPRs yielded mutant clones at efficiencies of 51%-79% (Table S1). Just as with TALENs, CRISPRs produced a variety of indels of sizes ranging from one nucleotide to several dozen nucleotides in size, centered on the predicted cleavage sites, suggesting that non-homologous end-joining mutagenesis occurs in the same way regardless of whether CRISPRs or TALENs are used. Moreover, CRISPRs readily generated homozygous mutant clones (7%-25% of all clones; Table S1) as discerned by sequencing.

Knock-in of E17K mutations into AKT2 was also attempted using a 67-nucleotide single-stranded DNA oligonucleotide as previously described (Ding et al., Cell Stem Cell 12:238-251 (2013)). Although the predicted CRISPR cleavage site lay 11 and 13 nucleotides from the point mutations, respectively, the CRISPR yielded knock-in clones at a rate of 11%, whereas TALENs yielded only 1.6% (Table S1).

TABLE S1

Targeting Efficiency of CRISPRs Versus TALENs in Human Pluripotent Stem Cells

| Gene | Chromosome: Position (Start of Target Sequence) | Target Sequence[a] | Cell Line[b] | TALENs Efficiency (Mutants/Clones Screened)[c] | CRISPRs Efficiency (Mutants/Clones Screened)[c] | Efficiency of Homozygous Mutants |
|---|---|---|---|---|---|---|
| AKT2 | chr19:40762982 | TCCCTTCCTGCCTCATTTCAGGTGAATAC ATCAAGACCTGGAGGCCA | HUES 9 | 8.9% (17/192) | (SEQ ID NO: 335) | |
| AKT2 | chr19:40762982 | TCCCTTCCTGCC\|TCATTTCAGGTGAATA CATCAAGACCTGGAGGCCA | HUES 9 | (SEQ ID NO: 336) | 60.6% (86/142) | 12.7% (18/142) |
| CELSR2 | chr1:109817568 | TGCTGGCTCGGCTGCCCTGAGGTTGCTCA ATCAAGCACAGGTTTCAA | HUES 1 | 3.5% (18/506) | (SEQ ID NO: 337) | |
| CELSR2 | chr1:109817568 | TGCTGGCTCGGCTGCCCTGAGGTTGCTCA ATCAAG\|CACAGGTTTCAA | HUES 1 | (SEQ ID NO: 338) | 66.2% (45/68) | 7.4% (5/68) |
| CIITA | chr18:10989200 | TAACAGCGATGCTGACCCCTGTGCCTCT ACCACTTCTATGACCAGA | BJ-RiPS | 12.7% (37/292) | (SEQ ID NO: 339) | |
| CIITA | chr16:10989206 | CGATGCTGACCCCTGTGCCTCTACCACT T\|CTATGACCAGATGGACC | BJ-RiPS | (SEQ ID NO: 340) | 78.7% (96/122) | 11.5% (14/122) |
| GLUT4 | chr17:7186601 | TGGTCCTTGCTGTGTTCTCTGCGGTGCTT GGCTCCCTGCAGTTTGGGTA | HUES 9 | 33.5% (52/155) | (SEQ ID NO: 341) | |
| GLUT4 | chr17:7186601 | TGGTCCTTGCTGTGTTCT\|CTGCGGTGCT TGGCTCCCTGCAGTTTGGGTA | HUES 9 | (SEQ ID NO: 342) | 66.5% (123/185) | 24.9% (46/185) |

TABLE S1-continued

Targeting Efficiency of CRISPRs Versus TALENs in Human Pluripotent Stem Cells

| Gene | Chromosome: Position (Start of Target Sequence) | Target Sequence[a] | Cell Line[b] | TALENs Efficiency (Mutants/Clones Screened)[c] | CRISPRs Efficiency (Mutants/Clones Screened)[c] | Efficiency of Homozygous Mutants |
|---|---|---|---|---|---|---|
| LDLR | chr19:11210899 | TGGGCGACAGATGCGAAAGAAACGAGTTC CAGTGCCAAGACGGGAAA | HUES 9 | 0% (0/568) | (SEQ ID NO: 343) | |
| LDLR | chr19:11210917 | GAAACGAGTTCCAGTGCCAAGACGGGAAA TGCATCTCCTAC\|AAGTGG | HUES 9 | (SEQ ID NO: 344) | 51.1% (90/176) | 8.0% (14/176) |
| LINC00116 | chr2:110970090 | TCAGAGAGGACACTGCAGTTGTCCGTGCT AGTAGCCTTCGCTTCTGGA | HUES 9 | 29.5% (26/88) | (SEQ ID NO: 145) | |
| LINC00116 | chr2:110970090 | TCAGAGAGGACACTGCAGTTGTCCGTGCTA GTAGCCTTCGC\|TTCTGGA | HUES 9 | (SEQ ID NO: 346) | 57.4% (93/162) | 8.6% (14/162) |
| SORT1 exon 2 | chr1:109912203 | TGATGATCTCAGAGGCTCAGTATCCTTGTC CTGGGTTGGAGATAGCA | HUES 1 | 22.2% (128/576) | (SEQ ID NO: 347) | |
| SORT1 exon 2 | chr1:109912203 | TGATGATCTCAGAGGCTCAGTATCCTTG\|T CCTGGGTTGGAGATAGCA | HUES 1 | (SEQ ID NO: 348) | 68.5% (100/146) | 13.0% (19/146) |
| SORT1 exon 3 | chr1:109910069 | TGGTAATTATGACTTTTGGACAGTCCAAGC TATATCGAAGGTGAGATCA | HUES 9 | 10.9% (21/192) | (SEQ ID NO: 349) | |
| SORT1 exon 3 | chr1:109910069 | TGGTAATTATGACTTTTGGACAGTCCAAGC TATAT\|CGAAGGTGAGATCA | HUES 9 | (SEQ ID NO: 350) | 75.9% (148/195) | 10.3% (20/195) |
| AKT2E17K | chr19:40762982 | TCCCTTCCTGCCTCATTTCAGGGA*A*TA CATCAAGACCTGGAGGCCA | HUES 9 | 1.6% (3/192)[d] | (SEQ ID NO: 351) | |
| AKT2E17K | chr19:40762982 | TCCCTTCCT GCC\|TCATTTCAGGTGAATAC ATCAAGACCTGGAGGCCA | HUES 9 | (SEQ ID NO: 352) | 10.6% (10/94)[d] | 1.1% (1/94)[d] |
| AKT2 off-target | chr5:22683972 | CTATGCCCTGCC\|TCATTTCAGGTGAA*G* A*T*GAAATCCTGGAGCTTGG | HUES 9 | (SEQ ID NO: 353) | 0% (0/142) | 0% (0/142) |

[a]For TALENs, the binding sites are indicated with underlines; with the cleavage site predicted to be midway between the binding sites; for CRISPRs, the protospacer is underlined, the NGG motif is in bold (may be on the antisense strand), and the predicted cleavage site is indicated with "|"; for the AKT2 E17K target sequence, the sites of the knock-in mutations are indicated in bold/italics; for the AKT2 off-target site, the two mismatches in the protospacer are indicated in bold/italics
[b]HUES 1 and HUES 9 are human embryonic stem cell lnes; BJ-RiPS is an induced pluripotent stem cell line
[c]Mutants include single heterozygotes, compound heterozygotes, and homozygous mutants: TALEN data is from Table 1 of Ding et al, (2013), with the exception of LDLR
[d]Successfully inserted E17K knock-in mutations into an AKT2 allele(s) using single-stranded DNA oligonucleotide (refer to FIG. 3 of Ding et al., 2013)

It is worth noting that the requirement for a G(N)19NGG target sequence somewhat limits site selection. Because either DNA strand can be targeted, a target sequence occurs on average every 32 basepairs. This is no barrier for gene knockout, where any coding sequence can be targeted, but it may present difficulties when trying to knock in or correct a mutation at a specific location. However, the requirement for a G at the start of the protospacer is dictated by the use of the U6 promoter to express the gRNA, and alternative CRISPR/Cas systems can relieve this requirement (Cong et al., Science 339:819-823 (2013)). This allows for the use of (N)20NGG target sequences, which are found on average every 8 basepairs.

In addition, the extent of CRISPR off-target effects remains to be defined and is highly sequence-dependent. Previous analyses have suggested that one-nucleotide mismatches in the first half of the protospacer are better tolerated than mismatches in second half (Jinek et al., Science 337:816-821 (2012); Cong et al., Science 339:819-823 (2013)). For the AKT2 sequence, there is a two-mismatch sequence differing at nucleotides 1 and 3, in the more "tolerant" half of the protospacer. Zero clones were obtained with mutations at this potential off-target site, as compared to 61% at the on-target site (Table Sp. For one of the SORT1 sequences, use of a different human pluripotent stem cell line in which a single nucleotide polymorphism results in a one-nucleotide mismatch at the target site yielded mutant clones at an efficiency of 42%, compared to 66% in the original cell line. Thus, judicious selection of target sites is necessary to minimize systematic off-target effects; target sites with perfect-match or single-nucleotide-mismatch sequences elsewhere in the genome should be avoided.

From a practical standpoint, CRISPRs are easier to implement than TALENS. Each TALEN pair must be constructed de novo, whereas for CRISPRs the Cas9 component is fixed and the gRNA requires only swapping of the 20-nucleotide protospacer. Given this consideration and the demonstration herein of substantially increased efficiency as a result of replacing TALENs with CRISPRs in an otherwise identical system, CRISPRs appear to be a very powerful and broadly applicable tool for genome editing, particularly in a therapeutic context.

Example 2

Efficient Targeting of Clinically Relevant Genes in Primary Somatic Cells

Work described herein shows for the first time that the CRISPR/Cas9 system can be used to edit the genome of somatic cells (e.g., primary) with high efficiency by using a double guide strategy. The inventors posit that this work will help bring genome editing in clinically relevant primary cells into reality.

The advent of genome editing tools that allow one to target any desired genomic site has greatly advanced the investigation of human biology and disease. In particular, the CRISPR/Cas9 system has become the gold standard in targeted genome editing technology, due to its flexibility and high efficacy. This system is constituted by the Cas9 nuclease from the microbial type II CRISPR/Cas system, which is targeted to specific genomic loci by a 20-nucleotide region in a synthetic guide RNA molecule. Similar to other targeted nucleases (ZFNs and TALENs), Cas9 induces double strand breaks (DSBs) that are repaired mainly by error-prone non-homologous end joining (NHEJ) (Cong et al., 2013; Jinek et al., 2013; Mali et al., 2013).

Implementation of the CRISPR/Cas9 system has made it possible to achieve unprecedentedly high targeting efficiencies in immortalized cell lines (Cong et al., 2013; Jinek et al., 2013; Mali et al., 2013), human pluripotent stem cells (Ding et al., 2013) and even zygotes of mice (Wang et al., 2013), rats (Li et al., 2013) and, most recently, monkeys (Niu et al., 2014), leading to the generation of knock-out or knock-in animals in very short periods of time when compared to classical strategies.

However, it remains to be proven whether CRISPR/Cas9 technology can be used to edit the genome of clinically relevant primary somatic cells with high efficiency, an essential step for the full realization of the promise of genome editing for regenerative medicine and transplantation therapies.

The inventors sought to test the amenability of the CRISPR/Cas9 system to edit clinically relevant genes in primary somatic cells. For this purpose the inventors chose to target two therapy-related genes: CCR5, a co-receptor for HIV, in CD34+ hematopoietic progenitor cells (HPCs), and B2M, the accessory chain of MHC class I molecules, in CD4+ T cells. The inventors found that a single guide strategy yielded very low to undetectable mutational rates in HPCs and T cells, despite high efficiencies in immortalized cell lines such 293T and K562. In contrast, surprisingly and unexpectedly a double guide strategy with a pair of gRNAs with different offsets targeting the locus of interest resulted in up to 40% homozygous deletion efficiency in HPCs and T cells. These results establish a novel approach through which the CRISPR/Cas9 system can be used to edit the genome in clinically relevant somatic cells with high efficiency.

Results

Efficient and Rapid Genome Editing Using the CRISPR/Cas9 System in Cell Lines

Figure 4C:
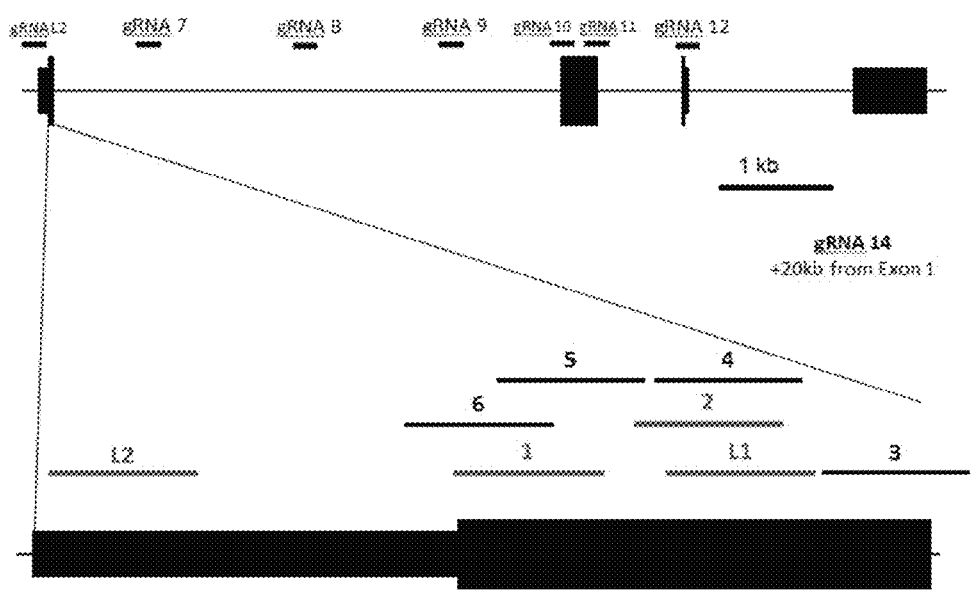
Figure 4D:
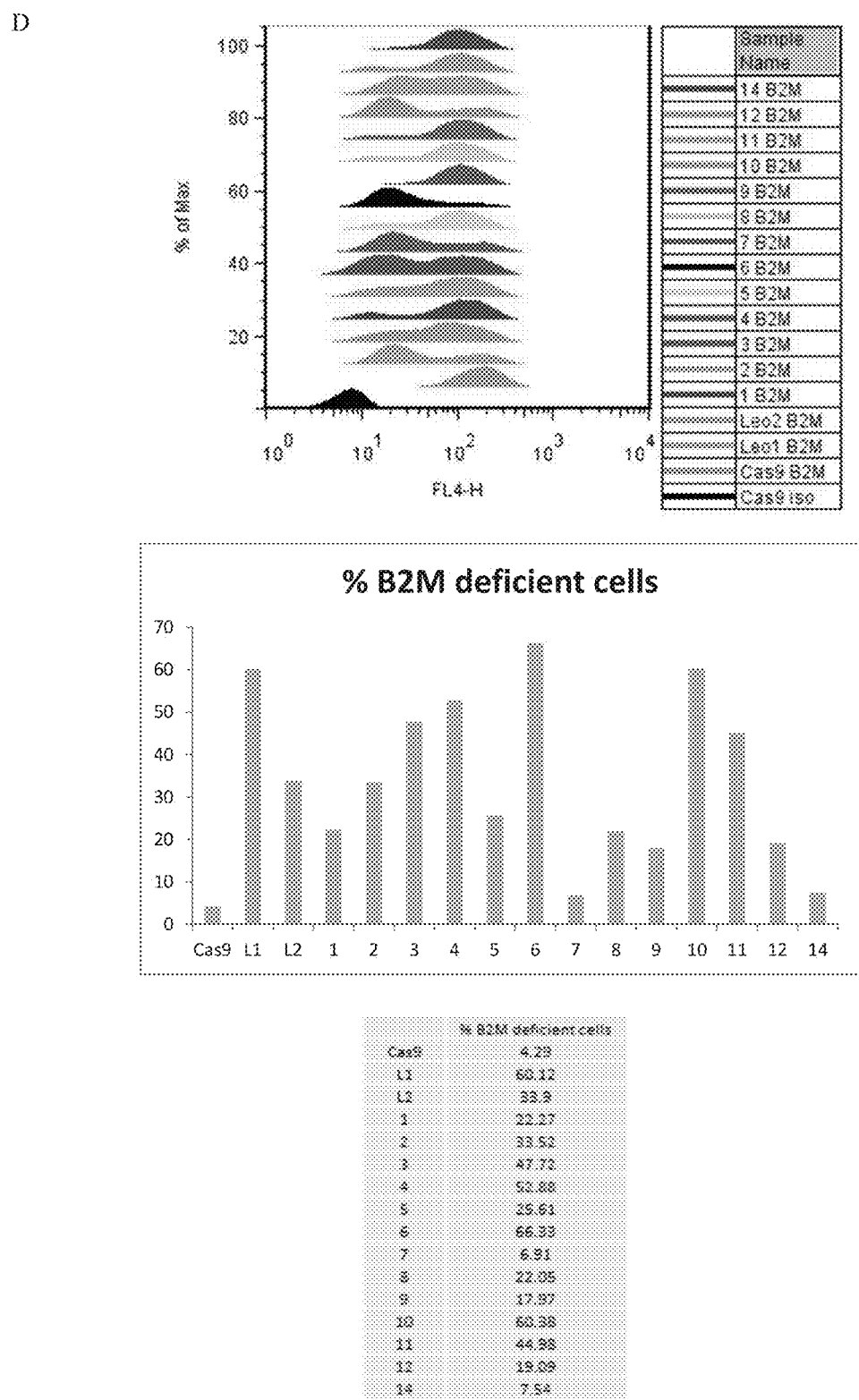
Figure 4E:
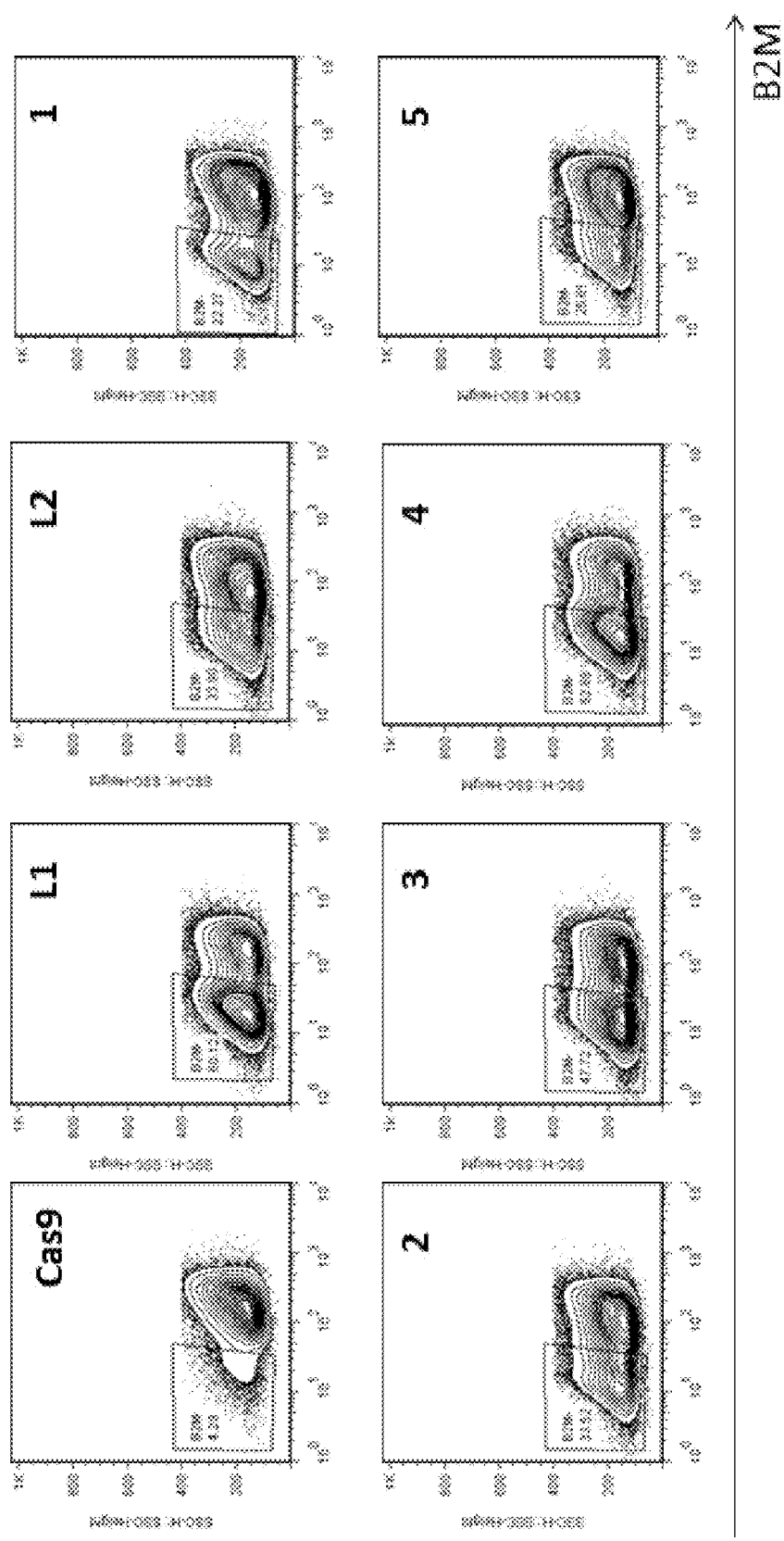
Figure 4E:
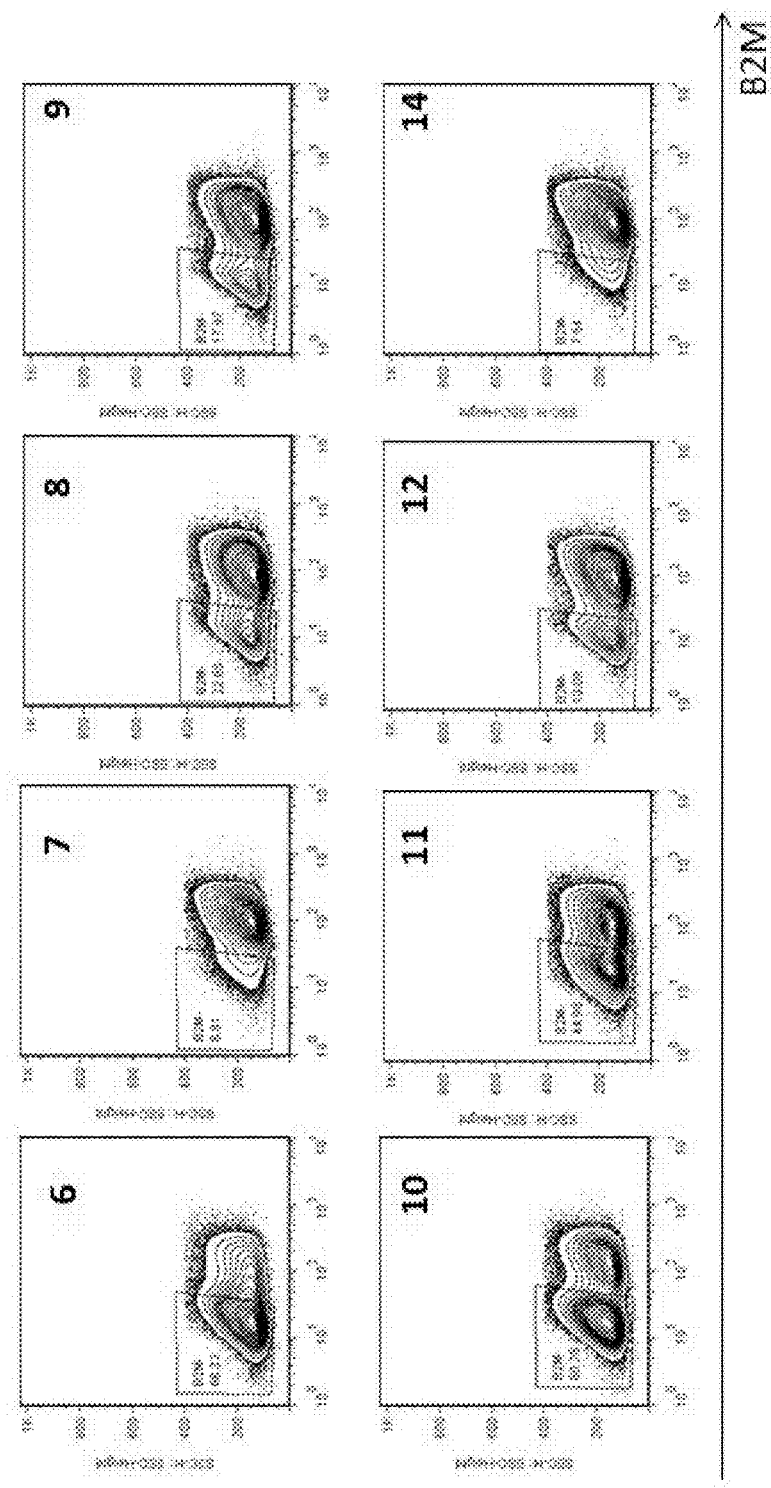

The inventors transfected HEK293T cells with Cas9 and a series of CRISPR guide RNAs targeting the B2M locus and measured cutting efficiency based on SURVEYOR assays (FIG. 4), as well as flow cytometry, taking advantage of the fact that B2M is a surface antigen. These experiments were performed only 72h post-transfection, in order to account for the half-life of B2M on the cell membrane. Of note, B2M surface expression was abrogated in up to 60% of transfected HEK293T cells (FIG. 4). In addition, the inventors observed a wide variation of efficiency between individual guide RNAs, even if targeting the same exon. For instance, variation between single guide cutting efficiencies was several-fold amongst the seven guide RNAs binding within the 67 bp long protein coding portion of the first exon of B2M (FIG. 1X), strongly suggesting that CRISPR cutting efficiency is primarily guide sequence-dependent.

Primary Somatic Cells are Refractory to CRISPR/Cas9 Targeting

Next, the inventors tested the CRISPR/Cas9 system in primary cells. We chose two clinically relevant immune cell types: primary CD34$^+$ hematopoietic progenitor cells (HPCs) and primary CD4$^+$ T cells isolated from peripheral blood. Surprisingly, the same guide RNAs that resulted in up to 60% cutting efficiency in a cell line (B2M in 293T cells, FIG. 4) revealed ineffective in somatic cells (FIG. 4). The inventors speculate that such dramatic drop in targeting efficiency in primary cells is due to either a lower expression level of Cas9 nuclease in nucleofected cells, enhanced DNA repair mechanisms, or a combination of both.

Double Guide Strategy Dramatically Increases Targeting Efficiency in Primary Cells The inventors sought to determine whether genome editing efficacy in clinically relevant primary cells using the CRISPR/Cas9 system could be improved, hoping to achieve targeting efficiencies high enough to be potentially used in therapy. The inventors devised a double guide strategy, where two CRISPR guide RNAs targeting the same locus were delivered to cells simultaneously.

Addition of another guide RNA targeting the HPRT locus almost invariably resulted in increased mutation efficiency compared with the first guide RNA alone. Cells deficient in HPRT were selected by resistance to 6-thioguanine (6-TG). The use of additional gRNAs invariably resulted in increased HPRT mutant frequency. In an embodiment, the target polynucleotide sequence comprises a HPRT gene sequence.

Figures 5A, 5B, 5C, 5D:
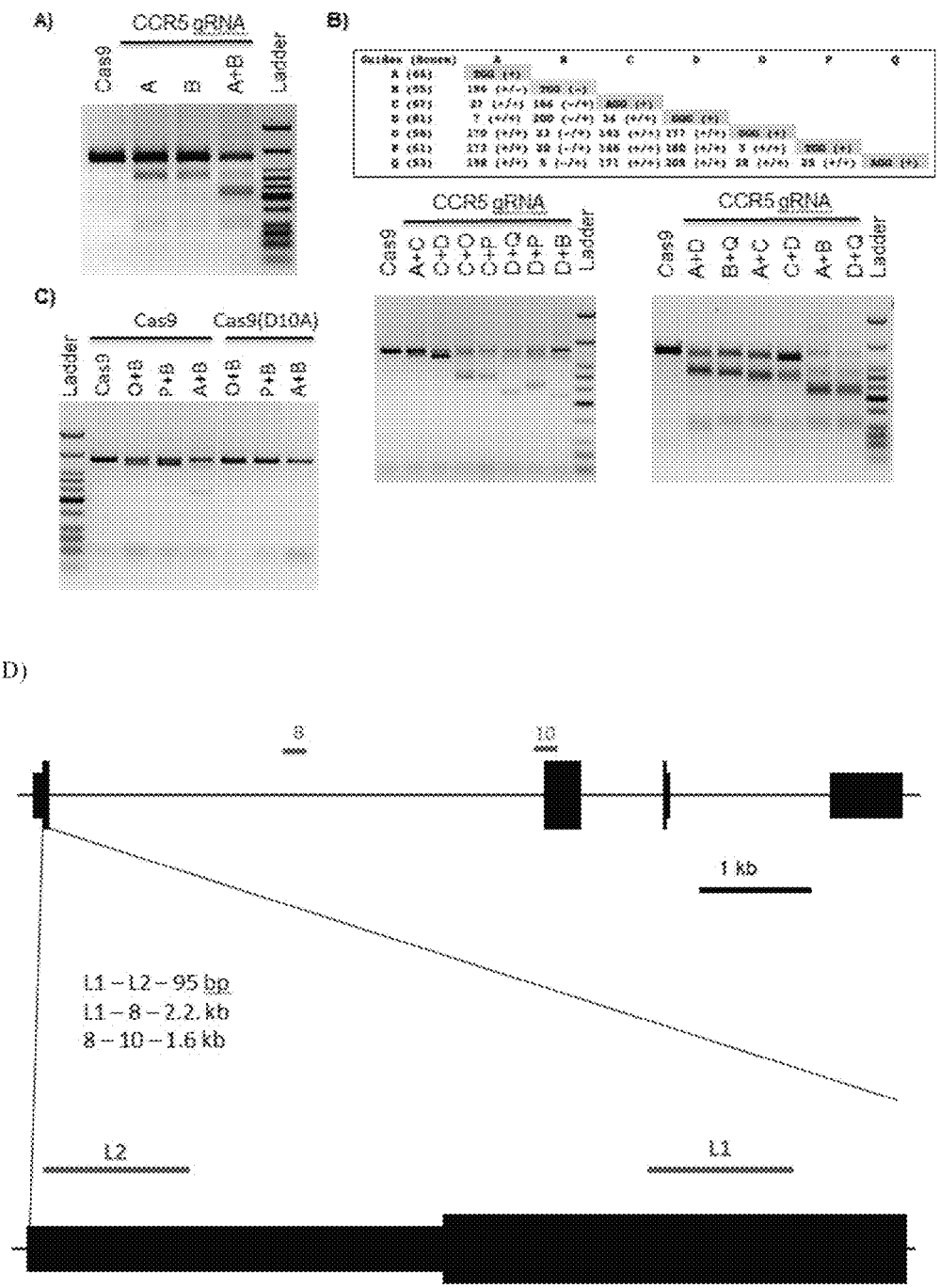
FIGS. 5A, 5B and 5C demonstrate that a double guide strategy achieves genome editing with high efficacy in clinically relevant cells.
FIG. 5D is a schematic showing double B2M CRISPR combinations.
Figures 6A, 6B:
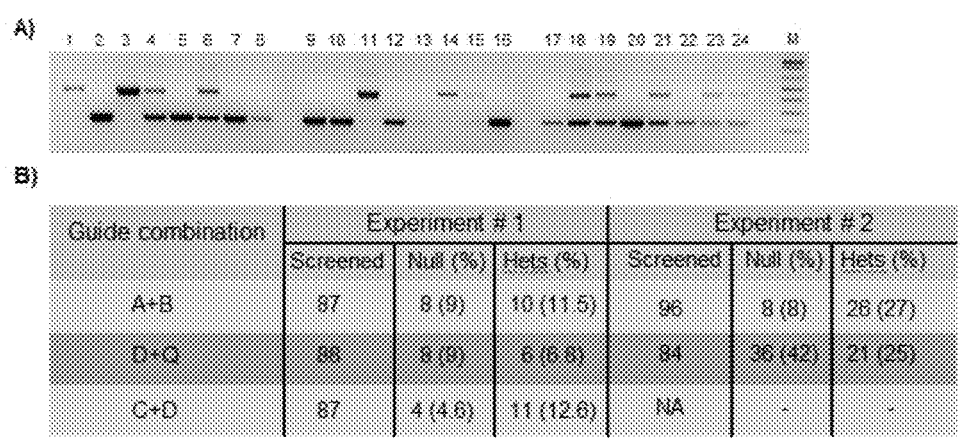
FIGS. 6A and 6B demonstrate effective genome-editing in human CD34+HSPC using a two-guide approach.
Figure 7A:
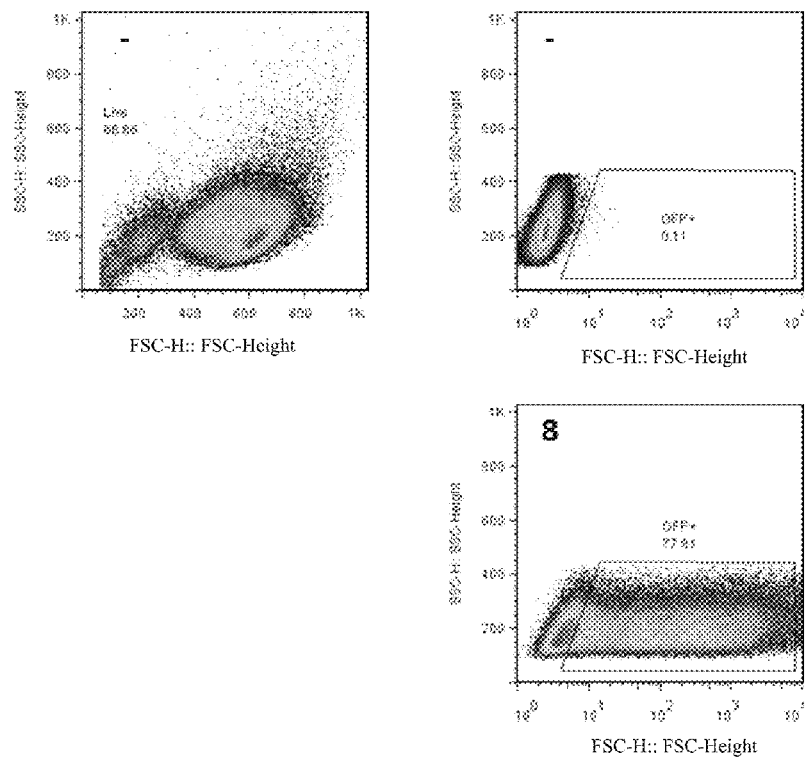
FIGS. 7A, 7B and 7C demonstrate that in contrast to primary cells, the double guide strategy does not improve B2M editing efficiency in 293T cells.
Figure 7B:
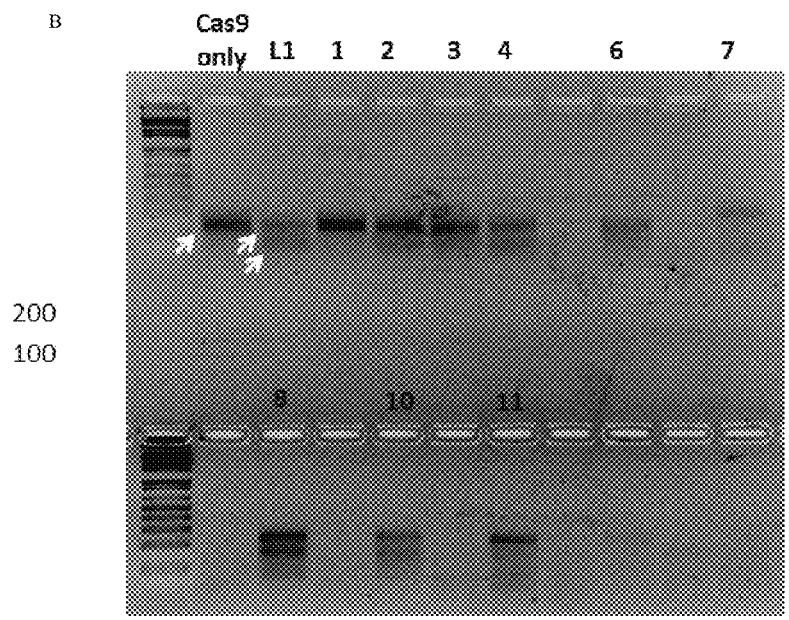
Figure 7C:
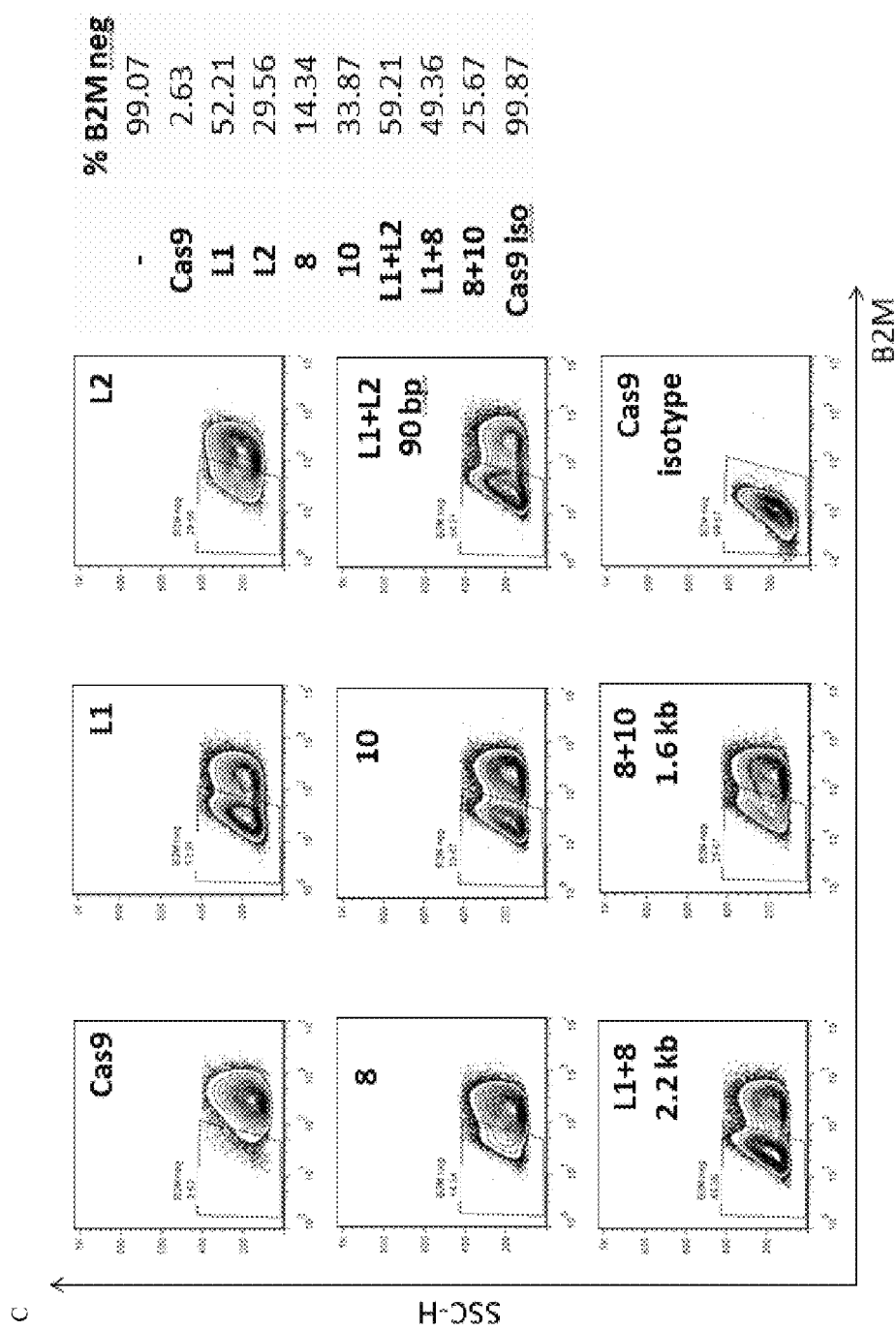
Figures 8A, 8B:
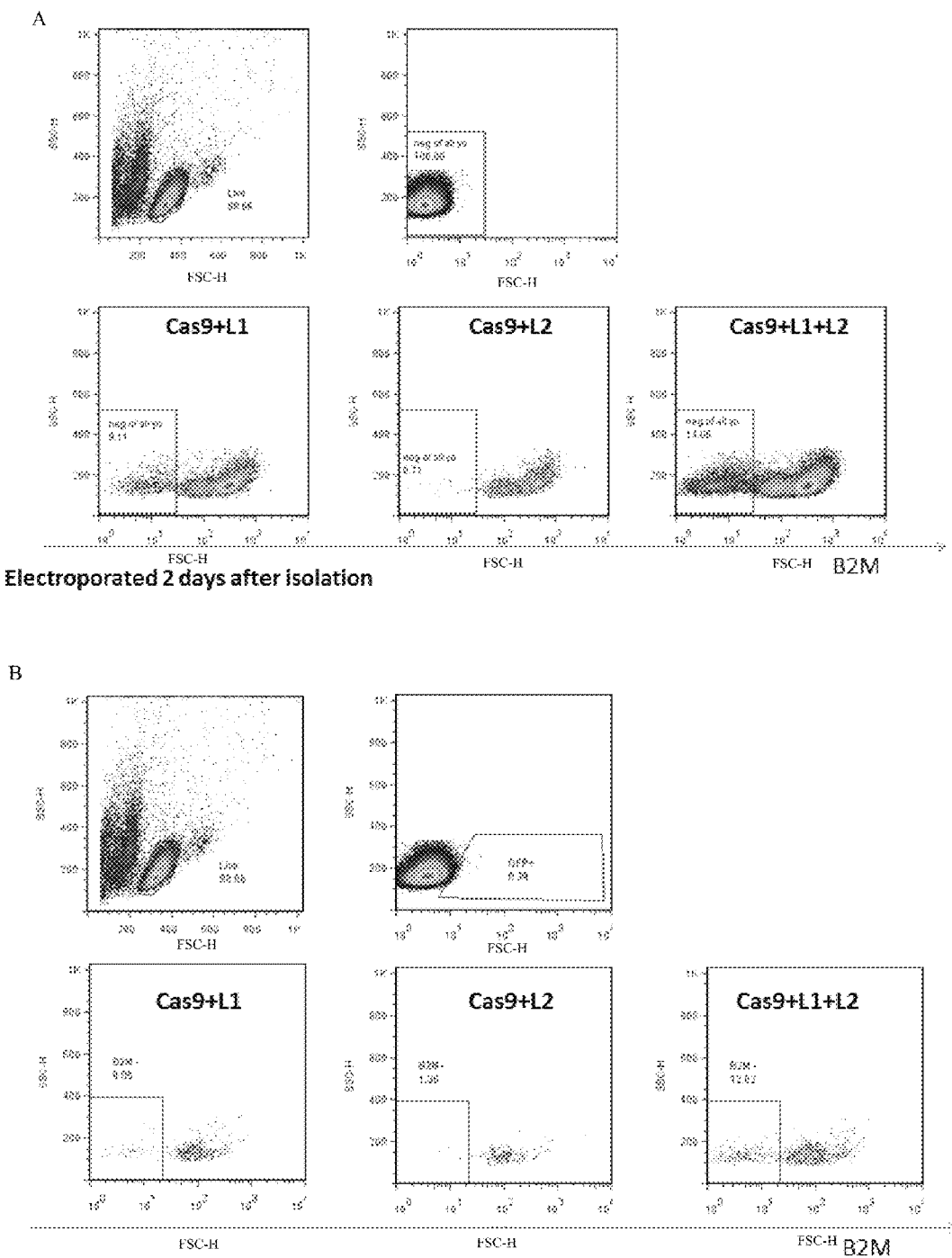
FIGS. 8A, 8B, 8C and 8D demonstrate ablation of B2M surface expression in somatic cells (e.g., primary CD4+ T cells) using a double guide strategy.
Figure 8C:
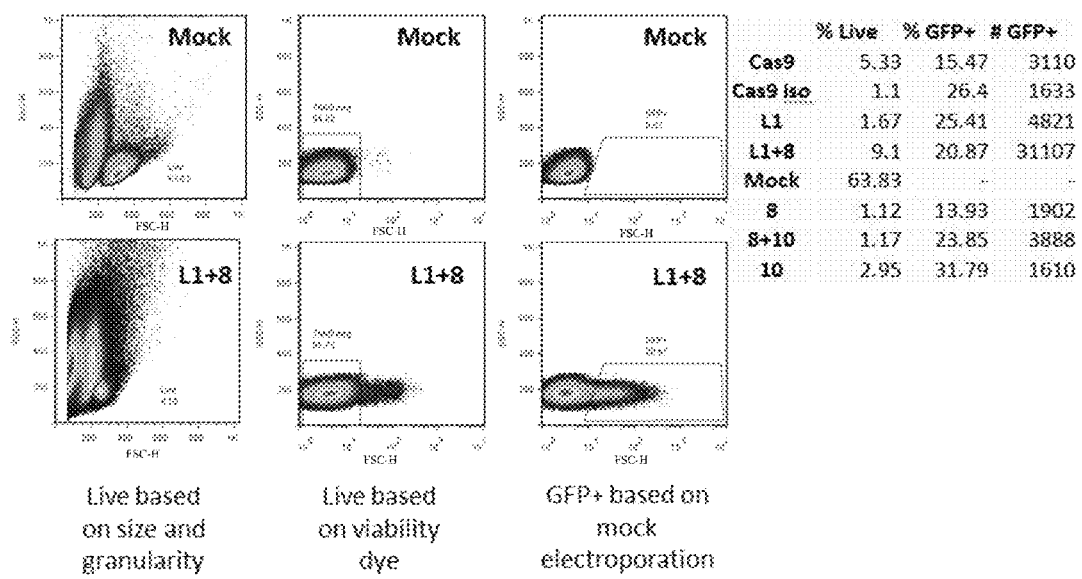
Figure 8D:
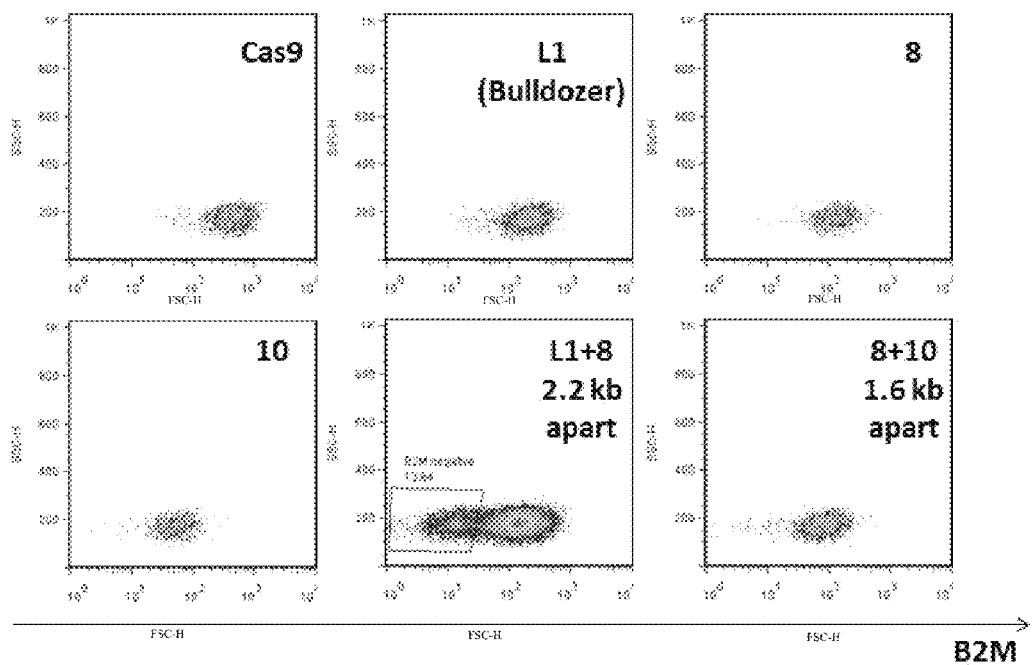

Different guide RNA pairs were tested for each locus, and the most active one was used for further studies with primary cells. FIGS. 4A-4E demonstrate that the single guide strategy achieves high efficiency genome editing in cell lines, but not in clinically relevant primary somatic cells. In the two systems we used, the double guide strategy consistently and substantially outperformed the traditional single guide strategy in primary somatic cells. These results are demonstrated in FIGS. 5A-5E, which show that the double guide strategy achieves genome editing with high efficiency in clinically relevant cells.

Discussion

One of the major focuses in the field of CRISPR/Cas9 genome editing field is the search for parameters that modulate cutting efficiency by Cas9. The data described herein suggest that this phenomenon appears to be mostly determined by gRNA sequence, as gRNAs matching very close or even partially overlapping sequences within the same exon result in significantly different targeting efficiencies (FIG. 4).

In a previous report, an approach combining a Cas9 nickase mutant with paired guide RNAs to introduce targeted double-strand breaks has been used to drastically reduce CRISPR off-target effects without sacrificing on-target efficiency (Ran et al., 2013). In our hands, however, this strategy did not yield a significant mutation rate (Max & Pankaj). We thus combined WT Cas9 with pairs of gRNAs to increase cutting efficiency in cell types refractory to targeting-primary somatic cells.

B2M is an accessory chain of the MHC class I proteins, being necessary for their expression on the cells surface. Engineering cells devoid of surface MHC class I, hence invisible to cytotoxic T cells, is of utmost importance in transplantation and adoptive cell therapy.

Altogether, our data shows that the CRISPR/Cas9 system can be used to edit the genome of clinically relevant primary somatic cells with significant efficiencies by using a double guide strategy. We predict that this strategy has the potential to be a general approach to target genes in somatic cells with a high enough efficiency that it becomes relevant for potential translation into therapeutics.

Experimental Procedures

Flow Cytometry.

Cells were stained with mouse monoclonal anti-B2M antibody 2M2 (Biolegend).

Primary Blood Cell Electroporation.

Primary CD4+ T cells were isolated from leukopacs (MGH) using RosetteSep CD4 T cell enrichment cocktail (Stem Cell Technologies) and electroporated with endotoxin-free DNA using Amaxa T cell nucleofection kit (Lonza).

6-TG Selection for HPRT Deficiency.

$5*10^6$ cells were used per electroporation, with 25 ug Cas9 and 12.5 ug of each gRNA. For the Cas9 control a non-cutting gRNA was used to keep the total DNA amount the same. FACS sorting ended up being relatively similar at 5-8% GFP 48 hours after EP. Cells were plated out at 40,000 per 10 cm plate per sample, and grown until colonies could clearly be seen. 30 uM 6-Thioguanine (6-TG) in mTESR (e.g., at a concentration of 30 µm) and was used as selection medium for 8-9 days and colonies were counted again. The results are shown in Table 1 below.

TABLE 1

| gRNA | Starting colonies | Final colonies | Percentage | Percentage - Cas9 background |
|---|---|---|---|---|
| Cas9 | 105 | 17 | 0.161904762 | 0.00 |
| 1 | 121 | 55 | 0.454545455 | 0.29 |
| 3 | 118 | 67 | 0.56779661 | 0.41 |
| 5 | 124 | 76 | 0.612903226 | 0.45 |
| 7 | 125 | 27 | 0.216 | 0.05 |
| 9 | 131 | 29 | 0.221374046 | 0.06 |
| 11 | 93 | 63 | 0.677419355 | 0.52 |
| 1 + 5 | 64 | 43 | 0.671875 | 0.51 |
| 1 + 3 | 77 | 45 | 0.584415584 | 0.42 |
| 1 + 7 | 55 | 19 | 0.345454545 | 0.18 |
| 1 + 9 | 60 | 26 | 0.433333333 | 0.27 |
| 1 + 11 | 52 | 32 | 0.615384615 | 0.45 |
| 3 + 5 | 69 | 46 | 0.666666667 | 0.50 |
| 3 + 7 | 55 | 33 | 0.6 | 0.44 |
| 3 + 11 | 38 | 30 | 0.789473684 | 0.63 |
| 7 + 11 | 72 | 41 | 0.569444444 | 0.41 |

Table 2 below shows the results from Table 1 above ranked according to editing efficiency.

TABLE 2

| gRNA | Percentage |
|---|---|
| 3 + 11 | 0.63 |
| 11 | 0.52 |
| 1 + 5 | 0.51 |
| 3 + 5 | 0.50 |
| 1 + 11 | 0.45 |
| 5 | 0.45 |
| 3 + 7 | 0.44 |
| 1 + 3 | 0.42 |
| 7 + 11 | 0.41 |
| 3 | 0.41 |
| 1 | 0.29 |
| 1 + 9 | 0.27 |
| 1 + 7 | 0.18 |
| 9 | 0.06 |
| 7 | 0.05 |
| Cas9 | 0.00 | gRNAs used in the experiments are shown below:

| | | |
|---|---|---|
| 1-gtcttgctcgagatgtgatg | (SEQ ID NO: 298) |
| 3-taaattcttgctgacctgc | (SEQ ID NO: 299) |
| 5-tagatccattcctatgactg | (SEQ ID NO: 300) |
| 7-cttcagtctgataaaatcta | (SEQ ID NO: 301) |
| 9-tttgatgtaatccagcaggt | (SEQ ID NO: 302) |
| 11-cacagagggctacaatgtga | (SEQ ID NO: 303) |

REFERENCES

1. Cong, L., et al., 2013. Multiplex genome engineering using CRISPR/Cas systems. Science. 339, 819-23.
2. Ding, Q., et al., 2013. Enhanced efficiency of human pluripotent stem cell genome editing through replacing TALENs with CRISPRs. Cell Stem Cell. 12, 393-4.
3. Jinek, M., et al., 2013. RNA-programmed genome editing in human cells. Elife. 2, e00471.
4. Li, D., et al., 2013. Heritable gene targeting in the mouse and rat using a CRISPR-Cas system. Nat Biotechnol. 31, 681-3.
5. Mali, P., et al., 2011 RNA-guided human genome engineering via Cas9. Science. 339, 823-6.
6. Niu, Y., et al., 2014. Generation of Gene-Modified Cynomolgus Monkey via Cas9/RNA-Mediated Gene Targeting in One-Cell Embryos. Cell. 156, 836-43.
7. Ran, F. A., et al., 2013. Double nicking by RNA-guided CRISPR Cas9 for enhanced genome editing specificity. Cell. 154, 1380-9.
8. Wang, H., et al., 2013. One-step generation of mice carrying mutations in multiple genes by CRISPR/Cas-mediated genome engineering. Cell. 153, 910-8.

What is claimed is:

1. A method of making a deletion in a target polynucleotide sequence in an isolated mammalian primary cell comprising contacting the mammalian cell with a nucleic acid sequence encoding a clustered regularly interspersed short palindromic repeats-associated 9 (Cas9) protein and two guide ribonucleic acid sequences that hybridize to target sites in the target polynucleotide sequence such that a deletion in the target polynucleotide sequence occurs, and wherein the efficiency of making the deletion in the target polynucleotide sequence is at least 18%.

2. The method according to claim 1, wherein the Cas9 protein is *Streptococcus pyogenes* Cas9 protein or a functional portion thereof.

3. The method according to claim 2, wherein the functional portion comprises a combination of operably linked Cas9 protein functional domains selected from the group consisting of a DNA binding domain, at least one RNA binding domain, a helicase domain, and an endonuclease domain.

4. The method according to claim 1, wherein the nucleic acid sequence encoding the Cas9 protein comprises a modified nucleic acid.

5. The method according to claim 4, wherein the modified nucleic acid comprises a ribonucleic acid containing at least one modified nucleotide selected from the group consisting of pseudouridine, 5-methylcytodine, 2-thio-uridine, 5-methyluridine-5'-triphosphate, 4-thiouridine-5'-triphosphate, 5,6-dihydrouridine-5'-triphosphate, and 5-azauridine-5'-triphosphate.

6. The method according to claim 1, wherein each target site is a 20-nucleotide DNA sequence.

7. The method according to claim 1, wherein each target site is a 20-nucleotide DNA sequence beginning with G and immediately precedes an NGG motif recognized by the Cas protein.

8. The method according to claim 1, wherein each target site is $G(N)_{19}NGG$.

9. The method according to claim 1, wherein the target polynucleotide sequence encodes CCR5.

10. The method according to claim 1, wherein the target polynucleotide sequence encodes CXCR4.

11. The method according to claim 1, wherein the Cas9 protein is from any bacterial species or a functional portion thereof.

12. The method according to according to claim 11, wherein the functional portion comprises a combination of operably linked Cas9 protein functional domains selected from the group consisting of a DNA binding domain, at least one RNA binding domain, a helicase domain, and an endonuclease domain.

* * * * *

UNITED STATES PATENT AND TRADEMARK OFFICE
CERTIFICATE OF CORRECTION

PATENT NO. : 9,822,370 B2  
APPLICATION NO. : 14/485288  
DATED : November 21, 2017  
INVENTOR(S) : Kiran Musunuru, Chad A. Cowan and Derrick J. Rossi It is certified that error appears in the above-identified patent and that said Letters Patent is hereby corrected as shown below:

Column 184, Claim 12, Line 12, please delete "according to according to" and insert --according to--.

Signed and Sealed this  
Third Day of April, 2018

Andrei Iancu  
*Director of the United States Patent and Trademark Office*

UNITED STATES PATENT AND TRADEMARK OFFICE
CERTIFICATE OF CORRECTION

PATENT NO. : 9,822,370 B2
APPLICATION NO. : 14/485288
DATED : November 21, 2017
INVENTOR(S) : Kiran Musunuru et al.

It is certified that error appears in the above-identified patent and that said Letters Patent is hereby corrected as shown below:

In the Specification

Column 1, Line 17 through Line 18, please delete "HL107440, R01-HL118744, R00-HL098364 and R01-DK095384" and insert --HL107440, HL118744, HL098364 and DK095384--.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*